United States Patent
Bawage et al.

(10) Patent No.: US 11,795,456 B2
(45) Date of Patent: Oct. 24, 2023

(54) MRNA DRIVEN EXPRESSION OF RNA EDITORS FOR TREATMENT OF PATHOLOGIES

(71) Applicant: Georgia Tech Research Corporation, Atlanta, GA (US)

(72) Inventors: Swapnil Bawage, Atlanta, GA (US); Pooja M. Tiwari, Atlanta, GA (US); Philip J. Santangelo, Atlanta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 100 days.

(21) Appl. No.: 17/047,978

(22) PCT Filed: Apr. 15, 2019

(86) PCT No.: PCT/US2019/027493
§ 371 (c)(1),
(2) Date: Oct. 15, 2020

(87) PCT Pub. No.: WO2019/204210
PCT Pub. Date: Oct. 24, 2019

(65) Prior Publication Data
US 2021/0163938 A1  Jun. 3, 2021

Related U.S. Application Data

(60) Provisional application No. 62/658,046, filed on Apr. 16, 2018.

(51) Int. Cl.
*C12N 15/113* (2010.01)
*C12N 9/22* (2006.01)

(52) U.S. Cl.
CPC .............. *C12N 15/113* (2013.01); *C12N 9/22* (2013.01); *C12N 2310/20* (2017.05); *C12N 2310/321* (2013.01); *C12N 2310/322* (2013.01); *C12N 2310/335* (2013.01)

(58) Field of Classification Search
None
See application file for complete search history.

(56) References Cited

U.S. PATENT DOCUMENTS

| | | | |
|---|---|---|---|
| 2005/0234222 A1* | 10/2005 | Deonarain | A61K 41/0071 530/391.1 |
| 2013/0123481 A1* | 5/2013 | de Fougerolles | C12N 15/11 536/23.1 |
| 2016/0317677 A1* | 11/2016 | Bhatia | C12N 15/113 |
| 2017/0362644 A1* | 12/2017 | Doudna | C12Q 1/6823 |
| 2021/0403925 A1* | 12/2021 | Chevessier-Tünnesen | C12N 15/67 |

FOREIGN PATENT DOCUMENTS

| | | |
|---|---|---|
| WO | 2015/184262 A1 | 12/2015 |
| WO | 2017066588 A2 | 4/2017 |
| WO | 2017219027 A1 | 12/2017 |

OTHER PUBLICATIONS

Shmakov et al. Nature Reviews Microbiology 15, 169-182 (Year: 2017).*
International Preliminary Report on Patentability received for PCT Patent Application No. PCT/US19/27493, dated Oct. 29, 2020, 6 pages.
International Search Report and Written Opinion received for PCT Patent Application No. PCT/US19/27493, dated Jul. 11, 2019, 6 pages.
Jagadesh et al., "Influenza virus neuraminidase (NA): a target for antivirals and vaccines", Arch. Virol., 161(8):2087-2094 (2016).
Liu et al., "The Molecular Architecture for RNA-Guided RNA Cleavage by Cas13a," Cell. 170(4):714-726.e10, (2017).
Sultana et al., "Optimizing Cardiac Delivery of Modified mRNA," Mol. Ther., 25(6):1306-1315, (2017).
English translation of Notice of Reasons for Rejection for Japanese Application No. 2020-557252 dated Jan. 30, 2023, 3 pages.

* cited by examiner

*Primary Examiner* — Brian Whiteman
(74) *Attorney, Agent, or Firm* — Meunier Carlin & Curfman LLC

(57) ABSTRACT

Compositions and methods for treating or inactivating viruses in a subject in need thereof are provided herein. Exemplary compositions include nucleic acids encoding an RNA-guided endonuclease and a guide RNA that is complementary to a target sequence in a virus. The RNA-guided endonuclease specifically targets viral nucleic acid sequences for destruction and suppression of that virus in a host cell in vitro or in vivo.

10 Claims, 31 Drawing Sheets

Figure 1A:
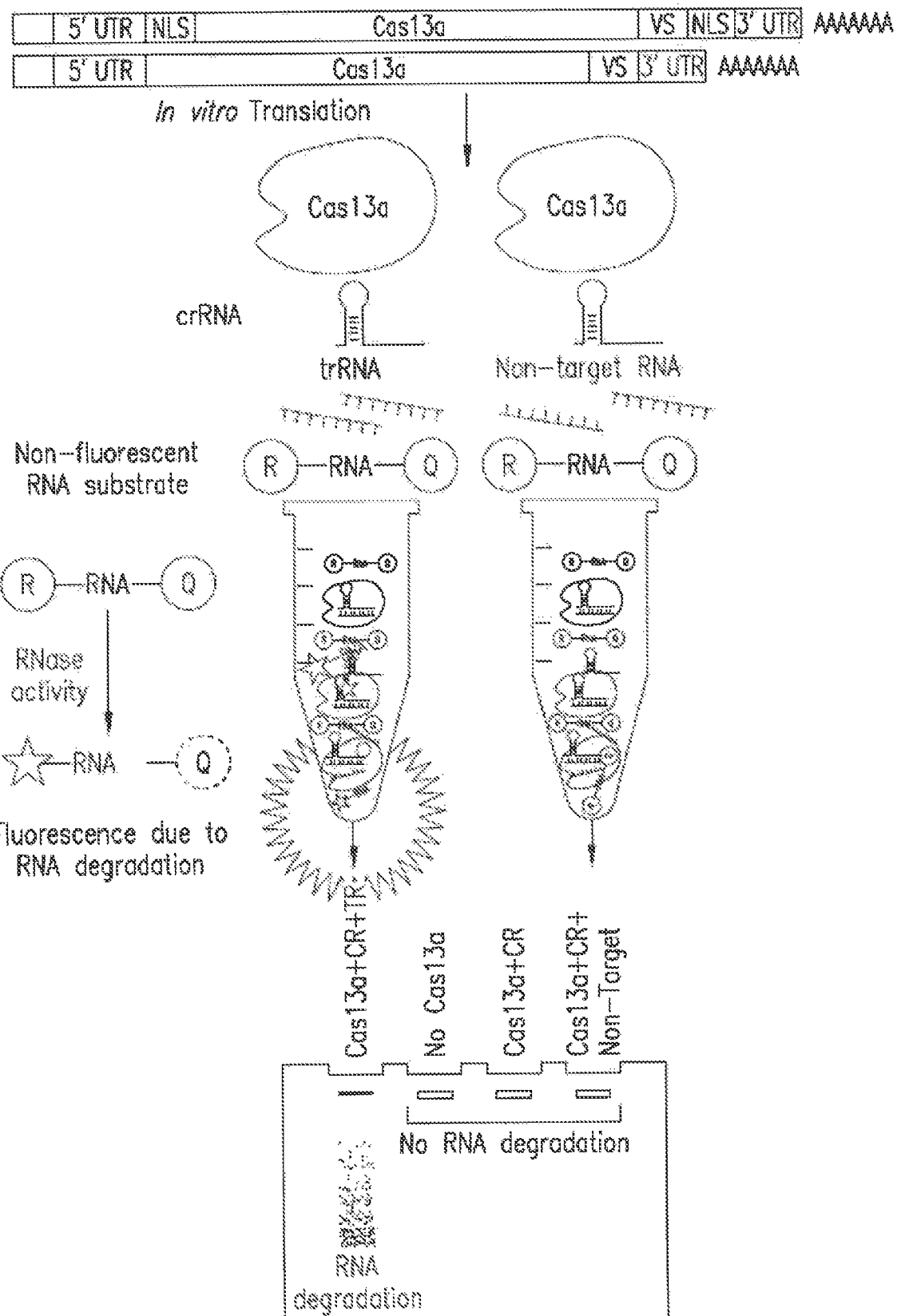

Specification includes a Sequence Listing.

SEQUENCE LISTING

```
<160> NUMBER OF SEQ ID NOS: 110

<210> SEQ ID NO 1
<211> LENGTH: 3705
<212> TYPE: DNA
<213> ORGANISM: Artificial Sequence
<220> FEATURE:
<223> OTHER INFORMATION: Synthetic

<400> SEQUENCE: 1
ttttaagctt taatacgact cactataggg aaataagaga gaaagaaga gtaagaagaa      60 atataagagc caccatgaaa gtgacgaagg taggaggcat ttcgcataag aagtacacgt     120
ccgaaggccg cttagtgaag tcagaatcgg aagaaaatcg cacagacgaa cgtctgtcgg     180
cgttgcttaa tatgcgcctt gacatgtata tcaagaatcc cagcagcacg gaaaccaagg     240
aaaatcaaaa acgcattggg aaattaaaga aattcttctc aaacaaaatg gtctatctta     300
aagacaatac cttgagtttg aagaatggga aaaggagaa cattgatcgt gagtattctg     360
agactgacat ccttgagagc gatgtccgtg acaagaaaaa cttcgccgtg ttgaaaaaga     420
tctatctgaa tgaaaacgtg aactcggagg aattggaagt ttttcgtaac gacattaaga     480
agaaactgaa caaaatcaac agcctgaagt actcatttga aaagaataag gcgaattatc     540
aaaagattaa tgagaataac atcgagaagg ttgaaggtaa gtcaaagcgt aacattattt     600
acgattatta tcgtgagtca gcgaaacgtg acgcttatgt aagcaatgtg aaagaagcct     660
ttgataagct ttacaaggaa gaggacattg caaaacttgt tcttgaaatt gagaaccttla    720 cgaagttaga gaaatacaag attcgcgagt tctaccacga aattattgga cgtaagaatg     780
acaaggaaaa ctttgcaaaa atcatctacg aagaaatcca gaatgttaat aacatgaaag     840
agttgatcga gaaggtaccg gacatgagtg agttgaaaaa gagccaagta ttttacaagt     900
attacttaga caaagaagag ttgaacgaca agaacatcaa atacgcgttt tgtcatttcg     960
tggaaatcga aatgagtcag ttgctgaaga actacgtata taagcgctta agtaatatct    1020
cgaatgacaa aattaagcgt atctttgaat accagaactt gaaaaaattg atcgaaaata    1080
agctgttaaa caaacttgac acgtacgtcc gtaattgtgg aaagtataat tattatttgc    1140
aagacggcga aattgccact tcagatttca tcgcccgcaa ccgtcagaat gaagcgtttc    1200
ttcgcaacat cattggggtg tcatctgtgg cctactttte tcttcgcaac attcttgaaa    1260
cggagaacga gaatgatatt actgggcgta tgcgcggcaa aacagttaag aacaataaag    1320
gtgaagagaa gtacgtgtcc ggagaagttg ataagatcta taatgaaaat aagaagaacg    1380
aggttaagga gaacttaaaa atgttctatt cgtacgattt caatatggac aacaagaatg    1440
aaatcgaaga tttcttcgcc aacatcgacg aggcgatttc ttccatccgt cacggtattg    1500
tccacttcaa cttggaatta gaaggtaagg atatctttgc gttcaagaac attgcgccat    1560
ccgaaatctc aaagaagatg tttcagaatg agattaacga gaaaaaactg aaattgaaga    1620
tctttcgtca actgaactct gccaacgtgt tccgctatct cgaaaagtat aaaattctga    1680
```

```
attaccttaa acgtacacgc ttcgagtttg tcaataaaaa tatcccattc gtcccgtctt    1740
tcaccaaatt atattcgcgc attgatgacc tgaagaatag tcttgggatt tactggaaaa    1800
ctccgaaaac aaacgacgac aataagacta aggagattat tgatgcccaa atctatttgc    1860
ttaaaaacat ctattacggg gagttcctga attatttcat gtcgaacaat ggtaatttct    1920
ttgagatttc taaagaaatc atcgaattga caagaacga taaacgcaac ttaaagactg    1980
ggttttacaa gctgcaaaag tttgaagaca tccaggagaa gattccaaag gaatacttgg    2040
cgaatatcca gtccctgtac atgattaatg ccggtaatca ggacgaagaa gaaaaggaca    2100
cttatattga tttcattcaa aagatcttct taaagggatt tatgacgtat cttgctaata    2160
acggtcgttt aagtctgatt tacatcggct cggatgaaga aacaaatacg tcattagcag    2220
aaaagaagca agagtttgac aagttcttga agaagtacga gcagaacaat aatatcaaga    2280 tccctatga gatcaatgaa ttcctgcgtg agatcaaact gggaaacatc ctgaagtata    2340
ctgagcgttt aaacatgttc taccttatct taaagctttt gaatcacaag gagctgacaa    2400
atctgaaggg tagtcttgaa aaatatcagt ctgccaataa ggaagaagcg ttctctgacc    2460
aattggagtt aattaacctg cttaaccttg acaacaaccg cgtgacggaa gacttcgaat    2520
tagaggccga cgagattgga aaatttcttg atttcaatgg caacaaagtt aaggataaca    2580
aggaactgaa aaagttcgat acaaacaaga tctactttga cggcgagaac attatcaaac    2640
accgtgcctt ctacaatatt aagaaatatg gcatgttaaa cttactggag aaaattgccg    2700
acaaggctgg atacaagatc tcgatcgaag agctgaagaa atactccaat aaaaagaatg    2760
agatcgagaa gaaccataag atgcaggaaa atctgcaccg caaatacgct cgtccccgta    2820
aagacgagaa gtttacagat gaggactatg aaagttacaa gcaagctatt gagaatattg    2880
aggagtacac ccaccttaag aacaaggtag aattcaatga gctgaattta ctgcagggcc    2940
tgttgctgcg cattttacat cgtttagtcg gatatacctc aatttgggaa cgcgatctgc    3000
gcttccgcct taaaggtgag ttcccagaaa accaatacat cgaagagatc ttcaactttg    3060
aaaataagaa gaacgtgaag tacaaagggg gtcagattgt agagaaatac attaaattct    3120
acaaggaatt acatcaaaat gatgaagtta agatcaacaa gtacagttcc gcgaatatca    3180
aggtgttgaa gcaagaaaag aaggacccttt atattcgaaa ttacatcgcc cacttcaatt    3240
atattcctca cgccgagatc tcactgctgg aagtccttga aaatttgcgt aaatttgctgt    3300 cctacgatcg caaactgaaa aatgccgtaa tgaaatcagt agttgatatc cttaaggagt    3360
atggttttgt agccacattc aaaatcgggg cggacaagaa gatcggtatt cagacactgg    3420
agagcgaaaa aatcgtgcat cttaagaatc ttaagaagaa gaagttaatg actgaccgca    3480
attccgagga actttgcaaa ttggtgaaga ttatgtttga atacaaaatg gaagagaaaa    3540
agtctgaaaa cggtaagcct atccctaacc ctctcctcgg tctcgattct acgtgataag    3600
ctgccttctg cggggcttgc cttctggcca tgcccttctt ctctcccttg cacctgtacc    3660
tcttggtctt tgaataaagc ctgagtagga aggcggccgc aaaaa           3705
```

<210> SEQ ID NO 2
<211> LENGTH: 3803
<212> TYPE: DNA
<213> ORGANISM: Artificial Sequence
<220> FEATURE:
<223> OTHER INFORMATION: Synthetic

<400> SEQUENCE: 2

```
gcggaaggcc gtcaaggccg cattttttaag ctttaatacg actcactata gggaaataag    60
agagaaaaga agagtaagaa gaaatataag agccaccatg cccaaaaaga agaggaaagt    120
gggatccatg aaagtgacca aagtcggcgg catcagccac aagaagtaca cctctgaggg    180
cagactggtc aagagcgaga gcgaggaaaa ccggaccgac gagagactga gcgccctgct    240
gaacatgcgg ctggacatgt acatcaagaa ccccagcagc accgagacaa aagagaacca    300
gaagcggatc ggcaagctga agaagttctt tagcaacaag atggtgtacc tgaaggacaa    360
caccctgagc ctgaagaacg gcaagaaaga gaacatcgac cgcgagtaca gcgagacaga    420
catcctggaa agcgacgtgc gggacaagaa aaacttcgcc gtgctgaaga aaatctacct    480
gaacgagaac gtgaacagcg aggaactgga agtgttccgc aacgatatca agaagaagct    540
gaacaagatc aacagcctga gtacagcctt cgagaagaac aaggccaact accagaaagat    600 caacgagaac aacatcgaga aggtggaagg caagagcaag cggaacatca tctacgacta    660
ctacagagag agcgccaagc gggacgccta cgtgtccaat gtgaaagagg ccttcgacaa    720
gctgtacaaa gaggaagata tcgccaagct ggtgctcgaa tcgagaaacc tgaccaagct    780
ggaaaagtac aagatccgcg agttctacca cgagatcatc ggccggaaga cgacaaaga    840 gaacttcgcc aagatcatct atgaagagat ccagaacgtc aacaacatga aggaactgat    900
tgagaaggtg cccgacatga gcgagctgaa aaagtcccag gtgttctaca agtactacct    960
ggacaaagaa gaattgaacg acaagaatat taagtacgcc ttctgccact cgtggaaat    1020 cgagatgagc cagctgctga aaaactacgt gtacaagcgg ctgagcaaca tcagcaacga   1080
taagatcaag cggatcttcg agtaccagaa cctgaagaag ctcattgaga acaagctgct    1140
caacaagctc gacacctacg tgcggaactg cggcaagtac aactactatc tgcaagacgg    1200
cgagatcgcc accagcgact ttatcgcccg gaacagacag aacgaggcct tcctgagaaa    1260
catcatcggc gtgtccagcg tggcctactt cagcctgcgg aacattctgg aaaccgagaa    1320
cgagaatgac atcaccggcc ggatgagagg caagaccgtg aaaaacaaca gggcgaaga    1380 gaaatacgtg tccggcgagg tggacaagat ctacaatgag aacaaaaaga cgaagtgaa   1440 agaaaacctc aagatgttct acagctacga cttcaacatg gacaacaaga atgagatcga    1500
ggacttcttc gccaacatcg acgaggccat cagcagcatc agacacggca tcgtgcactt    1560
caacctcgag ctgaagggga agacatcctt cgccttcaag aatatcgccc tagcgagat    1620 cagcaagaag atgttccaga cgagatcaa tgagaagaaa ctgaagctca gatcttccg    1680 gcagctgaac agcgccaacg tgttcagata cctcgagaag tataagatcc tgaactacct    1740
gaagcggacc cgcttcgagt tcgtgaacaa gaacatcccc ttcgtgccca gcttcaccaa    1800
gctgtatagc cggatcgacg atctgaagaa cagcctgggc atctactgga aaccccctaa    1860
gaccaacgac gataacaaga ccaaagagat cattgacgcc cagatctacc tcctcaagaa    1920
tatctactac ggcgagttcc tgaattactt catgagcaac aacggcaact tcttcgagat    1980
ctccaaagaa atcatcgaac tcaacaagaa cgataagcgg aacctgaaaa ccggcttcta    2040
caagctgcag aaattcgagg acatccaaga gaagatcccc aaagagtacc tggccaacat    2100
ccagagcctg tacatgatca acgccggcaa ccaggacgag gaagagaagg acacctacat    2160
cgactttatt cagaagattt tcctgaaggg cttcatgacc tacctggcta caacggccg    2220 gctgtccctg atctacatcg gcagcgacga ggaaacaaac accagcctgg ccgagaaaaa    2280
gcaagagttc gacaagttcc ttaagaagta cgagcagaac aacaacatca agatcccgta    2340
cgagattaac gagttcctcc gcgagatcaa gctggggaac atcctcaagt acaccgagcg    2400
```

```
gctgaatatg ttctacctga tcctgaaact gctgaaccac aaagagctga ccaatctgaa    2460
gggaagcctc gagaaatacc agtccgccaa caaagaagag gcctttagcg accagctgga    2520
actgatcaac ctgctgaatc tcgacaacaa cagagtgacc gaggactttg aactcgaggc    2580
cgacgagatc ggaaagttcc tggacttcaa tggcaacaaa gtgaaggata caaagaact     2640 caagaagttc gataccaaca aaatctactt cgacggggag aatatcatca agcaccgggc    2700
cttctacaac attaagaaat acggcatgct gaacctgctc gagaagatcg ccgataaggc    2760
cggctacaag atcagcattg aggaactgaa gaaatactcc aacaagaaga cgagattga     2820 gaagaaccac aagatgcaag agaacctgca ccggaagtac gccagacctc ggaaggacga    2880
gaagttcacc gacgaggatt acgagagcta agcaggcc atcgagaata tcgaagagta     2940
cacccacctc aagaacaaag tggaattcaa cgagctgaat ctgctgcagg gcctgctgct    3000
gagaatcctg catagactcg tgggctacac cagcatctgg gagcgcgacc tgagattcag    3060
actgaagggc gagtttcccg agaaccagta catcgaggaa atcttcaact tcgaaaacaa    3120
aaaaaacgtg aagtacaaag gcggccagat cgttgagaag tacattaagt tctacaaaga    3180
attgcaccag aacgacgaag tcaagattaa caagtcagc agcgccaata tcaaggtgct     3240
gaagcaagag aaaaaggacc tgtacatccg gaactatatc gcccacttca actacatccc    3300
tcacgccgag attagcctgc tggaagtgct ggaaaatctg cggaagctgc tgagctacga    3360
ccggaaactg aaaaacgccg tgatgaagtc cgtggtggat atcctgaaag aatacggctt    3420
cgtggccacc ttcaagatcg agccgacaa gaagatcggc atccgacac tggaatccga      3480 aaagatcgtg cacctgaaaa atctgaaaaa gaaaaagctg atgaccgacc ggaactccga    3540
agaactgtgc aagctcgtga agatcatgtt cgagtacaaa atggaagaaa agaaatccga    3600
gaacggatcc ggtaagccta tccctaaccc tctcctcggt ctcgattcta cgggatcccc    3660
caagaaaaag cgcaaggtat gataagctgc cttctgcggg gcttgccttc tggccatgcc    3720
cttcttctct cccttgcacc tgtacctctt ggtctttgaa taaagcctga gtaggaaggc    3780
ggccgcaaaa actgggcctc atg                                             3803
```

<210> SEQ ID NO 3
<211> LENGTH: 55
<212> TYPE: RNA
<213> ORGANISM: Influenza A virus

<400> SEQUENCE: 3
ggaccacccc aaaaaugaag gggacuaaaa caaacuacug guccuguuau augca          55

<210> SEQ ID NO 4
<211> LENGTH: 55
<212> TYPE: RNA
<213> ORGANISM: Influenza A virus

<400> SEQUENCE: 4
ggaccacccc aaaaaugaag gggacuaaaa caaacuggag gaccuauaua cagga          55

<210> SEQ ID NO 5
<211> LENGTH: 55
<212> TYPE: RNA
<213> ORGANISM: Influenza A virus

<400> SEQUENCE: 5
ggaccacccc aaaaaugaag gggacuaaaa caaagacaau ggcauaagaa uuggu          55

```
<210> SEQ ID NO 6
<211> LENGTH: 55
<212> TYPE: RNA
<213> ORGANISM: Influenza A virus

<400> SEQUENCE: 6
ggaccacccc aaaaaugaag gggacuaaaa caaauaacau ggacaaagca guuaa      55

<210> SEQ ID NO 7
<211> LENGTH: 55
<212> TYPE: RNA
<213> ORGANISM: Influenza A virus

<400> SEQUENCE: 7
ggaccacccc aaaaaugaag gggacuaaaa caaacucuac agagauucgc uugga      55

<210> SEQ ID NO 8
<211> LENGTH: 55
<212> TYPE: RNA
<213> ORGANISM: Influenza A virus

<400> SEQUENCE: 8
ggaccacccc aaaaaugaag gggacuaaaa caaaguggaa ugcaguucuc cucau      55

<210> SEQ ID NO 9
<211> LENGTH: 55
<212> TYPE: RNA
<213> ORGANISM: Influenza A virus

<400> SEQUENCE: 9
ggaccacccc aaaaaugaag gggacuaaaa caaagugcug caacuuauuu gaaaa      55

<210> SEQ ID NO 10
<211> LENGTH: 55
<212> TYPE: RNA
<213> ORGANISM: Influenza A virus

<400> SEQUENCE: 10
ggaccacccc aaaaaugaag gggacuaaaa cuucauacag aagaccaguc gggau      55

<210> SEQ ID NO 11
<211> LENGTH: 55
<212> TYPE: RNA
<213> ORGANISM: Influenza A virus

<400> SEQUENCE: 11
ggaccacccc aaaaaugaag gggacuaaaa cugaaaaauu cuuccccagc aguuc      55

<210> SEQ ID NO 12
<211> LENGTH: 55
<212> TYPE: RNA
<213> ORGANISM: Influenza A virus

<400> SEQUENCE: 12
ggaccacccc aaaaaugaag gggacuaaaa caaacagauu guguauugga agcaa      55

<210> SEQ ID NO 13
<211> LENGTH: 61
<212> TYPE: RNA
<213> ORGANISM: Artificial Sequence
<220> FEATURE:
<223> OTHER INFORMATION: Synthetic

<400> SEQUENCE: 13
```

```
gguagaccac cccaaaauga aggggacuaa aacacaaauc uaucugaaua aacucuucuu    60
c                                                                   61

<210> SEQ ID NO 14
<211> LENGTH: 26
<212> TYPE: RNA
<213> ORGANISM: Influenza A virus

<400> SEQUENCE: 14
gugcauauaa caggaccagu aguuuc                                        26

<210> SEQ ID NO 15
<211> LENGTH: 26
<212> TYPE: RNA
<213> ORGANISM: Influenza A virus

<400> SEQUENCE: 15
guccuguaua uagguccucc aguuuc                                        26

<210> SEQ ID NO 16
<211> LENGTH: 26
<212> TYPE: RNA
<213> ORGANISM: Influenza A virus

<400> SEQUENCE: 16
gaccaauucu uaugccauug ucuuuc                                        26

<210> SEQ ID NO 17
<211> LENGTH: 26
<212> TYPE: RNA
<213> ORGANISM: Influenza A virus

<400> SEQUENCE: 17
guuaacugcu uuguccaugu uauuuc                                        26

<210> SEQ ID NO 18
<211> LENGTH: 26
<212> TYPE: RNA
<213> ORGANISM: Influenza A virus

<400> SEQUENCE: 18
guccaagcga aucucuguag aguuuc                                        26

<210> SEQ ID NO 19
<211> LENGTH: 26
<212> TYPE: RNA
<213> ORGANISM: Influenza A virus

<400> SEQUENCE: 19
gaugaggaga acugcauucc acuuuc                                        26

<210> SEQ ID NO 20
<211> LENGTH: 26
<212> TYPE: RNA
<213> ORGANISM: Influenza A virus

<400> SEQUENCE: 20
guuuucaaau aaguugcagc acuuuc                                        26

<210> SEQ ID NO 21
<211> LENGTH: 26
<212> TYPE: RNA
```

```
<213> ORGANISM: Influenza A virus

<400> SEQUENCE: 21
gaucccgacu ggucuucugu augaac                                          26

<210> SEQ ID NO 22
<211> LENGTH: 26
<212> TYPE: RNA
<213> ORGANISM: Influenza A virus

<400> SEQUENCE: 22
ggaacugcug gggaagaauu uuucac                                          26

<210> SEQ ID NO 23
<211> LENGTH: 26
<212> TYPE: RNA
<213> ORGANISM: Influenza A virus

<400> SEQUENCE: 23
guugcuucca auacacaauc uguuuc                                          26

<210> SEQ ID NO 24
<211> LENGTH: 72
<212> TYPE: DNA
<213> ORGANISM: Artificial Sequence
<220> FEATURE:
<223> OTHER INFORMATION: Synthetic

<400> SEQUENCE: 24
taatacgact cactatagga ccaccccaaa aatgaagggg actaaaacaa agtgctgcaa      60
cttatttgaa aa                                                         72

<210> SEQ ID NO 25
<211> LENGTH: 72
<212> TYPE: DNA
<213> ORGANISM: Artificial Sequence
<220> FEATURE:
<223> OTHER INFORMATION: Synthetic

<400> SEQUENCE: 25
taatacgact cactatagga ccaccccaaa aatgaagggg actaaaactt ttcaaataag      60
ttgcagcact tt                                                         72

<210> SEQ ID NO 26
<211> LENGTH: 72
<212> TYPE: DNA
<213> ORGANISM: Artificial Sequence
<220> FEATURE:
<223> OTHER INFORMATION: Synthetic

<400> SEQUENCE: 26
taatacgact cactatagga ccaccccaaa aatgaagggg actaaaacaa acaattcaag      60
ccatgggaca aa                                                         72

<210> SEQ ID NO 27
<211> LENGTH: 72
<212> TYPE: DNA
<213> ORGANISM: Artificial Sequence
<220> FEATURE:
<223> OTHER INFORMATION: Synthetic

<400> SEQUENCE: 27
taatacgact cactatagga ccaccccaaa aatgaagggg actaaaactt tgtcccatgg      60
```

-continued

```
cttgaattgt tt                                                           72

<210> SEQ ID NO 28
<211> LENGTH: 23
<212> TYPE: DNA
<213> ORGANISM: Artificial Sequence
<220> FEATURE:
<223> OTHER INFORMATION: Synthetic

<400> SEQUENCE: 28
ggagtgaaat tggaatcaat ggg                                               23

<210> SEQ ID NO 29
<211> LENGTH: 22
<212> TYPE: DNA
<213> ORGANISM: Artificial Sequence
<220> FEATURE:
<223> OTHER INFORMATION: Synthetic

<400> SEQUENCE: 29
aggttctcat ggaatggcta aa                                                22

<210> SEQ ID NO 30
<211> LENGTH: 22
<212> TYPE: DNA
<213> ORGANISM: Artificial Sequence
<220> FEATURE:
<223> OTHER INFORMATION: Synthetic

<400> SEQUENCE: 30
ttaaggacag aagcccttat ag                                                22

<210> SEQ ID NO 31
<211> LENGTH: 23
<212> TYPE: DNA
<213> ORGANISM: Artificial Sequence
<220> FEATURE:
<223> OTHER INFORMATION: Synthetic

<400> SEQUENCE: 31
ctacagagat tcgcttggag aag                                               23

<210> SEQ ID NO 32
<211> LENGTH: 20
<212> TYPE: DNA
<213> ORGANISM: Artificial Sequence
<220> FEATURE:
<223> OTHER INFORMATION: Synthetic

<400> SEQUENCE: 32 gacccttca gactgcttca                                                    20

<210> SEQ ID NO 33
<211> LENGTH: 20
<212> TYPE: DNA
<213> ORGANISM: Artificial Sequence
<220> FEATURE:
<223> OTHER INFORMATION: Synthetic

<400> SEQUENCE: 33
ggatggaagg aacccaatgt                                                   20

<210> SEQ ID NO 34
<211> LENGTH: 22
<212> TYPE: DNA
```

```
<213> ORGANISM: Artificial Sequence
<220> FEATURE:
<223> OTHER INFORMATION: Synthetic

<400> SEQUENCE: 34
atctttgaga cctcgtgtct tg                                              22

<210> SEQ ID NO 35
<211> LENGTH: 21
<212> TYPE: DNA
<213> ORGANISM: Artificial Sequence
<220> FEATURE:
<223> OTHER INFORMATION: Synthetic

<400> SEQUENCE: 35
gtcagtgaaa cacagggaac a                                               21

<210> SEQ ID NO 36
<211> LENGTH: 23
<212> TYPE: DNA
<213> ORGANISM: Artificial Sequence
<220> FEATURE:
<223> OTHER INFORMATION: Synthetic

<400> SEQUENCE: 36
gaacacatcc agaaactgat tgc                                             23

<210> SEQ ID NO 37
<211> LENGTH: 20
<212> TYPE: DNA
<213> ORGANISM: Artificial Sequence
<220> FEATURE:
<223> OTHER INFORMATION: Synthetic

<400> SEQUENCE: 37
ggtgagcgtg aacacaaatc                                                 20

<210> SEQ ID NO 38
<211> LENGTH: 18
<212> TYPE: DNA
<213> ORGANISM: Artificial Sequence
<220> FEATURE:
<223> OTHER INFORMATION: Synthetic

<400> SEQUENCE: 38
gaccaagcaa ccgattca                                                   18

<210> SEQ ID NO 39
<211> LENGTH: 20
<212> TYPE: DNA
<213> ORGANISM: Artificial Sequence
<220> FEATURE:
<223> OTHER INFORMATION: Synthetic

<400> SEQUENCE: 39
acctaattgt tcccgccatt                                                 20

<210> SEQ ID NO 40
<211> LENGTH: 21
<212> TYPE: DNA
<213> ORGANISM: Artificial Sequence
<220> FEATURE:
<223> OTHER INFORMATION: Synthetic

<400> SEQUENCE: 40
catccacacc agttgactct t                                               21
```

<210> SEQ ID NO 41
<211> LENGTH: 23
<212> TYPE: DNA
<213> ORGANISM: Artificial Sequence
<220> FEATURE:
<223> OTHER INFORMATION: Synthetic

<400> SEQUENCE: 41
ttctcctcat tctcaatgtc ctg                                    23

<210> SEQ ID NO 42
<211> LENGTH: 21
<212> TYPE: DNA
<213> ORGANISM: Artificial Sequence
<220> FEATURE:
<223> OTHER INFORMATION: Synthetic

<400> SEQUENCE: 42
cagcaggctg gttcctattt a                                      21

<210> SEQ ID NO 43
<211> LENGTH: 23
<212> TYPE: DNA
<213> ORGANISM: Artificial Sequence
<220> FEATURE:
<223> OTHER INFORMATION: Synthetic

<400> SEQUENCE: 43
ccaacactga ttcaggacca tta                                    23

<210> SEQ ID NO 44
<211> LENGTH: 25
<212> TYPE: DNA
<213> ORGANISM: Artificial Sequence
<220> FEATURE:
<223> OTHER INFORMATION: Synthetic

<400> SEQUENCE: 44
ttctggcgat ctactcaact gtcgc                                  25

<210> SEQ ID NO 45
<211> LENGTH: 26
<212> TYPE: DNA
<213> ORGANISM: Artificial Sequence
<220> FEATURE:
<223> OTHER INFORMATION: Synthetic

<400> SEQUENCE: 45
acaagaccaa tcctgtcacc tctgac                                 26

<210> SEQ ID NO 46
<211> LENGTH: 24
<212> TYPE: DNA
<213> ORGANISM: Artificial Sequence
<220> FEATURE:
<223> OTHER INFORMATION: Synthetic

<400> SEQUENCE: 46
ttaatgagct gccctgtcgg tgaa                                   24

<210> SEQ ID NO 47
<211> LENGTH: 25
<212> TYPE: DNA
<213> ORGANISM: Artificial Sequence
<220> FEATURE:

<223> OTHER INFORMATION: Synthetic

<400> SEQUENCE: 47
tgagaatggg agacctccac tcact                                    25

<210> SEQ ID NO 48
<211> LENGTH: 29
<212> TYPE: DNA
<213> ORGANISM: Artificial Sequence
<220> FEATURE:
<223> OTHER INFORMATION: Synthetic

<400> SEQUENCE: 48
agcctaatca gaccaaatga gaatccagc                                29

<210> SEQ ID NO 49
<211> LENGTH: 26
<212> TYPE: DNA
<213> ORGANISM: Artificial Sequence
<220> FEATURE:
<223> OTHER INFORMATION: Synthetic

<400> SEQUENCE: 49
ctgtcatgga agcaagtact ggcaga                                   26

<210> SEQ ID NO 50
<211> LENGTH: 24
<212> TYPE: DNA
<213> ORGANISM: Artificial Sequence
<220> FEATURE:
<223> OTHER INFORMATION: Synthetic

<400> SEQUENCE: 50
acacgagtgg acaagctgac acaa                                     24

<210> SEQ ID NO 51
<211> LENGTH: 28
<212> TYPE: DNA
<213> ORGANISM: Artificial Sequence
<220> FEATURE:
<223> OTHER INFORMATION: Synthetic

<400> SEQUENCE: 51
acttactcat cgtcaatgat gtgggaga                                 28

<210> SEQ ID NO 52
<211> LENGTH: 20
<212> TYPE: DNA
<213> ORGANISM: Artificial Sequence
<220> FEATURE:
<223> OTHER INFORMATION: Synthetic

<400> SEQUENCE: 52
aaatggacag ggccaaaggt                                          20

<210> SEQ ID NO 53
<211> LENGTH: 20
<212> TYPE: DNA
<213> ORGANISM: Artificial Sequence
<220> FEATURE:
<223> OTHER INFORMATION: Synthetic

<400> SEQUENCE: 53
gacgaaattc aggtcacctc                                          20

```
<210> SEQ ID NO 54
<211> LENGTH: 20
<212> TYPE: DNA
<213> ORGANISM: Artificial Sequence
<220> FEATURE:
<223> OTHER INFORMATION: Synthetic

<400> SEQUENCE: 54
gctgcgaagg gaagaagttt                                              20

<210> SEQ ID NO 55
<211> LENGTH: 20
<212> TYPE: DNA
<213> ORGANISM: Artificial Sequence
<220> FEATURE:
<223> OTHER INFORMATION: Synthetic

<400> SEQUENCE: 55
ctgggtcttc agttaaaggg                                              20

<210> SEQ ID NO 56
<211> LENGTH: 20
<212> TYPE: DNA
<213> ORGANISM: Artificial Sequence
<220> FEATURE:
<223> OTHER INFORMATION: Synthetic

<400> SEQUENCE: 56
cagaactgcg gactcaactc                                              20

<210> SEQ ID NO 57
<211> LENGTH: 20
<212> TYPE: DNA
<213> ORGANISM: Artificial Sequence
<220> FEATURE:
<223> OTHER INFORMATION: Synthetic

<400> SEQUENCE: 57
cccacttcgt tagggaaaac                                              20

<210> SEQ ID NO 58
<211> LENGTH: 20
<212> TYPE: DNA
<213> ORGANISM: Artificial Sequence
<220> FEATURE:
<223> OTHER INFORMATION: Synthetic

<400> SEQUENCE: 58
atgggattcc tcaaggaagg                                              20

<210> SEQ ID NO 59
<211> LENGTH: 20
<212> TYPE: DNA
<213> ORGANISM: Artificial Sequence
<220> FEATURE:
<223> OTHER INFORMATION: Synthetic

<400> SEQUENCE: 59
gtttcaagac acgaggtctc                                              20

<210> SEQ ID NO 60
<211> LENGTH: 20
<212> TYPE: DNA
<213> ORGANISM: Artificial Sequence
<220> FEATURE:
<223> OTHER INFORMATION: Synthetic
```

<400> SEQUENCE: 60
gggtgcattc acaatcagag                                                   20

<210> SEQ ID NO 61
<211> LENGTH: 20
<212> TYPE: DNA
<213> ORGANISM: Artificial Sequence
<220> FEATURE:
<223> OTHER INFORMATION: Synthetic

<400> SEQUENCE: 61
caaatgggtt cagtgggttg                                                   20

<210> SEQ ID NO 62
<211> LENGTH: 20
<212> TYPE: DNA
<213> ORGANISM: Artificial Sequence
<220> FEATURE:
<223> OTHER INFORMATION: Synthetic

<400> SEQUENCE: 62
ctgtatgaac tgctggggaa                                                   20

<210> SEQ ID NO 63
<211> LENGTH: 20
<212> TYPE: DNA
<213> ORGANISM: Artificial Sequence
<220> FEATURE:
<223> OTHER INFORMATION: Synthetic

<400> SEQUENCE: 63
gctcttcaat ggtggaacag                                                   20

<210> SEQ ID NO 64
<211> LENGTH: 20
<212> TYPE: DNA
<213> ORGANISM: Artificial Sequence
<220> FEATURE:
<223> OTHER INFORMATION: Synthetic

<400> SEQUENCE: 64
ctctcggact gacgaaagga                                                   20

<210> SEQ ID NO 65
<211> LENGTH: 20
<212> TYPE: DNA
<213> ORGANISM: Artificial Sequence
<220> FEATURE:
<223> OTHER INFORMATION: Synthetic

<400> SEQUENCE: 65
aagtctaagt ggtcgtggtg                                                   20

<210> SEQ ID NO 66
<211> LENGTH: 20
<212> TYPE: DNA
<213> ORGANISM: Artificial Sequence
<220> FEATURE:
<223> OTHER INFORMATION: Synthetic

<400> SEQUENCE: 66
cagaggactc agcttcaatc                                                   20

<210> SEQ ID NO 67
<211> LENGTH: 20

```
<212> TYPE: DNA
<213> ORGANISM: Artificial Sequence
<220> FEATURE:
<223> OTHER INFORMATION: Synthetic

<400> SEQUENCE: 67
atttggaccg ctgagaacag                                          20

<210> SEQ ID NO 68
<211> LENGTH: 20
<212> TYPE: DNA
<213> ORGANISM: Artificial Sequence
<220> FEATURE:
<223> OTHER INFORMATION: Synthetic

<400> SEQUENCE: 68
tcaaggctgg agaagtttgg                                          20

<210> SEQ ID NO 69
<211> LENGTH: 20
<212> TYPE: DNA
<213> ORGANISM: Artificial Sequence
<220> FEATURE:
<223> OTHER INFORMATION: Synthetic

<400> SEQUENCE: 69
gcattaagca aaacccaggg                                          20

<210> SEQ ID NO 70
<211> LENGTH: 20
<212> TYPE: DNA
<213> ORGANISM: Artificial Sequence
<220> FEATURE:
<223> OTHER INFORMATION: Synthetic

<400> SEQUENCE: 70
gtcttcgagc aggttaacag                                          20

<210> SEQ ID NO 71
<211> LENGTH: 20
<212> TYPE: DNA
<213> ORGANISM: Artificial Sequence
<220> FEATURE:
<223> OTHER INFORMATION: Synthetic

<400> SEQUENCE: 71
tgctagacgg gtgatgaaca                                          20

<210> SEQ ID NO 72
<211> LENGTH: 20
<212> TYPE: DNA
<213> ORGANISM: Artificial Sequence
<220> FEATURE:
<223> OTHER INFORMATION: Synthetic

<400> SEQUENCE: 72
acgcgtttga ggtgatgatg                                          20

<210> SEQ ID NO 73
<211> LENGTH: 20
<212> TYPE: DNA
<213> ORGANISM: Artificial Sequence
<220> FEATURE:
<223> OTHER INFORMATION: Synthetic

<400> SEQUENCE: 73
```

```
tggcgacagt tgagtagatc                                              20

<210> SEQ ID NO 74
<211> LENGTH: 20
<212> TYPE: DNA
<213> ORGANISM: Artificial Sequence
<220> FEATURE:
<223> OTHER INFORMATION: Synthetic

<400> SEQUENCE: 74
gagaccaaaa gcaccagtga                                              20

<210> SEQ ID NO 75
<211> LENGTH: 20
<212> TYPE: DNA
<213> ORGANISM: Artificial Sequence
<220> FEATURE:
<223> OTHER INFORMATION: Synthetic

<400> SEQUENCE: 75
tgtgcgaaca agagctcttg                                              20

<210> SEQ ID NO 76
<211> LENGTH: 20
<212> TYPE: DNA
<213> ORGANISM: Artificial Sequence
<220> FEATURE:
<223> OTHER INFORMATION: Synthetic

<400> SEQUENCE: 76
ttgaaccctg catcagtgag                                              20

<210> SEQ ID NO 77
<211> LENGTH: 20
<212> TYPE: DNA
<213> ORGANISM: Artificial Sequence
<220> FEATURE:
<223> OTHER INFORMATION: Synthetic

<400> SEQUENCE: 77
agatccatac acacaggcag                                              20

<210> SEQ ID NO 78
<211> LENGTH: 20
<212> TYPE: DNA
<213> ORGANISM: Artificial Sequence
<220> FEATURE:
<223> OTHER INFORMATION: Synthetic

<400> SEQUENCE: 78
aatgcagcag aatggcatgc                                              20

<210> SEQ ID NO 79
<211> LENGTH: 20
<212> TYPE: DNA
<213> ORGANISM: Artificial Sequence
<220> FEATURE:
<223> OTHER INFORMATION: Synthetic

<400> SEQUENCE: 79
atgtcaaagg agggcacgat                                              20

<210> SEQ ID NO 80
<211> LENGTH: 20
<212> TYPE: DNA
<213> ORGANISM: Artificial Sequence
```

```
<220> FEATURE:
<223> OTHER INFORMATION: Synthetic

<400> SEQUENCE: 80
ccacggatgg gacaaagaga                                               20

<210> SEQ ID NO 81
<211> LENGTH: 20
<212> TYPE: DNA
<213> ORGANISM: Artificial Sequence
<220> FEATURE:
<223> OTHER INFORMATION: Synthetic

<400> SEQUENCE: 81
cgacagggca gctcattaag                                               20

<210> SEQ ID NO 82
<211> LENGTH: 20
<212> TYPE: DNA
<213> ORGANISM: Artificial Sequence
<220> FEATURE:
<223> OTHER INFORMATION: Synthetic

<400> SEQUENCE: 82
ttgaattgta cggggacgga                                               20

<210> SEQ ID NO 83
<211> LENGTH: 20
<212> TYPE: DNA
<213> ORGANISM: Artificial Sequence
<220> FEATURE:
<223> OTHER INFORMATION: Synthetic

<400> SEQUENCE: 83
cgcgggttgt caccgaaaac                                               20

<210> SEQ ID NO 84
<211> LENGTH: 20
<212> TYPE: DNA
<213> ORGANISM: Artificial Sequence
<220> FEATURE:
<223> OTHER INFORMATION: Synthetic

<400> SEQUENCE: 84
caaggcctca tacagtctag                                               20

<210> SEQ ID NO 85
<211> LENGTH: 20
<212> TYPE: DNA
<213> ORGANISM: Artificial Sequence
<220> FEATURE:
<223> OTHER INFORMATION: Synthetic

<400> SEQUENCE: 85
gtcaatggtg aacggcaact                                               20

<210> SEQ ID NO 86
<211> LENGTH: 20
<212> TYPE: DNA
<213> ORGANISM: Artificial Sequence
<220> FEATURE:
<223> OTHER INFORMATION: Synthetic

<400> SEQUENCE: 86
cggtatcagg gtaacaggaa                                               20
```

```
<210> SEQ ID NO 87
<211> LENGTH: 20
<212> TYPE: DNA
<213> ORGANISM: Artificial Sequence
<220> FEATURE:
<223> OTHER INFORMATION: Synthetic

<400> SEQUENCE: 87
ggcgccttga gtcagaaaaa                                                    20

<210> SEQ ID NO 88
<211> LENGTH: 20
<212> TYPE: DNA
<213> ORGANISM: Artificial Sequence
<220> FEATURE:
<223> OTHER INFORMATION: Synthetic

<400> SEQUENCE: 88
ctgacgggac gatagagaga                                                    20

<210> SEQ ID NO 89
<211> LENGTH: 20
<212> TYPE: DNA
<213> ORGANISM: Artificial Sequence
<220> FEATURE:
<223> OTHER INFORMATION: Synthetic

<400> SEQUENCE: 89
caagtctctg tgcgatctcg                                                    20

<210> SEQ ID NO 90
<211> LENGTH: 20
<212> TYPE: DNA
<213> ORGANISM: Artificial Sequence
<220> FEATURE:
<223> OTHER INFORMATION: Synthetic

<400> SEQUENCE: 90
cacggtgagc gtgaacacaa                                                    20

<210> SEQ ID NO 91
<211> LENGTH: 20
<212> TYPE: DNA
<213> ORGANISM: Artificial Sequence
<220> FEATURE:
<223> OTHER INFORMATION: Synthetic

<400> SEQUENCE: 91
acaaagcgtc tacgctgcag                                                    20

<210> SEQ ID NO 92
<211> LENGTH: 20
<212> TYPE: DNA
<213> ORGANISM: Artificial Sequence
<220> FEATURE:
<223> OTHER INFORMATION: Synthetic

<400> SEQUENCE: 92
tatgagaccg atgctgggag                                                    20

<210> SEQ ID NO 93
<211> LENGTH: 20
<212> TYPE: DNA
<213> ORGANISM: Artificial Sequence
<220> FEATURE:
<223> OTHER INFORMATION: Synthetic
```

<400> SEQUENCE: 93
tgctgcaatg acgagaggat					20

<210> SEQ ID NO 94
<211> LENGTH: 20
<212> TYPE: DNA
<213> ORGANISM: Artificial Sequence
<220> FEATURE:
<223> OTHER INFORMATION: Synthetic

<400> SEQUENCE: 94
atagactctg gcactccttc					20

<210> SEQ ID NO 95
<211> LENGTH: 20
<212> TYPE: DNA
<213> ORGANISM: Artificial Sequence
<220> FEATURE:
<223> OTHER INFORMATION: Synthetic

<400> SEQUENCE: 95
gaagccgatc aaggaatggg					20

<210> SEQ ID NO 96
<211> LENGTH: 20
<212> TYPE: DNA
<213> ORGANISM: Artificial Sequence
<220> FEATURE:
<223> OTHER INFORMATION: Synthetic

<400> SEQUENCE: 96
ttcgatgtcc agaccgagag					20

<210> SEQ ID NO 97
<211> LENGTH: 20
<212> TYPE: DNA
<213> ORGANISM: Artificial Sequence
<220> FEATURE:
<223> OTHER INFORMATION: Synthetic

<400> SEQUENCE: 97
actttctgct tgggcatgag					20

<210> SEQ ID NO 98
<211> LENGTH: 20
<212> TYPE: DNA
<213> ORGANISM: Artificial Sequence
<220> FEATURE:
<223> OTHER INFORMATION: Synthetic

<400> SEQUENCE: 98
caacaattgt cccctcttcg					20

<210> SEQ ID NO 99
<211> LENGTH: 20
<212> TYPE: DNA
<213> ORGANISM: Artificial Sequence
<220> FEATURE:
<223> OTHER INFORMATION: Synthetic

<400> SEQUENCE: 99
gagggcagtg gtgaaatttc					20

<210> SEQ ID NO 100

```
<211> LENGTH: 7
<212> TYPE: PRT
<213> ORGANISM: Simian virus 40

<400> SEQUENCE: 100

Pro Lys Lys Lys Arg Lys Val
1               5

<210> SEQ ID NO 101
<211> LENGTH: 16
<212> TYPE: PRT
<213> ORGANISM: Homo sapiens

<400> SEQUENCE: 101

Lys Arg Pro Ala Ala Thr Lys Lys Ala Gly Gln Ala Lys Lys Lys Lys
1               5                   10                  15

<210> SEQ ID NO 102
<211> LENGTH: 17
<212> TYPE: PRT
<213> ORGANISM: Homo sapien

<400> SEQUENCE: 102

Lys Arg Pro Met Asn Ala Phe Ile Val Trp Ser Arg Asp Gln Arg Arg
1               5                   10                  15

Lys

<210> SEQ ID NO 103
<211> LENGTH: 5
<212> TYPE: PRT
<213> ORGANISM: Homo sapien

<400> SEQUENCE: 103

Arg Pro Arg Arg Lys
1               5

<210> SEQ ID NO 104
<211> LENGTH: 20
<212> TYPE: PRT
<213> ORGANISM: Homo sapien

<400> SEQUENCE: 104

Ser Ser Asn Phe Gly Pro Met Lys Gly Gly Asn Arg Phe Phe Arg Ser
1               5                   10                  15

Ser Gly Pro Tyr
            20

<210> SEQ ID NO 105
<211> LENGTH: 27
<212> TYPE: PRT
<213> ORGANISM: Escherichia coli

<400> SEQUENCE: 105

Arg Ser Gly Gly Asn His Arg Arg Asn Gly Arg Gly Gly Arg Gly Gly
1               5                   10                  15

Tyr Asn Arg Arg Asn Asn Gly Tyr His Pro Tyr
            20                  25

<210> SEQ ID NO 106
<211> LENGTH: 16
<212> TYPE: PRT
<213> ORGANISM: Borna disease virus

<400> SEQUENCE: 106
```

```
Leu Arg Leu Thr Leu Leu Glu Leu Val Arg Arg Leu Asn Gly Asn Gly
1               5                   10                  15

<210> SEQ ID NO 107
<211> LENGTH: 10
<212> TYPE: PRT
<213> ORGANISM: Homo sapien

<400> SEQUENCE: 107

Gly Lys Ile Ser Lys His Trp Thr Gly Ile
1               5                   10

<210> SEQ ID NO 108
<211> LENGTH: 12
<212> TYPE: PRT
<213> ORGANISM: Human immunodeficiency virus type 1

<400> SEQUENCE: 108

Arg Gln Ala Arg Arg Asn Arg Arg Arg Arg Trp Arg
1               5                   10

<210> SEQ ID NO 109
<211> LENGTH: 12
<212> TYPE: PRT
<213> ORGANISM: Human immunodeficiency virus type 1

<400> SEQUENCE: 109

Gly Arg Lys Lys Arg Arg Gln Arg Arg Arg Ala Pro
1               5                   10

<210> SEQ ID NO 110
<211> LENGTH: 18
<212> TYPE: PRT
<213> ORGANISM: Human T-cell lymphotropic virus type 1

<400> SEQUENCE: 110

Met Pro Lys Thr Arg Arg Arg Pro Arg Arg Ser Gln Arg Lys Arg Pro
1               5                   10                  15

Pro Thr
```

US 11,795,456 B2

MRNA DRIVEN EXPRESSION OF RNA EDITORS FOR TREATMENT OF PATHOLOGIES

CROSS-REFERENCE TO RELATED APPLICATIONS

This application claims benefit of and priority to U.S. Provisional Patent Application No. 62/658,046 filed on Apr. 16, 2018, and where permissible is incorporated by reference in its entirety.

STATEMENT REGARDING FEDERALLY SPONSORED RESEARCH

This invention was made with government support under W911NF-15-0609 awarded by DARPA. The government has certain rights in the invention.

REFERENCE TO A SEQUENCE LISTING

The Sequence Listing submitted on Apr. 15, 2019, as a text file named "064489046PCT_ST25" created on Apr. 15, 2019, and having a size of 30,123 bytes is hereby incorporated by reference pursuant to 37 C.F.R. § 1.52(e)(5).

TECHNICAL FIELD OF THE INVENTION

This invention is generally related to compositions that specifically cleave target sequences in viruses, for example RNA viruses.

BACKGROUND OF THE INVENTION

There are 219 species of viruses that are known to infect humans (Woolhouse, M., et al., *Philos Trans R Soc Lond B Biol Sci,* 367:2864-2871 (2012)) of which, 214 are RNA viruses (Woolhouse, M. E. J. and Brierley, L., *Sci Data,* 5:180017 (2018)). It is estimated that viral infections contribute to approximately 6.6% of global mortality (Lozano, R., et al., *Lancet,* 380:2095-2128 (2012)). It is a matter of concern that there are only about 90 drugs (since 1963-2016) to treat only 9 viral species (De Clercq, E. and Li, G., *Clin Microbiol Rev,* 29:695-747 (2016)). Also, there are approved vaccines for only 15 viral species. Reassortment, antigenic shift and drift pose challenges to vaccine development and result in resistance to various antiviral drugs (Kimberlin, D. W. and Whitley, R. J., *J Antimicrob Chemother,* 37:403-421 (1996); Irwin, K. K., et al., *Virus Evol,* 2:vew014 (2016)). These factors contribute to epidemics and pandemics. Human health is thus under constant threat due to emerging and reemerging viral infections (Marston, H. D., et al., *Sci Transl Med,* 6:253ps210 (2014)). Recent outbreaks of Nipah (World Health Organization, Disease outbreak news: Nipah virus-India (2018)), Zika (Baud, D., et al., *Lancet,* 390: 2099-2109 (2017)) and Ebola (Gire, S. K., et al., *Science,* 345:1369-1372 (2014)), and the potential for future influenza pandemics (Neumann, G., et al., *Nature,* 459:931-939 (2009)), warrant the development of new classes of antiviral drugs (De Clercq, E. and Li, G., *Clin Microbiol Rev,* 29:695-747 (2016)).

Current drug development is focused on small molecules and neutralizing antibodies, which require high doses or frequent re-dosing to obtain functional outcomes (Kamath, A. V., *Drug Discov Today Technol,* 21-22:75-83 (2016); Bai, S., et al., *Clin Pharmacokinet,* 51:119-135 (2012)). Thus, it is crucial to address the need for antivirals that are broad spectrum, flexible and effective across multiple viral species or strains. These attributes can be achieved by designing antiviral agents employing genetic tools such as zinc-finger nucleases (Wayengera, M., *Theor Biol Med Model,* 8:23 (2011)), transcription activator-like effector nucleases (Khalili, K., et al., *J Neurovirol,* 21:310-321 (2015)), meganucleases (Grosse, S., et al., *Mol Ther,* 19:694-702 (2011)) and CRISPR-Cas9 (Soppe, J. A., and Lebbink, R. J., *Trends Microbiol,* 25:833-850 (2017)) which have been used against viral infectious agents. These genetic editors have been employed to directly target DNA viruses and indirectly target the viral host to abrogate or modify host genes that are essential for the virus. These tools have also been used to activate or inactivate latent virus that is integrated in the host genome (Soppe, J. A., and Lebbink, R. J., *Trends Microbiol,* 25:833-850 (2017)). These molecular tools are suitable for DNA viruses but harnessing them against RNA viruses has been less effective.

Therefore it is an object of the invention to provide compositions and methods of their use for the inhibition of viral replication.

It is another object of the invention to provide compositions and methods of their use for the treatment or inactivation of viruses in a host cell or subject.

SUMMARY OF THE INVENTION

Compositions and methods for the treatment and inactivation of viruses from a host cell or a subject are provided herein. The compositions and methods can be used to remove viral or other foreign genetic material from a host organism, without interfering with the integrity of the host's genetic material.

An exemplary composition for inactivating RNA viruses in vitro or in vivo includes an isolated nucleic acid sequence encoding an RNA-guided endonuclease, and at least one guide RNA (gRNA), wherein the gRNA is complementary to a target nucleic acid sequence in an RNA-viral genome. In one embodiment, the isolated nucleic acid construct is an mRNA construct. The mRNA construct can include modifications, for example, a nuclear localization sequence, a 5' cap, a 3' Poly(A) tail, or modified nucleobases such as N1-Methylpseudouridine-5'-Triphosphate, 2'-O-Methyladenosine-5'-Triphosphate, or 2'-O-Methyluridine-5'-Triphosphate, or combinations thereof. In some embodiments, the RNA-guided endonuclease is an RNA-guided RNase. The RNA-guided RNase can be a Cas nuclease, for example Cas13a.

In one embodiment, the disclosed compositions can be used to treat RNA viruses such as an influenza virus or respiratory syncytial virus. The RNA viruses can be negative-strand RNA viruses or positive-strand RNA viruses.

In some embodiments, the isolated nucleic acid sequence has a sequence according to SEQ ID NO:1. In another embodiment, the isolated nucleic acid sequence has a sequence according to SEQ ID NO:2.

Also provided are pharmaceutical compositions including the disclosed isolated nucleic acid sequence encoding an RNA-guided endonuclease, at least one guide RNA (gRNA), and a pharmaceutically acceptable carrier.

Methods of using the disclosed compositions are also provided. One embodiment provides a method of treating a viral infection in a subject in need thereof by administering to the subject a pharmaceutical composition including at least isolated nucleic acid sequence encoding an RNA-guided endonuclease and at least one guide RNA (gRNA), wherein the gRNA is complementary to a target nucleic acid sequence in an RNA-viral genome, in an amount effective to inhibit viral replication in the subject. The RNA-guided endonuclease can be Cas13a and the guide RNA construct can target a viral gene. In one embodiment the viral gene is neuraminidase (NA), hemagglutinin (HA), ion channel (M2), matrix protein (M1), nucleocapsid protein (NP), nuclear export protein (NS1 and NS2) or RNA polymerase PB1, PB2, or PA.

BRIEF DESCRIPTION OF THE DRAWINGS

FIG. 1A is a schematic representation of RNA cleavage assay using in vitro translation of Cas13a and Cas13a-NLS. In vitro transcribed mRNA expressing either Cas13a or Cas13a-NLS was translated in vitro using rabbit reticulocyte translation system. In vitro translated product was mixed with crRNAs, their corresponding target RNAs and an RNase alert substrate, which fluoresces upon cleavage, owing to RNase activity. FIGS. 1B and 1C are bar graphs showing target specific RNA cleavage of Cas13a (FIG. 1B) and Cas13a-NLS (FIG. 1C) using crRNA (CR) targeting PB1 gene of influenza virus (gPB1) and its specific target RNA (TR). A non-target crRNA (NT-CR) was used a negative control. The RNA cleavage activity of Cas13a was measured at room temperature, for 90 minutes using mock translated product as a blank control. Mean RFU is represented as a means of triplicates. FIGS. 1D and 1E are representative images of denaturing gels demonstrating RNA cleavage activity of Cas13a (FIG. 1D) and Cas13a-NLS (FIG. 1E) against PB1 gene in the presence or absence of the corresponding CR and TRs.

FIGS. 2A-2K are line graphs showing RNA cleavage activity of Cas13a against influenza genes gPB1 (FIG. 2A), PB1_4.1 (FIG. 2B), HA1.1 (FIG. 2C), NA1.1 (FIG. 2D), NP1.1 (FIG. 2E), PB2_1.1 (FIG. 2F), NN2_1.1 (FIG. 2G), MM1.1 (FIG. 2H), PB1_2.1 (FIG. 2I), PB1_3.1 (FIG. 2J), and non-target controls (FIG. 2K).

FIGS. 3A-3H are representative images of denaturing gels demonstrating RNA cleavage activity of crRNAs against various IVA gene fragments in the presence or absence of their corresponding trRNAs. The boxes and arrows represent degraded RNA.

FIG. 4A is a schematic representation of the mechanism of IVA RNA cleavage by Cas13a and/or Cas13a-NLS. FIGS. 4B-4K are fluorescence microscopy images showing expression kinetics of Cas13 and Cas13a-NLS in A549 cells using Viromer Red. Cas13 is stained using the V5 tag and nuclei are stained with DAPI.

FIGS. 5A-5JJ are fluorescence microscopy images showing expression kinetics of Cas13a in MDCK and A549 cells using Neon electroporation (FIGS. 5A-5L), Viromer Red (FIGS. 5M-5X), and Lipofectamine 3000 (FIGS. 5Y-5JJ). Cells were transfected with 1 μg of Cas13a mRNA. Cells were fixed at 2, 4, 6, 16, or 24 hours and stained with anti-V5 and DAPI nuclear stain. Scale bars=20 μm.

FIG. 6A is a schematic of experimental set-up to test IVA inhibition in A549 cells in FIGS. 6B-6E. FIG. 6B is a bar graph showing PB1 gene copies that were quantified to determine the RNA cleavage activity of Cas13a and Cas13a-NLS with various crRNAs (gPB1, PB1_2.1, PB1_3.1 and PB1_4.1) targeting PB1 IVA genes in vitro (A549 cells).

FIG. 6C is a bar graph showing RNA cleavage activity of Cas13a and Cas13a-NLS using non-PB1 gene targeting crRNA (HA1.1, NA1.1, NP1.1, NN2.1 and MM2.1) on PB1 gene.

FIGS. 6D-6E are bar graphs showing comparisons of all crRNA targeting different IVA segments, represented as percent reduction in comparison to respective IVA genes targeting crRNA. All data points are mean of three replicates (n=3) and error bars represent standard deviation. (*$p \leq 0.05$, $p \leq 0.005$, *$p \leq 0.001$ or **$p \leq 0.0001$). For multiple comparisons, either Tukey's multiple comparison test (FIGS. 6B and 6C) or Sidak's multiple comparisons test (FIGS. 6D and 6**E) were applied.

FIGS. 7A-7H are representative fluorescence microscopy images showing Cas13a and Cas13a-NLS inhibit IVA infection in cells transfected with mRNA encoding either proteins and crRNA for IVA gene PB1 genomic (gPB1) and messenger (mPB1) RNA, for 4 h before infection. Cells transfected and infected were stained for IVA M2 protein, FISH targeting IVA, Cas13a V5 and nuclei.

FIG. 8A is a schematic of experimental set-up to optimize Cas13a:crRNA doses and viral infections. FIG. 8B is a bar graph showing dose response assay of Cas13a and crRNA on IVA titers. FIGS. 8C and 8D are bar graphs showing the effect of Cas13a and gPB1 on IVA at MOI 0.01 (FIG. 8C) and MOI 0.1 (FIG. 8D).

FIG. 9 is a bar graph showing PB1 copy number in human primary bronchial/tracheal epithelial cells transfected with Cas13a (1 μg) and crRNA gPB1 and/or mPB1 (100 nM) and subsequently infected with IVA.

FIG. 10A is a schematic of experimental set-up to test IVA inhibition in A549 cells. FIGS. 10B-10C are bar graphs showing PB1 gene copy number over time in cells transfected with either Cas13a (FIG. 10B) or Cas13a-NLS (FIG. 10C), and crRNAs targeting IVA PB1 gene (gPB1 and mPB1). FIG. 10D is a schematic of experimental set-up to test IVA inhibition in infected A549 cells. FIGS. 10E-10F are bar graphs showing PB1 gene copy number over time in cells transfected with either Cas13a (FIG. 10E) or Cas13a-NLS (FIG. 10F), and crRNAs targeting IVA PB1 gene (gPB1 and mPB1). FIG. 10G is a schematic of experimental set up of delayed infection assay. FIG. 10H is a bar graph showing PB1 gene copy number in a delayed infection model. Cells were transfected with Cas13 and CR gPB1 and mPB1 for 24 h and then infected with IVA for 8 h. FIG. 10I is a schematic of experimental set-up, when the A549 cells were infected with IVA (MOI 0.01) for 24 h and later transfected with Cas13a and crRNA (gPB1 and mPB1). FIG. 10J is a bar graph showing PB1 gene copy number in cells were infected with IVA (MOI 0.01) for 24 h and later transfected with Cas13a and crRNA (gPB1 and mPB1). All data points are mean of three replicates (n=3) and error bars represent standard deviation. All the statistical analyses were performed using analysis of variance with multiple comparisons with appropriate post-test measurements (for b-c and e-f, Ordinary two-way ANOVA with Tukey's multiple comparisons test, and for H and J, one way ANOVA with Dunnett's multiple comparisons test). (*$p \leq 0.05$, $p \leq 0.005$, *$p \leq 0.001$ or ****$p \leq 0.0001$).

FIG. 11A is a schematic of experimental set-up to test RSV inhibition prophylactically in A549 cells. FIG. 11B is a bar graph showing plaque formation in cells infected with RSV after Cas13a transfection. FIG. 11C is a schematic of experimental set-up to test RSV inhibition post-infection in A549 cells. FIG. 11D is a bar graph showing plaque formation in cells infected with RSV before Cas13a transfection. All data points are mean of three replicates (n=3) and error bars represent standard deviation. Statistical analyses were performed using analysis of variance with Tukey's multiple comparisons test (* $p \leq 0.05$, $p \leq 0.005$, *$p \leq 0.001$ or ****$p \leq 0.0001$).

FIGS. 12A-12L are transcriptome profile of cells transfected with Cas13a mRNA and crRNA (PB1) at 8 and 24h post-delivery, with or without infection with IVA.

DETAILED DESCRIPTION OF THE INVENTION

I. Definitions

It should be appreciated that this disclosure is not limited to the compositions and methods described herein as well as the experimental conditions described, as such may vary. It is also to be understood that the terminology used herein is for the purpose of describing certain embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any compositions, methods and materials similar or equivalent to those described herein can be used in the practice or testing of the present invention. All publications mentioned are incorporated herein by reference in their entirety.

The use of the terms "a," "an," "the," and similar referents in the context of describing the presently claimed invention (especially in the context of the claims) are to be construed to cover both the singular and the plural, unless otherwise indicated herein or clearly contradicted by context.

Recitation of ranges of values herein are merely intended to serve as a shorthand method of referring individually to each separate value falling within the range, unless otherwise indicated herein, and each separate value is incorporated into the specification as if it were individually recited herein.

Use of the term "about" is intended to describe values either above or below the stated value in a range of approx. +/−10%; in other embodiments the values may range in value either above or below the stated value in a range of approx. +/−5%; in other embodiments the values may range in value either above or below the stated value in a range of approx. +/−2%; in other embodiments the values may range in value either above or below the stated value in a range of approx. +/−1%. The preceding ranges are intended to be made clear by context, and no further limitation is implied. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

As used herein, an "RNA" refers to a ribonucleic acid that may be naturally or non-naturally occurring. For example, an RNA may include modified and/or non-naturally occurring components such as one or more nucleobases, nucleosides, nucleotides, or linkers. An RNA may include a cap structure, a chain terminating nucleoside, a stem loop, a polyA sequence, and/or a polyadenylation signal. An RNA may have a nucleotide sequence encoding a polypeptide of interest. For example, an RNA may be a messenger RNA (mRNA). Translation of an mRNA encoding a particular polypeptide, for example, in vivo translation of an mRNA inside a mammalian cell, may produce the encoded polypeptide.

The terms "polypeptide", "peptide", and "protein", may be used interchangeably to refer a string of at least three amino acids linked together by peptide bonds. Peptide may refer to an individual peptide or a collection of peptides. Peptides can contain natural amino acids, non-natural amino acids (i.e., compounds that do not occur in nature but that can be incorporated into a polypeptide chain), and/or amino acid analogs. Also, one or more of the amino acids in a peptide may be modified, for example, by the addition of a chemical entity such as a carbohydrate group, a phosphate group, a farnesyl group, an isofarnesyl group, a fatty acid group, a linker for conjugation, functionalization, or other modification, etc. Modifications may include cyclization of the peptide, the incorporation of D-amino acids, etc.

The term "percent (%) sequence identity" is defined as the percentage of nucleotides or amino acids in a candidate sequence that are identical with the nucleotides or amino acids in a reference nucleic acid sequence, after aligning the sequences and introducing gaps, if necessary, to achieve the maximum percent sequence identity. Alignment for purposes of determining percent sequence identity can be achieved in various ways that are within the skill in the art, for instance, using publicly available computer software such as BLAST, BLAST-2, ALIGN, ALIGN-2 or Megalign (DNASTAR) software. Appropriate parameters for measuring alignment, including any algorithms needed to achieve maximal alignment over the full-length of the sequences being compared can be determined by known methods.

For purposes herein, the % sequence identity of a given nucleotides or amino acids sequence C to, with, or against a given nucleic acid sequence D (which can alternatively be phrased as a given sequence C that has or comprises a certain % sequence identity to, with, or against a given sequence D) is calculated as follows:

$$100 \text{ times the fraction } W/Z,$$

where W is the number of nucleotides or amino acids scored as identical matches by the sequence alignment program in that program's alignment of C and D, and where Z is the total number of nucleotides or amino acids in D. It will be appreciated that where the length of sequence C is not equal to the length of sequence D, the % sequence identity of C to D will not equal the % sequence identity of D to C.

"Genome editing" refers to a type of genetic engineering in which DNA is inserted, deleted, modified, or replaced in the genome of a living organism. It is a way of making specific changes to the DNA of a cell or organism. One of the most widely used types of genome editing is engineered nuclease genome editing. The engineered nucleases are enzymes that make cuts at specific sites in a DNA sequence, when these cuts are repaired by the cell a change is introduced into the sequence. Exemplary types of engineered nucleases include but are not limited to CRISPR/Cas, zinc-finger nucleases (ZFN), and transcription activator-like effector nucleases (TALEN).

As used herein, the term "CRISPRs" or "Clustered Regularly Interspaced Short Palindromic Repeats" refers to an acronym for DNA loci that contain multiple, short, direct repetitions of base sequences. Each repetition contains a series of bases followed by the same series in reverse and then by approximately 30 base pairs known as "spacer DNA". The spacers are short segments of DNA that are often derived from a bacterial virus or other foreign genetic element and may serve as a 'memory' of past exposures to facilitate an adaptive defense against future invasions.

"CRISPR-associated nuclease" or "Cas" refers to an enzyme that cuts DNA at a specific location in the genome so that nucleotide bases can then be added or removed.

"Guide RNA" or "gRNA" refers to a specific RNA sequence that recognizes the target DNA region of interest and directs Cas nuclease there for editing.

As used herein, the terms "treat," "treating," "treatment" and "therapeutic use" refer to the elimination, reduction or amelioration of one or more symptoms of a disease or disorder. As used herein, a "therapeutically effective amount" refers to that amount of a therapeutic agent sufficient to mediate a clinically relevant elimination, reduction or amelioration of such symptoms. An effect is clinically relevant if its magnitude is sufficient to impact the health or prognosis of a recipient subject. A therapeutically effective amount may refer to the amount of therapeutic agent sufficient to delay or minimize the onset of disease, e.g., delay or minimize the spread of cancer. A therapeutically effective amount may also refer to the amount of the therapeutic agent that provides a therapeutic benefit in the treatment or management of a disease.

As used herein, the term "prophylactic agent" refers to an agent that can be used in the prevention of a disorder or disease prior to the detection of any symptoms of such disorder or disease. A "prophylactically effective" amount is the amount of prophylactic agent sufficient to mediate such protection. A prophylactically effective amount may also refer to the amount of the prophylactic agent that provides a prophylactic benefit in the prevention of disease.

As used herein, the terms "individual," "host," "subject," and "patient" are used interchangeably herein, and refer to a mammal, including, but not limited to, humans, rodents, such as mice and rats, and other laboratory animals.

As used herein, the term "pharmaceutically acceptable carrier" encompasses any of the standard pharmaceutical carriers, such as a phosphate buffered saline solution, water and emulsions such as an oil/water or water/oil emulsion, and various types of wetting agents.

As used herein, "positive-strand RNA virus" or "sense-strand RNA virus" is a virus whose genetic information consists of a single strand of RNA that is the positive (or sense) strand which encodes mRNA (messenger RNA) and protein.

As used herein, "negative-strand RNA virus" or "anti-sense-strand RNA virus" is a virus whose genetic information consists of a single strand of RNA that is the negative or antisense strand which does not encode mRNA (messenger RNA).

The term "inactivation" of virus, as used herein, means that that virus is unable to replicate, the genome is deleted, fragmented, degraded, genetically inactivated, or any other physical, biological, chemical or structural manifestation that prevents the virus from being transmissible or infecting any other cell or subject resulting in the clearance of the virus in vivo. In some cases, fragments of the viral genome may be detectable, however, the virus is incapable of replication, or infection.

The term "target nucleic acid" sequence refers to a nucleic acid to which the oligonucleotide is designed to specifically hybridize. It is either the presence or absence of the target nucleic acid that is to be detected, or the amount of the target nucleic acid that is to be quantified. The target nucleic acid has a sequence that is complementary to the nucleic acid sequence of the corresponding oligonucleotide directed to the target.

II. Compositions for Inhibiting Viral Replication

Compositions for the treatment or inactivation of viruses in a host cell or subject are provided herein. Exemplary compositions include nucleic acids encoding an RNA-guided endonuclease and a guide RNA that is complementary to a target sequence in a virus. In one embodiment, the RNA-guided endonuclease specifically targets viral nucleic acid sequences for destruction and suppression of that virus in a host cell in vitro or in vivo. Any suitable nuclease systems can be used including, for example, clustered regularly interspaced short palindromic repeat (CRISPR) nucleases, zinc-finger nucleases (ZFNs), transcription activator-like effector nucleases (TALENs), meganucleases, other endo- or exo-nucleases, or combinations thereof. In one embodiment, the nuclease system is CRISPR/Cas.

A. RNA-Guided Endonuclease

The disclosed compositions include a nucleic acid construct encoding an RNA-guided endonuclease. In one embodiment, the nucleic acid construct is an mRNA construct. In some embodiments, the RNA-guided endonuclease is a CRISPR-associated endonuclease. CRISPR systems employ a nuclease called CRISPR-associated (Cas) that complexes with small RNAs as guides (gRNAs) to cleave DNA in a sequence-specific manner upstream of the protospacer adjacent motif (PAM) in any genomic location. CRISPR may use separate guide RNAs known as the crRNA and tracrRNA. These two separate RNAs have been combined into a single RNA to enable site-specific mammalian genome cutting through the design of a short guide RNA. Cas and guide RNA (gRNA) may be synthesized by known methods. Cas/guide-RNA (gRNA) uses a non-specific DNA cleavage protein Cas, and an RNA oligonucleotide to hybridize to target and recruit the Cas/gRNA complex (Chang et al., Cell Res. 23:465-472 (2013); Hwang et al., Nat. Biotechnol., 31:227-229 (2013)).

CRISPR systems include two classes that are subdivided into five types and sixteen subtypes. In some embodiments, the CRISPR/Cas system can be a type II or type IV system. Non-limiting examples of suitable CRISPR/Cas proteins include Cas3, Cas4, Cas5, Cas5e (or CasD), Cash, Case, Cas6f, Cas7, Cas8a1, Cas8a2, Cas8b, Cas8c, Cas9, Cas10, Cas10d, CasF, CasG, CasH, Csy1, Csy2, Csy3, Cse1 (or CasA), Cse2 (or CasB), Cse3 (or CasE), Cse4 (or CasC), Csc1, Csc2, Csa5, Csn2, Csm2, Csm3, Csm4, Csm5, Csm, Cmr1, Cmr3, Cmr4, Cmr5, Cmr6, Csb1, Csb2, Csb, Csx17, Csx14, Csx10, Csx16, CsaX, Csx3, Csz1, Csx15, Csf1, Csf2, Csf3, Csf4, and Cu1966.

In one embodiment, the RNA-guided endonuclease is derived from a type II CRISPR/Cas system. The CRISPR associated endonuclease, Cas9, belongs to the type II CRISPR/Cas system and has strong endonuclease activity to cut target DNA. Cas9 is guided by a mature crRNA that contains about 20 base pairs (bp) of unique target sequence (called spacer) and a trans-activated small RNA (tracrRNA) that serves as a guide for ribonuclease III-aided processing of pre-crRNA. The crRNA:tracrRNA duplex directs Cas9 to target DNA via complementary base pairing between the spacer on the crRNA and the complementary sequence (called protospacer) on the target DNA. Cas9 recognizes a trinucleotide (NGG) protospacer adjacent motif (PAM) to specify the cut site (the 3rd nucleotide from PAM). The crRNA and tracrRNA can be expressed separately or engineered into an artificial fusion small guide RNA (sgRNA) via a synthetic stem loop (AGAAAU) to mimic the natural crRNA/tracrRNA duplex. Such sgRNA, like shRNA, can be synthesized or in vitro transcribed for direct RNA transfection or expressed from U6 or H1-promoted RNA expression vector, although cleavage efficiencies of the artificial sgRNA are lower than those for systems with the crRNA and tracrRNA expressed separately.

In one embodiment, the RNA-guided endonuclease is a type VI RNase such as Cas13a, Cas13b, Cas13c or Cas13d. In one embodiment, the RNA-guided endonuclease is Cas13a. Cas13 enzymes are RNA-guided RNA endonucleases associated with the CRISPR adaptive immunity system in prokaryotes. Cas13 nucleases function similarly to Cas9, using a ~64-nt guide RNA to encode target specificity. The Cas13 protein complexes with the guide RNA via recognition of a short hairpin in the crRNA, and target specificity is encoded by a 28-30-nt spacer that is complementary to the target region. In addition to programmable RNase activity, all Cas13 nucleases exhibit collateral activity after recognition and cleavage of a target transcript, leading to non-specific degradation of any nearby transcripts regardless of complementarity to the spacer. Exemplary bacteria that express Cas13 nucleases include but are not limited to *Leptotrichia wadei*, *Leptotrichia shahii*, *Leptotricia oral* taxon, *Leptotricia buccalis*, *Lachnospiraceae bacterium*, *Eubacterium rectale*, *Clostridium aminophilum*, *Herbinix hemicellulosilytica*, *Rhodobacter capsulatus*, *Paludibacter propionicigenes*, *Carnobacterium gallinarum*, *Listeria seeligeri*, and *Listeria newyorkensis*. In one embodiment, the Cas13 enzyme is Cas13a from *Leptotricia wadei*, *Leptotricia shahii*, *Leptotricia oral* taxon, or *Leptotricia buccalis*.

In certain embodiments, the RNA-guided endonucleases comprise at least one RNA recognition and/or RNA binding domain. RNA recognition and/or RNA binding domains interact with guide RNAs. RNA-guided endonucleases can also comprise nuclease domains (i.e., DNase or RNase domains), DNA binding domains, helicase domains, RNase domains, protein-protein interaction domains, dimerization domains, as well as other domains.

In some embodiments, the RNA-guided endonucleases can be a wild type RNA-guided endonuclease, a modified RNA-guided endonuclease, or a fragment of a wild type or modified RNA-guided endonuclease. The RNA-guided endonuclease can be modified to increase nucleic acid binding affinity and/or specificity, alter an enzymatic activity, and/or change another property of the protein. For example, nuclease (i.e., DNase, RNase) domains of RNA-guided endonucleases can be modified, deleted, or inactivated. Alternatively, the RNA-guided endonuclease can be truncated to remove domains that are not essential for the function of the fusion protein. The RNA-guided endonuclease can also be truncated or modified to optimize the activity of the effector domain of the fusion protein.

In some embodiments, the RNA-guided endonucleases can be derived from a wild type Cas13 protein or fragment thereof. In other embodiments, the RNA-guided endonucleases can be derived from modified Cas13 protein. For example, the amino acid sequence of the Cas13 protein can be modified to alter one or more properties (e.g., nuclease activity, affinity, stability, etc.) of the protein. Alternatively, domains of the Cas13 protein not involved in RNA-guided cleavage can be eliminated from the protein such that the modified Cas13 protein is smaller than the wild type Cas13 protein.

In one embodiment the nucleic acid construct encoding an RNA-guided endonuclease is an mRNA construct.

In one embodiment, the Cas13a encoding nucleic acid construct has the following nucleic acid sequence:

(SEQ ID NO: 1)
ttttaagcttTAATACGACTCACTATAGGGAAATAAGAGAGAAAAGAAGA

GTAAGAAGAAATATAAGAGCCACCatgaaagtgacgaaggtaggaggcat ttcgcataagaagtacacgtccgaaggccgcttagtgaagtcagaatcgg aagaaaatcgcacagacgaacgtctgtcggcgttgcttaatatgcgcctt gacatgtatatcaagaatcccagcagcacggaaaccaaggaaaatcaaaa acgcattgggaaattaaagaaattcttctcaaacaaaatggtctatctta aagacaataccttgagtttgaagaatgggaaaaaggagaacattgatcgt gagtattctgagactgacatccttgagagcgatgtccgtgacaagaaaaa cttcgccgtgttgaaaaagatctatctgaatgaaaacgtgaactcggagg aattggaagttttcgtaacgacattaagaagaaactgaacaaaatcaac agcctgaagtactcatttgaaaagaataaggcgaattatcaaaagattaa tgagaataacatcgagaaggttgaaggtaagtcaaagcgtaacattattt acgattattatcgtgagtcagcgaaacgtgacgcttatgtaagcaatgtg aaagaagcctttgataagctttacaaggaagaggacattgcaaaacttgt tcttgaaattgagaaccttacgaagttagagaaatacaagattcgcgagt tctaccacgaaattattggacgtaagaatgacaaggaaaactttgcaaaa atcatctacgaagaaatccagaatgttaataacatgaaagagttgatcga gaaggtaccggacatgagtgagttgaaaaagagccaagtattttacaagt attacttagacaaagaagagttgaacgacaagaacatcaaatacgcgttt tgtcatttcgtggaaatcgaaatgagtcagttgctgaagaactacgtata taagcgcttaagtaatatctcgaatgacaaaattaagcgtatctttgaat accagaacttgaaaaaattgatcgaaaataagctgttaaacaaacttgac acgtacgtccgtaattgtggaaagtataattattatttgcaagacggcga aattgccacttcagatttcatcgcccgcaaccgtcagaatgaagcgtttc ttcgcaacatcattgggtgtcatctgtggcctacttttctcttcgcaac attcttgaaacggagaacgagaatgatattactgggcgtatgcgcggcaa aacagttaagaacaataaaggtgaagagaagtacgtgtccggagaagttg ataagatctataatgaaaataagaagaacgaggttaaggagaacttaaaa atgttctattcgtacgatttcaatatggacaacaagaatgaaatcgaaga tttcttcgccaacatcgacgaggcgatttcttccatccgtcacggtattg tccacttcaacttggaattagaaggtaaggatatctttgcgttcaagaac attgcgccatccgaaatctcaaagaagatgtttcagaatgagattaacga gaaaaactgaaattgaagatctttcgtcaactgaactctgccaacgtgt tccgctatctcgaaaagtataaaattctgaattaccttaaacgtacacgc ttcgagtttgtcaataaaaatatcccattcgtcccgtctttcaccaaatt atattcgcgcattgatgacctgaagaatagtcttgggatttactggaaaa ctccgaaaacaaacgacgacaataagactaaggagattattgatgcccaa atctatttgcttaaaaacatctattacggggagttcctgaattatttcat gtcgaacaatggtaatttctttgagatttctaaagaaatcatcgaattga acaagaacgataaacgcaacttaaagactgggttttacaagctgcaaaag tttgaagacatccaggagaagattccaaaggaatacttggcgaatatcca -continued gtccctgtacatgattaatgccggtaatcaggacgaagaagaaaaggaca cttatattgatttcattcaaaagatcttcttaaagggatttatgacgtat cttgctaataacggtcgtttaagtctgatttacatcggctcggatgaaga aacaaatacgtcattagcagaaaagaagcaagagtttgacaagttcttga agaagtacgagcagaacaataatatcaagatcccctatgagatcaatgaa ttcctgcgtgagatcaaactgggaaacatcctgaagtatactgagcgttt aaacatgttctaccttatcttaaagcttttgaatcacaaggagctgacaa atctgaagggtagtcttgaaaaatatcagtctgccaataaggaagaagcg ttctctgaccaattggagttaattaacctgcttaaccttgacaacaaccg cgtgacggaagacttcgaattagaggccgacgagattggaaaatttcttg atttcaatggcaacaaagttaaggataacaaggaactgaaaaagttcgat acaaacaagatctactttgacggcgagaacattatcaaacaccgtgcctt ctacaatattaagaaatatggcatgttaaacttactggagaaaattgccg acaaggctggatacaagatctcgatcgaagagctgaagaaatactccaat aaaaagaatgagatcgagaagaaccataagatgcaggaaaatctgcaccg caaatacgctcgtccccgtaaagacgagaagtttacagatgaggactatg aaagttacaagcaagctattgagaatattgaggagtacacccaccttaag aacaaggtagaattcaatgagctgaatttactgcagggcctgttgctgcg cattttacatcgtttagtcggatatacctcaatttgggaacgcgatctgc gcttccgccttaaaggtgagttcccagaaaaccaatacatcgaagagatc ttcaactttgaaaataagaagaacgtgaagtacaaagggggtcagattgt agagaaatacattaaattctacaaggaattacatcaaaatgatgaagtta agatcaacaagtacagttccgcgaatatcaaggtgttgaagcaagaaaag aaggacctttatattcgaaattacatcgcccacttcaattatattcctca cgccgagatctcactgctggaagtccttgaaaatttgcgtaaattgctgt cctacgatcgcaaactgaaaaatgccgtaatgaaatcagtagttgatatc cttaaggagtatggttttgtagccacattcaaaatcggggcggacaagaa gatcggtattcagacactggagagcgaaaaaatcgtgcatcttaagaatc ttaagaagaagaagttaatgactgaccgcaattccgaggaactttgcaaa ttggtgaagattatgtttgaatacaaaatggaagagaaaaagtctgaaaa <u>c</u>GGTAAGCCTATCCCTAACCCTCTCCTCGGTCTCGATTCTACGTGATAAg ctgccttctgcggggcttgccttctggccatgcccttcttctctcccttg cacctgtacctcttggtctttgaataaagcctgagtaggaaggcggccgc aaaaa The underlined sequence represents the restriction site, the bolded, uppercase sequence represents the 5' UTR, and the double-underlined sequence represents the coding region.

In another embodiment, the Cas13a encoding nucleic acid construct includes a nuclear localization sequence and has a nucleic acid sequence as follows:

(SEQ ID NO: 2)
GCGGAAGGCCGTCAAGGCCGCATTTTTAAGCTTTAATACGACTCACTATA

GGGAAATAAGAGAGAAAAGAAGAGTAAGAAGAAATATAAGAGCCACCATG

CCCAAAAAGAAGAGGAAAGTGGGATCCATGAAAGTGACCAAAGTCGGCGG

CATCAGCCACAAGAAGTACACCTCTGAGGGCAGACTGGTCAAGAGCGAGA

GCGAGGAAACCGGACCGACGAGAGACTGAGCGCCCTGCTGAACATGCGG

CTGGACATGTACATCAAGAACCCCAGCAGCACCGAGACAAAAGAGAACCA

GAAGCGGATCGGCAAGCTGAAGAAGTTCTTTAGCAACAAGATGGTGTACC

TGAAGGACAACACCCTGAGCCTGAAGAACGGCAAGAAAGAGAACATCGAC

CGCGAGTACAGCGAGACAGACATCCTGGAAAGCGACGTGCGGGACAAGAA

AAACTTCGCCGTGCTGAAGAAAATCTACCTGAACGAGAACGTGAACAGCG

AGGAACTGGAAGTGTTCCGCAACGATATCAAGAAGAAGCTGAACAAGATC

AACAGCCTGAAGTACAGCTTCGAGAAGAACAAGGCCAACTACCAGAAGAT

CAACGAGAACAACATCGAGAAGGTGGAAGGCAAGAGCAAGCGGAACATCA

TCTACGACTACTACAGAGAGAGCGCCAAGCGGGACGCCTACGTGTCCAAT

GTGAAAGAGGCCTTCGACAAGCTGTACAAAGAGGAAGATATCGCCAAGCT

GGTGCTCGAGATCGAGAACCTGACCAAGCTGGAAAAGTACAAGATCCGCG

AGTTCTACCACGAGATCATCGGCCGGAAGAACGACAAAGAGAACTTCGCC

AAGATCATCTATGAAGAGATCCAGAACGTCAACAACATGAAGGAACTGAT

TGAGAAGGTGCCCGACATGAGCGAGCTGAAAAAGTCCCAGGTGTTCTACA

AGTACTACCTGGACAAAGAAGAATTGAACGACAAGAATATTAAGTACGCC

TTCTGCCACTTCGTGGAAATCGAGATGAGCCAGCTGCTGAAAAACTACGT

GTACAAGCGGCTGAGCAACATCAGCAACGATAAGATCAAGCGGATCTTCG

AGTACCAGAACCTGAAGAAGCTCATTGAGAACAAGCTGCTCAACAAGCTC

GACACCTACGTGCGGAACTGCGGCAAGTACAACTACTATCTGCAAGACGG

CGAGATCGCCACCAGCGACTTTATCGCCCGGAACAGACAGAACGAGGCCT

TCCTGAGAAACATCATCGGCGTGTCCAGCGTGGCCTACTTCAGCCTGCGG

AACATTCTGGAAACCGAGAACGAGAATGACATCACCGGCCGGATGAGAGG

CAAGACCGTGAAAAACAACAAGGGCGAAGAGAAATACGTGTCCGGCGAGG

TGGACAAGATCTACAATGAGAACAAAAAGAACGAAGTGAAAGAAAACCTC

AAGATGTTCTACAGCTACGACTTCAACATGGACAACAAGAATGAGATCGA

GGACTTCTTCGCCAACATCGACGAGGCCATCAGCAGCATCAGACACGGCA

TCGTGCACTTCAACCTCGAGCTGGAAGGGAAAGACATCTTCGCCTTCAAG

AATATCGCCCCTAGCGAGATCAGCAAGGAAGATGTTCCAGAACGAGATCAA

TGAGAAGAAACTGAAGCTCAAGATCTTCCGGCAGCTGAACAGCGCCAACG

TGTTCAGATACCTCGAGAAGTATAAGATCCTGAACTACCTGAAGCGGACC

CGCTTCGAGTTCGTGAACAAGAACATCCCCTTCGTGCCCAGCTTCACCAA

GCTGTATAGCCGGATCGACGATCTGAAGAACAGCCTGGGCATCTACTGGA

AAACCCCTAAGACCAACGACGATAACAAGACCAAAGAGATCATTGACGCC

CAGATCTACCTCCTCAAGAATATCTACTACGGCGAGTTCCTGAATTACTT

CATGAGCAACAACGGCAACTTCTTCGAGATCTCCAAAGAAATCATCGAAC

TCAACAAGAACGATAAGCGGAACCTGAAAACCGGCTTCTACAAGCTGCAG

AAATTCGAGGACATCCAAGAGAAGATCCCCAAAGAGTACCTGGCCAACAT

CCAGAGCCTGTACATGATCAACGCCGGCAACCAGGACGAGGAAGAGAAGG

-continued

```
ACACCTACATCGACTTTATTCAGAAGATTTTCCTGAAGGGCTTCATGACC
TACCTGGCTAACAACGGCCGGCTGTCCCTGATCTACATCGGCAGCGACGA
GGAAACAAACACCAGCCTGGCCGAGAAAAAGCAAGAGTTCGACAAGTTCC
TTAAGAAGTACGAGCAGAACAACAACATCAAGATCCCGTACGAGATTAAC
GAGTTCCTCCGCGAGATCAAGCTGGGGAACATCCTCAAGTACACCGAGCG
GCTGAATATGTTCTACCTGATCCTGAAACTGCTGAACCACAAAGAGCTGA
CCAATCTGAAGGGAAGCCTCGAGAAATACCAGTCCGCCAACAAAGAAGAG
GCCTTTAGCGACCAGCTGGAACTGATCAACCTGCTGAATCTCGACAACAA
CAGAGTGACCGAGGACTTTGAACTCGAGGCCGACGAGATCGGAAAGTTCC
TGGACTTCAATGGCAACAAAGTGAAGGATAACAAAGAACTCAAGAAGTTC
GATACCAACAAAATCTACTTCGACGGGGAGAATATCATCAAGCACCGGGC
CTTCTACAACATTAAGAAATACGGCATGCTGAACCTGCTCGAGAAGATCG
CCGATAAGGCCGGCTACAAGATCAGCATTGAGGAACTGAAGAAATACTCC
AACAAGAAGAACGAGATTGAGAAGAACCACAAGATGCAAGAGAACCTGCA
CCGGAAGTACGCCAGACCTCGGAAGGACGAGAAGTTCACCGACGAGGATT
ACGAGAGCTACAAGCAGGCCATCGAGAATATCGAAGAGTACACCCACCTC
AAGAACAAAGTGGAATTCAACGAGCTGAATCTGCTGCAGGGCCTGCTGCT
GAGAATCCTGCATAGACTCGTGGGCTACACCAGCATCTGGGAGCGCGACC
TGAGATTCAGACTGAAGGGCGAGTTTCCCGAGAACCAGTACATCGAGGAA
ATCTTCAACTTCGAAAACAAAAAAAACGTGAAGTACAAAGGCGGCCAGAT
CGTTGAGAAGTACATTAAGTTCTACAAAGAATTGCACCAGAACGACGAAG
TCAAGATTAACAAGTACAGCAGCGCCAATATCAAGGTGCTGAAGCAAGAG
AAAAAGGACCTGTACATCCGGAACTATATCGCCCACTTCAACTACATCCC
TCACGCCGAGATTAGCCTGCTGGAAGTGCTGGAAAATCTGCGGAAGCTGC
TGAGCTACGACCGGAAACTGAAAAACGCCGTGATGAAGTCCGTGGTGGAT
ATCCTGAAAGAATACGGCTTCGTGGCCACCTTCAAGATCGGAGCCGACAA
GAAGATCGGCATCCAGACACTGGAATCCGAAAAGATCGTGCACCTGAAAA
ATCTGAAAAAGAAAAAGCTGATGACCGACCGGAACTCCGAAGAACTGTGC
AAGCTCGTGAAGATCATGTTCGAGTACAAAATGGAAGAAAAGAAATCCGA
GAACGGATCCGGTAAGCCTATCCCTAACCCTCTCCTCGGTCTCGATTCTA
CGGGATCCCCCAAGAAAAGCGCAAGGTATGATAAGCTGCCTTCTGCGGG
GCTTGCCTTCTGGCCATGCCCTTCTTCTCTCCCTTGCACCTGTACCTCTT
GGTCTTTGAATAAAGCCTGAGTAGGAAGGCGGCCGCAAAAACTGGGCCTC
ATG
```

Nucleic acids 1-27 of SEQ ID NO:2 represent the 5' pMA7 vector sequence, nucleic acids 28-33 of SEQ ID NO:2 represent HindIII restriction site, nucleic acids 34-53 of SEQ ID NO:2 represent T7 promoter, nucleic acids 54-97 of SEQ ID NO:2 represent 5' UTR, nucleic acids 101-121 of SEQ ID NO:2 represent SV40 nuclear localization sequence (NLS), nucleic acids 122-127 of SEQ ID NO:2 represent GS linker, nucleic acids 128-3604 of SEQ ID NO:2 represent Lbu Cas13a codon optimized, nucleic acids 3605-3610 of SEQ ID NO:2 represent GS linker, nucleic acids 3611-3652 of SEQ ID NO:2 represent V5 tag, nucleic acids 3653-3658 of SEQ ID NO:2 represent GS linker, nucleic acids 3659-3679 of SEQ ID NO:2 represent SV40 NLS, nucleic acids 3680-33685 represent stop codon, nucleic acids 3686-3778 represent 3' UTR, nucleic acids 3779-3786 represent NotI restriction site, and nucleic acids 3787-3803 of SEQ ID NO:2 represent 3' pMA7 vector sequence.

In one embodiment, the nucleic acid construct encoding an RNA-guided endonuclease has a nucleic acid sequence having at least 70, 75, 80, 85, 90, 95, 96, 97, 98, 99, or 100% sequence identity to SEQ ID NO:1. In another embodiment, the nucleic acid construct encoding an RNA-guided endonuclease has a nucleic acid sequence having at least 70, 75, 80, 85, 90, 95, 96, 97, 98, 99, or 100% sequence identity to SEQ ID NO:2.

1. Modifications

The disclosed nucleic acid constructs encoding an RNA-guided endonuclease can be modified to increase stability and reduce immunogenicity. In one embodiment, the nucleic acid construct encoding an RNA-guided endonuclease is modified to alter the delivery target, for example through the addition of a nuclear localization sequence to the nucleic acid construct. Exemplary nuclear localization sequences include but are not limited to simian virus 40 (SV40) large T antigen (PKKKRKV) (SEQ ID NO:100), nucleoplasmin (KRPAATKKAGQAKKKK) (SEQ ID NO:101), SRY (KRPMNAFIVWSRDQRRK) (SEQ ID NO:102) and RPRRK (SEQ ID NO:103), hnRNP A1 (SSNFGPMKGG-NRFFRSSGPY) (SEQ ID NO:104), Hrp1 (RSGGNHRRN-GRGGRGGYNRRNNGYHPY) (SEQ ID NO:105), BDV p10 (LRLTLLELVRRLNGNG) (SEQ ID NO:106), PLSCR1 (GKISKHWTGI) (SEQ ID NO:107), HIV-1 Rev (RQARRNRRRRWR) (SEQ ID NO:108), HIV-1 Tat (GRKKRRQRRRAP) (SEQ ID NO:109), HTLV-1 Rex (MPKTRRRPRRSQRKRPPT) (SEQ ID NO:110).

Naturally occurring mRNAs bear a cap structure at the 5' end and a long sequence of polyadenylate residue (Poly(A) tail) at the 3' end that are added after transcription of the DNA. Synthetic mRNAs without modifications do not have a cap on the 5' end or a Poly(A) tail on the 3' end. In one embodiment, the nucleic acid constructs encoding an RNA-guided endonuclease are modified with a 5' cap structure and a 3' Poly(A) tail to increase stability and reduce immunogenicity. The 5' cap can be a 7-methylguanosine cap, including variations such as Cap 0, Cap 1, Cap 2, Cap 3, or Cap 4, or LNA modified Cap analogues. The poly(A) tail can be added to the 3'UTR to protect the mRNA from nuclease degradation. In one embodiment, the poly(A) tail has 25-1000 nucleotides. In another embodiment, the poly(A) tail has 100, 150, 200, 250, 300, 350, 400, 450, 500, 550, or 1000 nucleotides.

Naturally occurring RNAs are synthesized from four basic ribonucleotides: ATP, CTP, UTP, and GTP. In one embodiment, the nucleic acid constructs encoding an RNA-guided endonuclease can include modifications to the ribonucleotides. Suitable modifications include alterations in one or more nucleotides of a codon such that the codon encodes the same amino acid but is more stable than the codon found in the wild-type version of the nucleic acid. For example, an inverse relationship between the stability of RNA and a higher number cytidines (C's) and/or uridines (U's) residues has been demonstrated, and RNA devoid of C and U residues have been found to be stable to most RNases. In some embodiments, the number of C and/or U residues in an mRNA sequence is reduced. In another embodiment, the number of C and/or U residues is reduced by substitution of one codon encoding a particular amino acid for another codon encoding the same or a related amino acid. Contemplated modifications to the mRNA nucleic acids of the present invention also include the incorporation of pseudouridines. The incorporation of pseudouridines into the mRNA nucleic acids may enhance stability and translational capacity, as well as diminishing immunogenicity in vivo.

In another embodiment, the disclosed nucleic acid constructs encoding an RNA-guided endonuclease contain post-transcriptionally modified nucleotides. In one embodiment, the incorporation of modified nucleosides can increase stability and reduce immunogenicity of the mRNA construct. In one embodiment, cytidine and/or uridine are replaced by modified nucleosides. Exemplary modified nucleoside bases include but are not limited to 5-methylcytidine, 2'-O-methylcytidine, pseudouridine, $N^6$-methyladenosine, $N^6$,2'-O-dimethyladenosine, $N^6$,$N^6$,2'-O-trimethyladenosine, 3,2'-O-dimethyluridine, 7-methylguanosine, 2'-O-methylguanosine, $N^2$,7-dimethylguanosine, $N^2$,$N^2$,7-trimethylguanosine. In one embodiment, the synthetic mRNA is incorporated with N1-Methylpseudouridine-5'-Triphosphate, 2'-O-Methyladenosine-5'-Triphosphate, or 2'-O-Methyluridine-5'-Triphosphate.

In one embodiment, the nucleic acid construct encoding an RNA-guided endonuclease is optimized by the incorporation of 5'- and 3'-terminal untranslated regions (UTRs) such as alpha- and beta-globin UTRs. Terminal UTRs enhance the RNA stability and translational capacity. 3' or 5' sequences from any native mRNA molecule which are stable (e.g., globin, actin, GAPDH, tubulin, histone, citric acid cycle enzymes) as well as viral RNA, such as alphaviruses, etc. can be incorporated into the 3' and/or 5' region of a the nucleic acid molecule to increase the stability of the nucleic acid construct.

B. Guide RNA

Guide RNA sequences according to the present invention can be sense or anti-sense sequences. The guide RNA sequence generally includes a proto-spacer adjacent motif (PAM). The sequence of the PAM can vary depending upon the specificity requirements of the CRISPR endonuclease used. In the CRISPR-Cas system derived from *S. pyogenes*, the target DNA typically immediately precedes a 5'-NGG proto-spacer adjacent motif (PAM). Thus, for the *S. pyogenes* Cas9, the PAM sequence can be AGG, TGG, CGG or GGG. The specific sequence of the guide RNA may vary, but, regardless of the sequence, useful guide RNA sequences will be those that minimize off-target effects while achieving a high efficiency and complete ablation of the virus, for example, influenza virus. The length of the guide RNA sequence can vary from about 20 to about 60 or more nucleotides, for example about 20, about 21, about 22, about 23, about 24, about 25, about 26, about 27, about 28, about 29, about 30, about 31, about 32, about 33, about 34, about 35, about 36, about 37, about 38, about 39, about 40, about 45, about 50, about 55, about 60 or more nucleotides.

The guide RNA sequence can be configured as a single sequence or as a combination of one or more different sequences, for example, a multiplex configuration. Multiplex configurations can include combinations of two, three, four, five, six, seven, eight, nine, ten, or more different guide RNAs. Accordingly, in some embodiments, a polynucleotide sequence encoding at least one gRNA may encode two distinct gRNA sequences. In other embodiments, one polynucleotide encodes for one gRNA; a second polynucleotide encodes for a second gRNA; a third polynucleotide encodes for a third gRNA, etc., wherein each gRNA is complementary to distinct sequences of a target nucleic acid sequence. In other embodiments, a polynucleotide sequence encodes for two or more distinct gRNA sequences. In other embodiments, a polynucleotide encodes multiple gRNA sequences having overlapping target nucleic acid sequences.

A CRISPR/Cas gene editing complex of the invention works optimally with a guide RNA that targets the viral genome. Guide RNA (gRNA) can include but is not limited to single guide RNA (sgRNA), crisprRNA (crRNA), trans-activating RNA (tracrRNA), any other targeting oligonucleotide, or any combination thereof gRNA leads the CRISPR/Cas complex to the viral genome in order to cause viral genomic disruption. In one embodiment, CRISPR/Cas/gRNA complexes are designed to target a virus, for example an RNA virus, within a cell. It should be appreciated that any virus can be targeted using the composition of the invention. Identification of specific regions of the virus genome aids in development and designing of CRISPR/Cas/gRNA complexes. In one embodiment, the CRISPR/Cas/gRNA complexes are designed to target active viruses within a cell. In another embodiment, the CRISPR/Cas/gRNA complexes are designed to target latent viruses within a cell. Once transfected within a cell, the CRISPR/Cas/gRNA complexes cause repeated insertions or deletions to render the viral genome incapacitated, or due to number of insertions or deletions, the probability of repair is significantly reduced.

The disclosed compositions may include a sequence encoding a guide RNA that is complementary to a target sequence in an RNA-virus, for example influenza viruses or respiratory syncytial virus. Influenza A, influenza B and influenza C viruses are the only members of the Influenza virus A, Influenza virus B and Influenza virus C genera, respectively. These viruses are membrane-enclosed viruses whose genomes are segmented negative-sense (i.e. minus) strands of RNA ((−)RNA). The ten influenza virus genes are present on eight segments of the single-stranded RNA of strains A and B, and on seven segments of strain C. The segments vary in size (from 890 to 2341 nucleotides in length) and each is a template for synthesis of different mRNAs. The influenza virus virion contains virus-specific RNA polymerases necessary for mRNA synthesis from these templates and, in the absence of such specific polymerases, the minus strand of influenza virus RNA is not infectious. Initiation of transcription of the mRNAs occurs when the influenza virus mRNA polymerase takes 12 to 15 nucleotides from the 5' end of a cellular mRNA or mRNA precursor and uses the borrowed oligonucleotide as a primer. This process has been termed "cap-snatching" because it places a 5' cap structure on the viral mRNA. Generally, the mRNAs made through this process encode only one protein. The M gene and NS gene viral RNA segments also code for spliced mRNAs, which results in production of two different proteins for each of these two segments. Replication of influenza viral RNA occurs in the nucleus and involves the synthesis of three different species of RNA.

After infection of a naive cell, the minus strand virion RNA (VRNA) is transported to the nucleus where RNA destined for translation (mRNA) is synthesized using 5'-terminal 10-13 nucleotide primers cleaved by viral-encoded enzymes from capped cellular pre-mRNA molecules (i.e. cap-snatching). Synthesis of each mRNA continues to near the end of the genome segment where an oligo(U) stretch is encountered and a poly(A)tail is added. The dedicated viral mRNAs are transported to the cytoplasm for translation and after sufficient viral proteins are transported back into the nucleus, synthesis of VRNA destined for nascent virions is initiated. An exact antigenomic copy of VRNA is synthesized (termed cRNA) which is a perfect complement of the genomic VRNA and serves as a template for production of new VRNA.

In one embodiment, the virus is influenza A. Influenza A is a segmented RNA virus of negative-polarity. Genome segments are replicated by a complex of 4 proteins: the 3 polymerase polypeptides (PA, PB1 and PB2) and NP (Nucleoprotein). The 5' and 3' terminal sequence regions of all 8 genome segments are highly conserved within a genotype. Influenza A viruses can be subtyped according to the antigenic and genetic nature of their surface glycoproteins; 15 hemagglutinin (HA) and 9 neuraminidase (NA) subtypes have been identified to date. Viruses bearing all known HA and NA subtypes have been isolated from avian hosts, but only viruses of the H1N1 (1918), H2N2 (1957/58), and H3N2 have caused human epidemics.

In one embodiment, the guide RNA is designed to target genes that are involved in viral replication. Viral polymerases play a central role in viral genome replication and transcription. Exemplary viral components that are necessary for viral replication include but are not limited to the viral nucleoprotein, RNA polymerase, and phosphoproteins. In one embodiment, the guide RNA targets influenza virus neuraminidase (NA), hemagglutinin (HA), ion channel (M2), matrix protein (M1), nucleocapsid protein (NP), nuclear export protein (NS1 and NS2) or RNA polymerase PB1, PB2, or PA. In one embodiment, the guide RNA targets influenza virus A PB1. In another embodiment, the guide RNA targets hRSV. In another embodiment the guide RNA targets the genome of any RNA virus, including filoviruses, flaviviruses, picornaviruses, caliciviruses, togaviruses, arenaviruses, orthormyxoviruses, paramyxoviruses, bunyaviruses, coronaviruses, astroviruses, retroviruses, etc., and can target the mRNA from any virus with either a DNA or RNA genome.

In some embodiments, a mixture of guide RNAS may be introduced into a cell. The guide RNAs are designed to target numerous categories of sequences of the viral genome. By targeting several areas along the genome, the double strand break at multiple locations fragments the genome, lowering the possibility of repair. Even with repair mechanisms, the large deletions render the virus incapacitated.

In some embodiments, several guide RNAs are added to create a mixture to target different categories of sequences. For example, two, five, seven or eleven guide RNAs may be present in a CRISPR mixture targeting three different categories of sequences. However, any number of gRNAs may be introduced into a mixture to target categories of sequences. In preferred embodiments, the categories of sequences are important for genome structure, host cell transformation, and infection latency, respectively.

C. Pharmaceutical Compositions

Pharmaceutical compositions including the disclosed nucleic acids encoding an RNA-guided endonuclease and a guide RNA that is complementary to a target sequence in a virus are provided. Pharmaceutical compositions containing the disclosed compositions can be for administration by parenteral (intramuscular, intraperitoneal, intravenous (IV) or subcutaneous injection), transdermal (either passively or using iontophoresis or electroporation), or transmucosal (nasal, vaginal, rectal, or sublingual) routes of administration or using bioerodible inserts and can be formulated in dosage forms appropriate for each route of administration. In one embodiment, the nucleic acids encoding an RNA-guided endonuclease and the guide RNA are included in the same pharmaceutical composition. In another embodiment, the nucleic acids encoding an RNA-guided endonuclease and the guide RNA are formulated in separate pharmaceutical compositions.

In some in vivo approaches, the compositions disclosed herein are administered to a subject in a therapeutically effective amount. The precise dosage will vary according to a variety of factors such as subject-dependent variables (e.g., age, immune system health, etc.), the disease, and the treatment being effected.

For the disclosed compositions, as further studies are conducted, information will emerge regarding appropriate dosage levels for treatment of various conditions in various patients, and the ordinary skilled worker, considering the therapeutic context, age, and general health of the recipient, will be able to ascertain proper dosing. The selected dosage depends upon the desired therapeutic effect, on the route of administration, and on the duration of the treatment desired. For the disclosed activatable nuclease compositions, generally dosage levels of 0.001 to 20 mg/kg of body weight daily are administered to mammals. Generally, for intravenous injection or infusion, dosage may be lower.

1. Formulations for Parenteral Administration

In some embodiments, compositions disclosed herein, including those containing nucleic acids encoding an RNA-guided endonuclease and guide RNA, are administered in an aqueous solution, by parenteral injection. The formulation may also be in the form of a suspension or emulsion. In general, pharmaceutical compositions are provided including effective amounts of an activatable nuclease composition, and optionally include pharmaceutically acceptable diluents, preservatives, solubilizers, emulsifiers, adjuvants and/or carriers. Such compositions optionally include one or more of the following: diluents, sterile water, buffered saline of various buffer content (e.g., Tris-HCl, acetate, phosphate), pH and ionic strength; and additives such as detergents and solubilizing agents (e.g., TWEEN 20 (polysorbate-20), TWEEN 80 (polysorbate-80)), anti-oxidants (e.g., ascorbic acid, sodium metabisulfite), and preservatives (e.g., Thimersol, benzyl alcohol) and bulking substances (e.g., lactose, mannitol). Examples of non-aqueous solvents or vehicles are propylene glycol, polyethylene glycol, vegetable oils, such as olive oil and corn oil, gelatin, and injectable organic esters such as ethyl oleate. The formulations may be lyophilized and redissolved/resuspended immediately before use. The formulation may be sterilized by, for example, filtration through a bacteria retaining filter, by incorporating sterilizing agents into the compositions, by irradiating the compositions, or by heating the compositions.

2. Formulations for Oral Administration

In some embodiments the compositions are formulated for oral delivery. Oral solid dosage forms are described generally in Remington: The Science and Practice of Pharmacy, 21st Ed. 2006 (Lippincott Williams and Wilkins, Baltimore, Md.) at Chapter 45. Solid dosage forms include tablets, capsules, pills, troches or lozenges, cachets, pellets, powders, or granules or incorporation of the material into particulate preparations of polymeric compounds such as polylactic acid, polyglycolic acid, etc. or into liposomes. Such compositions may influence the physical state, stability, rate of in vivo release, and rate of in vivo clearance of the disclosed. The compositions may be prepared in liquid form, or may be in dried powder (e.g., lyophilized) form. Liposomal or proteinoid encapsulation may be used to formulate the compositions. Liposomal encapsulation may be used and the liposomes may be derivatized with various polymers (e.g., U.S. Pat. No. 5,013,556). In general, the formulation will include the peptide (or chemically modified forms thereof) and inert ingredients which protect peptide in the stomach environment, and release of the biologically active material in the intestine.

The agents can be chemically modified so that oral delivery of the derivative is efficacious. Generally, the chemical modification contemplated is the attachment of at least one moiety to the component molecule itself, where the moiety permits uptake into the blood stream from the stomach or intestine, or uptake directly into the intestinal mucosa. Also desired is the increase in overall stability of the component or components and increase in circulation time in the body. PEGylation is an exemplary chemical modification for pharmaceutical usage. Other moieties that may be used include: propylene glycol, copolymers of ethylene glycol and propylene glycol, carboxymethyl cellulose, dextran, polyvinyl alcohol, polyvinyl pyrrolidone, polyproline, poly-1,3-dioxolane and poly-1,3,6-tioxocane [see, e.g., Abuchowski and Davis (1981) "Soluble Polymer-Enzyme Adducts," in Enzymes as Drugs. Hocenberg and Roberts, eds. (Wiley-Interscience: New York, N.Y.) pp. 367-383; and Newmark, et al. (1982) *J. Appl. Biochem.* 4:185-189].

Another embodiment provides liquid dosage forms for oral administration, including pharmaceutically acceptable emulsions, solutions, suspensions, and syrups, which may contain other components including inert diluents; adjuvants such as wetting agents, emulsifying and suspending agents; and sweetening, flavoring, and perfuming agents.

Controlled release oral formulations may be desirable. The agent can be incorporated into an inert matrix which permits release by either diffusion or leaching mechanisms, e.g., gums. Slowly degenerating matrices may also be incorporated into the formulation. Another form of a controlled release is based on the Oros therapeutic system (Alza Corp.), i.e., the drug is enclosed in a semipermeable membrane which allows water to enter and push drug out through a single small opening due to osmotic effects.

For oral formulations, the location of release may be the stomach, the small intestine (the duodenum, the jejunum, or the ileum), or the large intestine. In some embodiments, the release will avoid the deleterious effects of the stomach environment, either by protection of the agent (or derivative) or by release of the agent (or derivative) beyond the stomach environment, such as in the intestine. To ensure full gastric resistance a coating impermeable to at least pH 5.0 is essential. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D™, Aquateric™, cellulose acetate phthalate (CAP), Eudragit L™, Eudragit S™, and Shellac™. These coatings may be used as mixed films.

3. Formulations for Topical Administration

The disclosed compositions can be applied topically. Formulations for topical administration include but are not limited to aerosol delivery, skin patches, topical gels or lotions.

Compositions can be delivered to the lungs while inhaling and traverse across the lung epithelial lining to the blood stream when delivered either as an aerosol or spray dried particles having an aerodynamic diameter of less than about 5 microns.

A wide range of mechanical devices designed for pulmonary delivery of therapeutic products can be used, including but not limited to nebulizers, metered dose inhalers, and powder inhalers, all of which are familiar to those skilled in the art. Some specific examples of commercially available devices are the Ultravent nebulizer (Mallinckrodt Inc., St. Louis, Mo.); the Acorn II nebulizer (Marquest Medical Products, Englewood, Colo.); the Ventolin metered dose inhaler (Glaxo Inc., Research Triangle Park, N.C.); and the Spinhaler powder inhaler (Fisons Corp., Bedford, Mass.). Nektar, Alkermes and Mannkind all have inhalable insulin powder preparations approved or in clinical trials where the technology could be applied to the formulations described herein.

Formulations for administration to the mucosa will typically be spray dried drug particles, which may be incorporated into a tablet, gel, capsule, suspension or emulsion. Standard pharmaceutical excipients are available from any formulator.

Transdermal formulations may also be prepared. These will typically be ointments, lotions, sprays, or patches, all of which can be prepared using standard technology. Transdermal formulations may require the inclusion of penetration enhancers.

4. Controlled Delivery Polymeric Matrices

The compositions disclosed herein can also be administered in controlled release formulations. Controlled release polymeric devices can be made for long term release systemically following implantation of a polymeric device (rod, cylinder, film, disk) or injection (microparticles). The matrix can be in the form of microparticles such as microspheres, where the agent is dispersed within a solid polymeric matrix or microcapsules, where the core is of a different material than the polymeric shell, and the peptide is dispersed or suspended in the core, which may be liquid or solid in nature. Unless specifically defined herein, microparticles, microspheres, and microcapsules are used interchangeably. Alternatively, the polymer may be cast as a thin slab or film, ranging from nanometers to four centimeters, a powder produced by grinding or other standard techniques, or even a gel such as a hydrogel.

Either non-biodegradable or biodegradable matrices can be used for delivery of fusion polypeptides or nucleic acids encoding the fusion polypeptides, although in some embodiments biodegradable matrices are preferred. These may be natural or synthetic polymers, although synthetic polymers are preferred in some embodiments due to the better characterization of degradation and release profiles. The polymer is selected based on the period over which release is desired. In some cases linear release may be most useful, although in others a pulse release or "bulk release" may provide more effective results. The polymer may be in the form of a hydrogel (typically in absorbing up to about 90% by weight of water), and can optionally be crosslinked with multivalent ions or polymers.

The matrices can be formed by solvent evaporation, spray drying, solvent extraction and other methods known to those skilled in the art. Bioerodible microspheres can be prepared using any of the methods developed for making microspheres for drug delivery, for example, as described by Mathiowitz and Langer, *J. Controlled Release*, 5:13-22 (1987); Mathiowitz, et al., *Reactive Polymers*, 6:275-283 (1987); and Mathiowitz, et al., *J. Appl. Polymer Sci.*, 35:755-774 (1988).

The devices can be formulated for local release to treat the area of implantation or injection—which will typically deliver a dosage that is much less than the dosage for treatment of an entire body—or systemic delivery. These can be implanted or injected subcutaneously, into the muscle, fat, or swallowed.

III. Methods of Use

The disclosed compositions and methods can be used for the treatment and inactivation of viruses from a host cell or a subject. Methods of the invention may be used to remove viral or other foreign genetic material from a host organism, without interfering with the integrity of the host's genetic material. A nuclease may be used to target viral nucleic acid, thereby interfering with viral replication or transcription or even excising the viral genetic material from the host genome. The nuclease may be specifically targeted to remove only the viral nucleic acid without acting on host material either when the viral nucleic acid exists as a particle within the cell or when it is integrated into the host genome. Targeting the viral nucleic acid can be done using a sequence-specific moiety such as a guide RNA that targets viral genomic material for destruction by the nuclease and does not target the host cell genome. In some embodiments, a CRISPR/Cas nuclease and guide RNA (gRNA) that together target and selectively edit or destroy viral genomic material is used. The CRISPR is a naturally-occurring element of the bacterial immune system that protects bacteria from phage infection. The guide RNA localizes the CRISPR/Cas complex to a viral target sequence. Binding of the complex localizes the Cas endonuclease to the viral genomic target sequence causing breaks in the viral genome. Other nuclease systems can be used including, for example, zinc finger nucleases, transcription activator-like effector nucleases (TALENs), meganucleases, or any other system that can be used to degrade or interfere with viral nucleic acid without interfering with the regular function of the host's genetic material.

The compositions may be used to target viral nucleic acid in any form or at any stage in the viral life cycle. The targeted viral nucleic acid may be present in the host cell as independent particles. In a preferred embodiment, the viral infection is latent and the viral nucleic acid is integrated into the host genome. Any suitable viral nucleic acid may be targeted for cleavage and digestion.

In certain embodiments, a method of treating or inactivating a virus in a cell or a subject includes contacting the cell or administering to the subject, a pharmaceutical composition including a therapeutically effective amount of a nucleic acid construct encoding a RNA-guided endonuclease and at least one guide RNA having complementarity to a target nucleic acid sequence in a viral genome.

In other embodiments, a method of inhibiting replication of a virus in a cell or a subject includes contacting the cell or administering to the subject, a pharmaceutical composition including a therapeutically effective amount of an isolated nucleic acid sequence encoding an RNA-guided endonuclease and at least one guide RNA having complementarity to a target nucleic acid sequence in a viral genome.

In one embodiment, the disclosed nucleic acid constructs encoding an RNA-guided endonuclease are not activated until they are administered to the subject and the nucleic acid is translated into the nuclease. In one embodiment, the nucleic acid is an mRNA. mRNA has the advantage of rapid translation of the desired protein and rapid clearance, while it avoids safety concerns such as genome integration, vertical and horizontal transmission, and long term persistence in the body.

The nucleic acid construct encoding a RNA-guided endonuclease and the guide RNA construct can be delivered simultaneously or successively. In one embodiment, the nucleic acid construct encoding a RNA-guided endonuclease and the guide RNA construct are delivered simultaneously in the same pharmaceutical composition. In another embodiment, the nucleic acid construct encoding a RNA-guided endonuclease and the guide RNA construct are administered simultaneously in separate pharmaceutical compositions. In yet another embodiment, the nucleic acid construct encoding a RNA-guided endonuclease and the guide RNA construct are administered successively. The nucleic acid construct encoding a RNA-guided endonuclease construct can be administered 1, 2, 3, 4, 5, 6, 7, 8, 12 or 24 hours before the guide RNA construct.

In one embodiment, the disclosed compositions can be administered to the subject once daily, twice daily, or three times daily. In another embodiment, the composition is administered to the subject one a week, twice a week, or three times a week.

A. Diseases to be Treated

1. Viral Infection

The disclosed compositions can be used to reduce viral load in subjects that have been infected with a virus. In one embodiment, the disclosed compositions are administered to the subject having a viral infection in an amount effective to reduce the viral load. The nucleic acid construct encoding a RNA-guided endonuclease and the guide RNA construct can be administered simultaneously in the same pharmaceutical compositions or in two separate compositions. In another embodiment, the nucleic acid construct encoding a RNA-guided endonuclease and the guide RNA construct are administered successively in two separate compositions. In one embodiment, the subject is administered the activatable nuclease composition for 1, 2, 3, 4, 5, 6, 7, 8, or more than 8 weeks. The subject can be administered the activatable nuclease composition until a viral titer shows that the viral load of the subject is within a range that indicates the subject is no longer infected.

The disclosed compositions can be used prophylactically. In one embodiment, the disclosed compositions are administered to subjects who have been potentially exposed to a virus but do not show symptoms of the virus, for example subjects that live in an area having a viral outbreak or epidemic. In such an embodiment, the subject is administered a pharmaceutical composition including the disclosed compositions in an amount effective to prevent the subject from contracting the virus. In one embodiment, the composition is administered to the subject for the duration of the viral outbreak. The composition can be administered to the subject once daily, twice daily, or three times daily. In another embodiment, the composition is administered to the subject one a week, twice a week, or three times a week.

a. RNA Viruses

One embodiment provides methods of treating or reducing viral infection in a subject in need thereof. In one embodiment, the disclosed compositions can be used to treat RNA viruses. Exemplary methods include administering to the subject in need thereof a composition including a nucleic acid construct encoding a RNA-guided endonuclease, and a guide RNA having a sequence that targets an RNA viral gene. Exemplary RNA viruses that cause disease in humans include but are not limited to West Nile virus, Ebola virus, human immunodeficiency virus (HIV), dengue virus, yellow fever virus, influenza virus, Lassa virus, Hantavirus, Marburg virus, Hendra virus, Nipha virus, Chikungunya virus, adenovirus, human monkeypox virus, hepatitis C virus, Rift valley virus, respiratory syncytial virus, and enterovirus.

One embodiment provides a method of treating viruses with plus-strand RNA. Viruses with plus-strand RNA can use their genome directly as mRNA with translation by the host ribosome occurring as soon as the unsegmented viral genome gains entry into the cell. One of the viral genes expressed yields an RNA-dependent RNA-polymerase (or RNA replicase), which creates minus-strand RNA from the plus-strand genome. The minus-strand RNA can be used as a template for more plus-strand RNA, which can be used as mRNA or as genomes for the newly forming viruses. In one embodiment, the guide RNA construct targets the viral gene for RNA replicase.

In another embodiment, the disclosed activatable nucleases can be used to treat negative-strand RNA viruses. Negative-strand RNA viruses include many members, such as influenza virus, rabies virus, and Ebola virus. Since the genome of negative-strand RNA viruses cannot be used directly as mRNA, the virus must carry an RNA-dependent RNA-polymerase within its capsid. Upon entrance into the host cell, the plus-strand RNAs generated by the polymerase are used as mRNA for protein production. In one embodiment, the guide RNA is designed to target the genomic RNA (negative strands), positive strand intermediates, or messenger RNA of viruses.

b. DNA Viruses

In another embodiment, the disclosed compositions can be used to treat or prevent DNA viruses. Exemplary DNA viruses include but are not limited to human papillomavirus (HPV), hepatitis B, adenovirus, herpesvirus, poxvirus, Varicella Zoster virus, and parvovirus. DNA viruses are composed of a set of DNA genes protected by a protein containing coat called a capsid. The capsid protects the DNA genes upon entry into the host. On invasion of a susceptible cell the virion is disassembled to release the viral genome into the cell, at which time the genes within the viral DNA are transcribed, producing viral messenger ribonucleic acid (mRNA). The mRNA is translated into protein which are responsible for altering the normal cellular functions of the host. In one embodiment, the disclosed nucleic acid construct encoding a RNA-guided endonuclease targets the mRNA of the DNA viruses before it is translated into protein.

EXAMPLES

Example 1. Cas13a Cleaves RNA in Presence of Both crRNA and Target RNA

Materials and Methods:

Design and synthesis of Cas13a constructs: Cas from *Leptotrichia buccalis* sequence was obtained from Addgene p2CT-His-MBP-Lbu_C2C2_WT (Plasmid #83482). Wild type Cas13a was cloned with a V5 tag and 3' UTR from mouse alpha-globin was appended (Genbank accession #NM_001083955) in pMA7 vector (Thermo Scientific, USA). A nuclear localization sequence (at 3' and 5') and a V5 tag were also appended to create a Cas13a-V5-NLS version into the Cas13a construct, using gBlocks (Integrated DNA technologies) encoding V5 tag (Schematic in FIG. 1A).

Plasmids were linearized with Not-I HF (New England Biolabs) overnight and PCR purified using PCR clean-up kit (Qiagen), prior to in vitro transcription (IVT) using a T7 mScript™ Standard mRNA Production System (Cell Script, WI, USA) following the manufacturer's instructions. Equimolar ratios of ATP, GTP, and CTP were used with $N_1$-methylpseudouridine-5'-triphosphate (TriLink Biotechnologies). RNAs were capped using 2'-O-methyltransferase and subsequent addition of a poly-A tail, both according to the manufacturer's instructions. The mRNAs were then purified using an RNeasy kit (Qiagen) and treated with Antarctic Phosphatase (New England Biolabs) for 1 hour and purified again. RNA concentration of the purified mRNA was measured and stored at −80° C. until further use. The mRNAs were modified during the in vitro transcription process to increase the translational efficiency and assuage innate immune responses.

crRNA synthesis using DNA Duplex: Multiple crRNAs (CR) and target RNAs (trRNA or TR) corresponding to influenza virus A WSN/33 (IVA) were designed and synthesized (Integrated DNA Technologies, USA) or in vitro transcribed and purified in house (Table 1). The crRNA consists of conserved direct repeats (DRs) that are specifically recognized by *L. buccalis* Cas13a.

TABLE 1

Nucleotide sequences of crRNAs (CRs) from influenza virus genes with their respective target RNA sequences (TRs).

| crRNA (CR) | Sequence | SEQ ID NO: | Target RNA (TR) | Sequence | SEQ ID NO: |
|---|---|---|---|---|---|
| HA_1.1 | GGACCACCCCAAAAAUGAAGGGGACUAAAACAAAC UACUGGUCCUGUUAUAUGCA | 3 | HA_1.2 | GUGCAUAUAACAGGACCAG UAGUUUC | 14 |
| NP_1.1 | GGACCACCCCAAAAAUGAAGGGGACUAAAACAAAC UGGAGGACCUAUAUACAGGA | 4 | NP_1.2 | GUCCUGUAUAUAGGUCCUC CAGUUUC | 15 |
| NA_1.1 | GGACCACCCCAAAAAUGAAGGGGACUAAAACAAAG ACAAUGGCAUAAGAAUUGGU | 5 | NA_1.2 | GACCAAUUCUUAUGCCAUU GUCUUUC | 16 |
| MM_2.1 | GGACCACCCCAAAAAUGAAGGGGACUAAAACAAAU AACAUGGACAAAGCAGUUAA | 6 | MM_2.2 | GUUAACUGCUUUGUCCAUG UUAUUUC | 17 |
| NN_2.1 | GGACCACCCCAAAAAUGAAGGGGACUAAAACAAAC UCUACAGAGAUUCGCUUGGA | 7 | NN_2.2 | GUCCAAGCGAAUCUCUGUA GAGUUUC | 18 |
| PB2_1.1 | GGACCACCCCAAAAAUGAAGGGGACUAAAACAAAG UGGAAUGCAGUUCUCCUCAU | 8 | PB2_1.2 | GAUGAGGAGAACUGCAUUC CACUUUC | 19 |
| gPB1 | GGACCACCCCAAAAAUGAAGGGGACUAAAACAAAG UGCUGCAACUUAUUUGAAAA | 9 | gPB1-TR | GUUUUCAAAUAAGUUGCAG CACUUUC | 20 |
| PB1_2.1 | GGACCACCCCAAAAAUGAAGGGGACUAAAACUUCA UACAGAAGACCAGUCGGGAU | 10 | PB1_2.2 | GAUCCCGACUGGUCUUCUG UAUGAAC | 21 |

TABLE 1-continued

Nucleotide sequences of crRNAs (CRs) from influenza virus genes with their respective target RNA sequences (TRs).

| crRNA (CR) | Sequence | SEQ ID NO: | Target RNA (TR) | Sequence | SEQ ID NO: |
|---|---|---|---|---|---|
| PB1_3.1 | GGACCACCCCAAAAAUGAAGGGGACUAAAACUGAAAAAUUCUUCCCCAGCAGUUC | 11 | PB1_3.2 | GGAACUGCUGGGGAAGAAUUUUUCAC | 22 |
| PB1_4.1 | GGACCACCCCAAAAAUGAAGGGGACUAAAACAAACAGAUUGUGUAUUGGAAGCAA | 12 | PB1_4.2 | GUUGCUUCCAAUACACAAUCUGUUUC | 23 |
| NT-CR | GGUAGACCACCCCAAAAUGAAGGGGACUAAAACACAAAUCUAUCUGAAUAAACUCUUCUUC | 13 | | | |

The DNA duplexes (Table 2) were in vitro transcribed using NEB HiScribe T7 High Yield RNA Synthesis Kit. The RNA was synthesized using 1 μg of DNA duplex template, NTPs (ATP, GTP, UTP, CTP 10 mM each), 10× reaction buffer, T7 polymerase and incubated for 16 h at 37° C. To this 20 μl reaction volume, 1 μl of DNase I (New England Biolaboratories) was added and incubated for 15 min at 37° C. followed by heat inactivation at 75° C. for 10 min. The RNA was mixed with equal volume of 2×RNA loading dye and heated for 65° C. for 5 min and immediately placed on ice for 10 min before loading it on 15% TBE-Urea Gels (Novex™, Invitrogen) for electrophoresis. The gel was stained with SYBR™ gold nucleic acid gel stain (Invitrogen) for 30 min. The RNA gel was excised from the gel under UV illumination and placed in 1 mL gel elution buffer. The excised gels were frozen at −80° C. followed by thawing at 65° C. (10 min) in water bath and, this was repeated two more times. The RNA was purified from the gel elution buffer using RNA clean and concentrator (Zymo Research).

TABLE 2

Nucleotide sequences of DNA duplexes encoding crRNAs (CRs) from influenza and RSV genes

| Duplex Name | Sequence | SEQ ID NO: |
|---|---|---|
| T7_gPB1 | TAATACGACTCACTATAGGACCACCCCAAAAATGAAGGGGACTAAAACAAAGTGCTGCAACTTATTTGAAAA | 24 |
| T7_mPB1 | TAATACGACTCACTATAGGACCACCCCAAAAATGAAGGGGACTAAAACTTTTCAAATAAGTTGCAGCACTTT | 25 |
| T7_gRSV | TAATACGACTCACTATAGGACCACCCCAAAAATGAAGGGGACTAAAACAAACAATTCAAGCCATGGGACAAA | 26 |
| T7_RSV-M2 | TAATACGACTCACTATAGGACCACCCCAAAAATGAAGGGGACTAAAACTTTGTCCCATGGCTTGAATTGTTT | 27 |

RNA Cleavage Activity of In Vitro Translated of Cas13a:

In order to assess Cas13a activity for a variety of crRNA and trRNA, Cas13a mRNA was translated in vitro using Rabbit reticulocyte lysate system as per the manufacturer's instructions (Promega, WI, USA). RNaseAlert®-1 substrate was mixed with crRNA (500 nM), trRNA (500 nM) in RNA processing buffer, consisting of A549 cells RNA (100 ng), 20 mM HEPES (pH 6.8), 50 mM KCl, 5 mM MgCl2, BSA (10 ng/ml), yeast tRNA (10 ng/ml), 0.01% Igepal CA-630 and 5% glycerol 19. This mixture was added cold to the translated Cas13a lysate (5 μl) in the 96-well plate wells and mixed well using pipette. All of the reagent preparations and additions were made on ice. The fluorescence measurements (excitation 485±20 nm/emission 528±20 nm) were recorded at room temperature for 90 min at 10 min interval. The RNA cleavage products (end-products) were then run on 15% urea TBE gels. The gel was stained with SYBR gold for 30 min and visualized under UV illumination.

Cell lines and viruses: All cell lines and viruses were purchased from American Type culture collection (ATCC. Manassas, Va.). Human lung epithelial cells A549 (CCL185), MDCK, and normal, Human primary Bronchial/Tracheal Epithelial Cells (ATCC® PCS-300-010™) were grown in media recommended by ATCC. Influenza virus stocks were prepared in MDCK cells, whereas, RSV stocks were prepared in HEp-2 cells. Briefly for influenza virus, MDCK cells were grown to 100% confluence in 175 mm2, next day cells were washed twice with PBS and 1:1000 dilution of virus was added in 5 ml EMEM. Cells were then incubated with virus for 1 h at room temperature on a rocker. Then, 25 ml media was added to the cells. Cells were observed for 72 h or until cytopathic effect was severe. Virus was collected by centrifuging the cells at 1000×g for 10 min. Virus titers were determined by standard plaque assay. For RSV stock preparation, HEp-2 cells were cultured until confluent and 3 ml of virus stock was incubated for 1 h at room temperature on a rocker. Then, 7 ml of DMEM was added to the cells and incubated for 5-6 days or until complete cytopathic effect was seen. Virus was collected from the supernatant by centrifuging the cells at 1000×g for 10 min. Virus titers were determined by standard plaque assay.

Optimization of mRNA Transfection:

Neon® Transfection System (Invitrogen, Fisher scientific), Lipofectamine 3000 (Thermos Fisher Scientific) and Viromer Red (Lipocalyx GmbH) transfection methods were assayed for transfecting Cas13a mRNA in MDCK and A549 cell lines. For Lipofectamine 3000 and Viromer Red transfection experiment, cells were seeded (125,000 cells/well) on coverslips (12 mm) overnight and transfected next day with 1 μg of Cas13a mRNA as per the respective manufacturer's protocol. For Neon® transfection system, cells were electroporated with 1 μg of Cas13a mRNA using the build-in program for A549 and MDCK of the Neon® Transfection System and seeded onto the coverslips with media. The transfected cells were fixed with 4% paraformaldehyde (10 min) at 2, 4, 6, 16 and 24 h post-transfection. The cells were permeabilized with triton X-100 (0.1%) for 5 min followed by blocking with 5% BSA for 1 h. Rabbit anti-V5 (Abcam ab9116) primary antibody and donkey anti-rabbit A488 (A21206 Invitrogen) secondary antibody were incubated for 1 h each respectively. The cells were visualized with PerkinElmer Ultraview ERS Spinning Disk microscope.

In vitro anti-viral assay: In a 24 well plate, A549 cells growing in Dulbecco's minimum essential medium were transfected with mRNA encoding Cas13a (1 µg) and crRNA (100 nM) or non-target crRNA (NT-CR) (100 nM) using Viromer Red. After 4 h of transfection, Influenza virus A WSN/33 (H1N1) at MOI of 0.01 or MOI of 0.1, was added to cells. Total RNA was extracted using RNeasy mini kit after 24/48/72 hours of transfection. cDNA was prepared using high-capacity cDNA reverse transcription kit (The Applied Biosystems™, Thermo Fisher Scientific). The anti-viral activity of Cas13a system was measured for the viral genes (Table 3) for all treatment groups. The viral inhibition was also observed microscopically with same experimental set-up as described above, however, the cells were seeded on the coverslip. The activity of Cas13a mediated IVA inhibition was demonstrated using the protocol recommended by Biosearch Technologies for sequential immunofluorescence and fluorescent in situ hybridization. Cells were then probed for Cas13a-V5 and IVA M2 protein using 1:250 anti-V5 tag Ab (Abcam ab9116) and 1:500 anti-M2 protein Ab (Abcam ab5416) followed by FISH probes targeting IVA genome (Table 4).

TABLE 3

Primer and probes (5'→3') used in this study.

| IVA | Forward | SEQ ID NO: | Reverse | SEQ ID NO: | Probe | SEQ ID NO: |
|---|---|---|---|---|---|---|
| HA | GGAGTGAAATTGGAATCAATGGG | 28 | GAACACATCCAGAAACTGATTGC | 36 | TTCTGGCGATCTACTCAACTGTCGC | 44 |
| M2-M1 | AGGTTCTCATGGAATGGCTAAA | 29 | GGTGAGCGTGAACACAAATC | 37 | ACAAGACCAATCCTGTCACCTCTGAC | 45 |
| NA | TTAAGGACAGAAGCCCTTATAG | 30 | GACCAAGCAACCGATTCA | 38 | TTAATGAGCTGCCCTGTCGGTGAA | 46 |
| NEP | CTACAGAGATTCGCTTGGAGAAG | 31 | ACCTAATTGTTCCCGCCATT | 39 | TGAGAATGGGAGACCTCCACTCACT | 47 |
| NP | GACCCTTTCAGACTGCTTCA | 32 | CATCCACACCAGTTGACTCTT | 40 | AGCCTAATCAGACCAAATGAGAATCCAGC | 48 |
| PA | GGATGGAAGGAACCCAATGT | 33 | TTCTCCTCATTCTCAATGTCCTG | 41 | CTGTCATGGAAGCAAGTACTGGCAGA | 49 |
| PB1 | ATCTTTGAGACCTCGTGTCTTG | 34 | CAGCAGGCTGGTTCCTATTTA | 42 | ACACGAGTGGACAAGCTGACACAA | 50 |
| PB2 | GTCAGTGAAACACAGGGAACA | 35 | CCAACACTGATTCAGGACCATTA | 43 | ACTTACTCATCGTCAATGATGTGGGAGA | 51 |

TABLE 4

Fluorescence in-situ hybridization (FISH) Stellaris ® probes labelled with Quaser ® 670 dye targeting Influenza Virus A (WSN/33)

| Probe Sequence Name | Probe Sequence (5'→ 3') | SEQ ID NO: |
|---|---|---|
| IVAWSN33_1 | AAATGGACAGGGCCAAAGGT | 52 |
| IVAWSN33_2 | GACGAAATTCAGGTCACCTC | 53 |
| IVAWSN33_3 | GCTGCGAAGGGAAGAAGTTT | 54 |
| IVAWSN33_4 | CTGGGTCTTCAGTTAAAGGG | 55 |
| IVAWSN33_5 | CAGAACTGCGGACTCAACTC | 56 |
| IVAWSN33_6 | CCCACTTCGTTAGGGAAAAC | 57 |
| IVAWSN33_7 | ATGGGATTCCTCAAGGAAGG | 58 |
| IVAWSN33_8 | GTTTCAAGACACGAGGTCTC | 59 |
| IVAWSN33_9 | GGGTGCATTCACAATCAGAG | 60 |
| IVAWSN33_10 | CAAATGGGTTCAGTGGGTTG | 61 |
| IVAWSN33_11 | CTGTATGAACTGCTGGGGAA | 62 |
| IVAWSN33_12 | GCTCTTCAATGGTGGAACAG | 63 |
| IVAWSN33_13 | CTCTCGGACTGACGAAAGGA | 64 |
| IVAWSN33_14 | AAGTCTAAGTGGTCGTGGTG | 65 |
| IVAWSN33_15 | CAGAGGACTCAGCTTCAATC | 66 |

TABLE 4-continued

Fluorescence in-situ hybridization (FISH) Stellaris ® probes labelled with Quaser ® 670 dye targeting Influenza Virus A (WSN/33)

| Probe Sequence Name | Probe Sequence (5'→ 3') | SEQ ID NO: |
|---|---|---|
| IVAWSN33_16 | ATTTGGACCGCTGAGAACAG | 67 |
| IVAWSN33_17 | TCAAGGCTGGAGAAGTTTGG | 68 |
| IVAWSN33_18 | GCATTAAGCAAAACCCAGGG | 69 |
| IVAWSN33_19 | GTCTTCGAGCAGGTTAACAG | 70 |
| IVAWSN33_20 | TGCTAGACGGGTGATGAACA | 71 |
| IVAWSN33_21 | ACGCGTTTGAGGTGATGATG | 72 |
| IVAWSN33_22 | TGGCGACAGTTGAGTAGATC | 73 |
| IVAWSN33_23 | GAGACCAAAAGCACCAGTGA | 74 |
| IVAWSN33_24 | TGTGCGAACAAGAGCTCTTG | 75 |
| IVAWSN33_25 | TTGAACCCTGCATCAGTGAG | 76 |
| IVAWSN33_26 | AGATCCATACACACAGGCAG | 77 |
| IVAWSN33_27 | AATGCAGCAGAATGGCATGC | 78 |
| IVAWSN33_28 | ATGTCAAAGGAGGGCACGAT | 79 |
| IVAWSN33_29 | CCACGGATGGGACAAAGAGA | 80 |
| IVAWSN33_30 | CGACAGGGCAGCTCATTAAG | 81 |
| IVAWSN33_31 | TTGAATTGTACGGGGACGGA | 82 |
| IVAWSN33_32 | CGCGGGTTGTCACCGAAAAC | 83 |
| IVAWSN33_33 | CAAGGCCTCATACAGTCTAG | 84 |
| IVAWSN33_34 | GTCAATGGTGAACGGCAACT | 85 |
| IVAWSN33_35 | CGGTATCAGGGTAACAGGAA | 86 |
| IVAWSN33_36 | GGCGCCTTGAGTCAGAAAAA | 87 |
| IVAWSN33_37 | CTGACGGGACGATAGAGAGA | 88 |
| IVAWSN33_38 | CAAGTCTCTGTGCGATCTCG | 89 |
| IVAWSN33_39 | CACGGTGAGCGTGAACACAA | 90 |
| IVAWSN33_40 | ACAAAGCGTCTACGCTGCAG | 91 |
| IVAWSN33_41 | TATGAGACCGATGCTGGGAG | 92 |
| IVAWSN33_42 | TGCTGCAATGACGAGAGGAT | 93 |
| IVAWSN33_43 | ATAGACTCTGGCACTCCTTC | 94 |
| IVAWSN33_44 | GAAGCCGATCAAGGAATGGG | 95 |
| IVAWSN33_45 | TTCGATGTCCAGACCGAGAG | 96 |
| IVAWSN33_46 | ACTTTCTGCTTGGGCATGAG | 97 |
| IVAWSN33_47 | CAACAATTGTCCCCTCTTCG | 98 |
| IVAWSN33_48 | GAGGGCAGTGGTGAAATTTC | 99 |

Cas13a-crRNA system against IVA was assessed under different conditions to determine its efficacy. The A549 cells were first infected with IVA (MOI 0.01) for 4 h and then cells were washed before transfecting with Cas13a (1 µg) and crRNA (100 nM) using Viromer Red. RNA was extracted after 24/48/72 hours of infection. In another experimental setup, cells were transfected with Cas13a-crRNA for 24 h and then infected with IVA (MOI 0.01) for 8 h and RNA was extracted from these cells. cDNA and qPCR was performed as mentioned above.

Plaque Assay:

The supernatant from the cells treated with Cas13a mRNA and crRNA (RSV_1.1 and RSV_m1.1) and RSV were centrifuged at 14000×g for 5 min. The supernatant was collected and 50 µl/well was laid on the Vero cell monolayer in 24-well plate for 1 h (intermittent rocking every 15 min). Avicel-DMEM overlay media containing 1:1 ratio of 2.4% Avicel (FMC Biopolymer RC-481) in 2×DMEM, along with 2% FBS and 100 U mL-1 penicillin and 100 mg mL-1 streptomycin (Life Technologies) was added to the monolayer and incubated for 6 days. The media was removed and washed with 1×PBS followed by fixing the cells with 4% paraformaldehyde for 10 min. The cells were blocked for 30 min with 5% BSA at 37° C., and subsequently stained with anti-RSV (goat polyclonal) primary antibody at 37° C. After 30 min, cells were washed and HRP conjugated-secondary antibody (donkey anti-goat) was incubated at 37° C. for 30 min. Plaques were developed using TrueBlue™ peroxidase substrate for 10 min at room temperature. TrueBlue was removed and cells were rinsed with water and plaques were air-dried and counted.

RNA Sequencing of Cas13a transfected cells during IVA infection: For RNA-Seq experiment, overnight grown A549 cells were transfected with Cas13a (1 µg) and crRNA (100 nM) using Viromer Red, after 4 h cells were infected with IVA (MOI 0.01) and as controls, a set of transfected cells were kept uninfected. RNA was extracted at 8 h and 24 h after transfection from all the treatment groups using RNeasy mini kit (Qiagen). RNA samples were used for RNA-Seq after confirming reduction in IVA PB1 copies in the gPB1 and mPB1 crRNA treatment groups. RNA was quantified and then depleted for rRNA with NEBNext® rRNA Depletion Kit. RNA library was prepared using NEBNext® Ultra™ II RNA Library Prep Kit for Illumina®. These libraries were Qubit Fluorimeter quantified (Thermo Fisher Scientific) and upon satisfying integrity on the Agilent 2100 Bioanalyzer (Agilent Technologies), the samples were sequenced on Illumina NextSeq 500 at pair end 75 mid output run. The reads were aligned with reference Human genome UCSC (hg38) using Bowtie2 and transcripts of control and treatment samples were compared for differential gene expression using Cufflinks. The log 2 values for differential expressions for significant genes were represented using GraphPad Prism.

Statistical Analyses: All experiments are represented as a mean of three biological replicates. All of the data was analyzed using GraphPad Prism 7.04. Statistical analyses were performed between groups using either ordinary one-way or two-way analysis of variance (ANOVA) with appropriate hypothesis tests, described in individual figure captions.

Figure 1B:
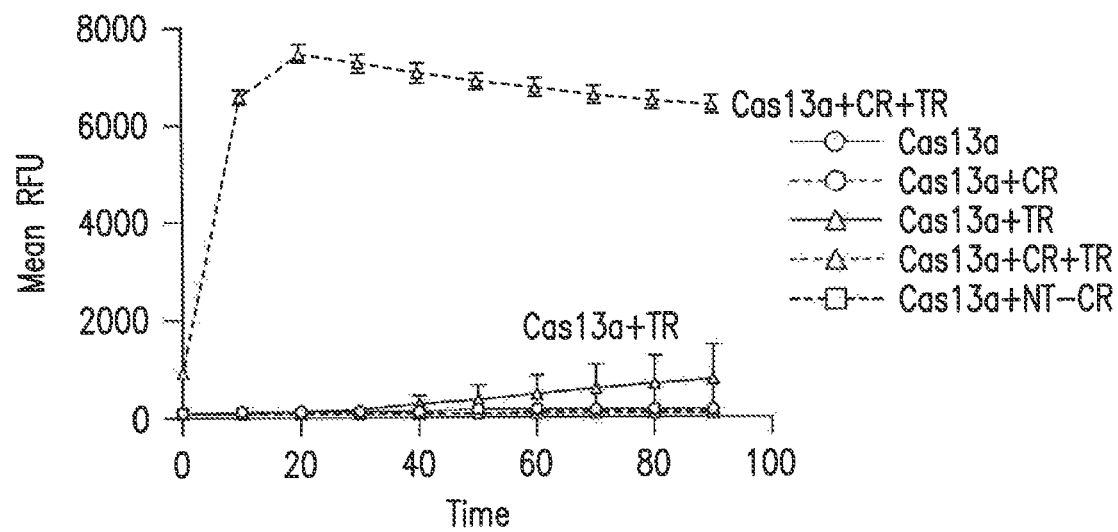
Figure 1C:
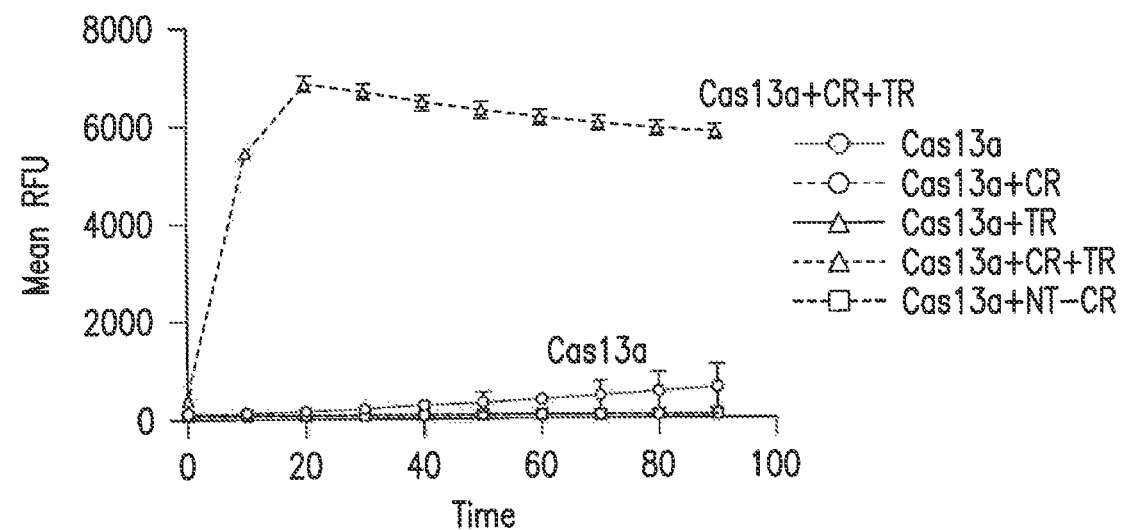
Figure 1E:
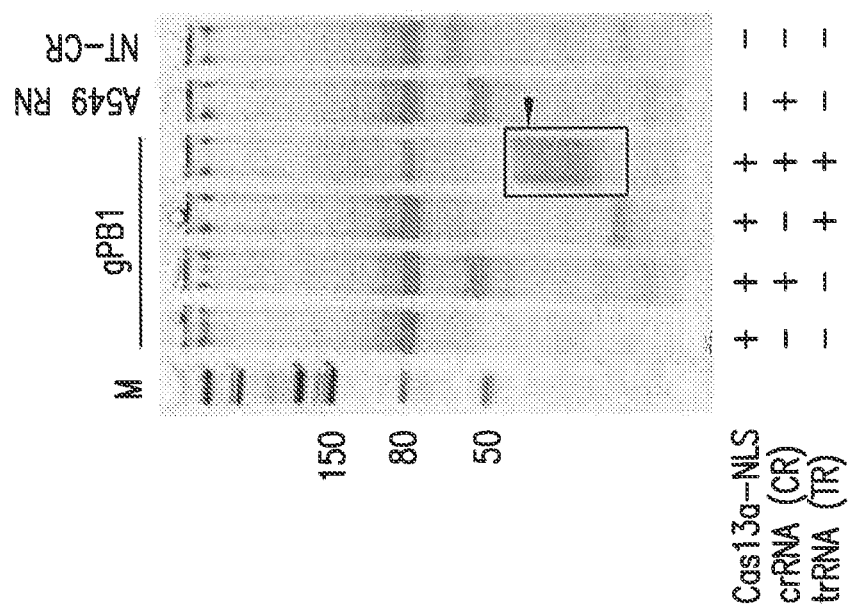
Figure 1D:
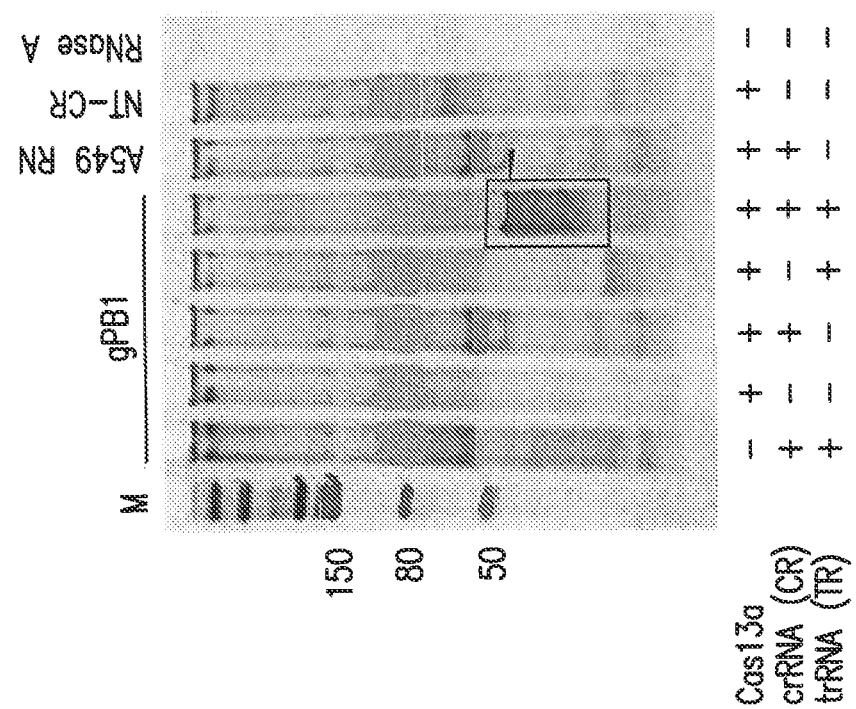
Figure 2A:
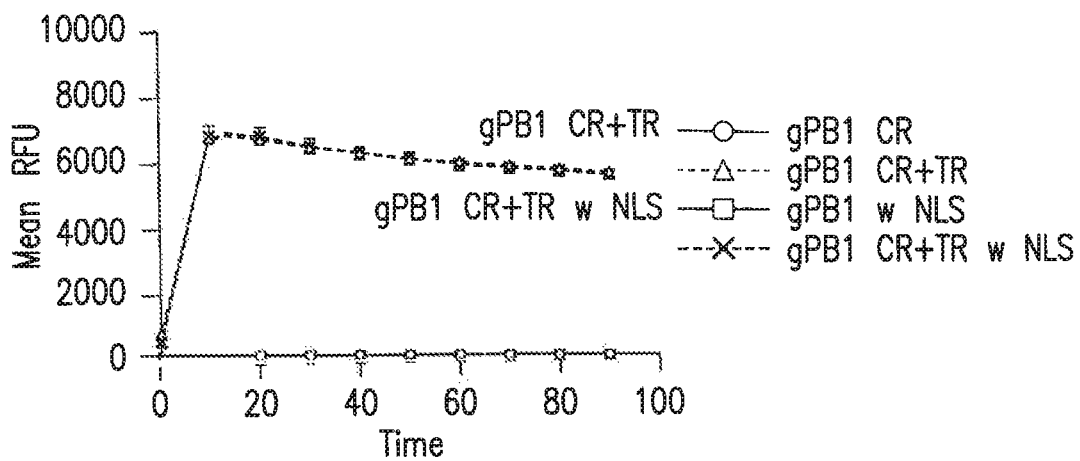
Figure 2B:
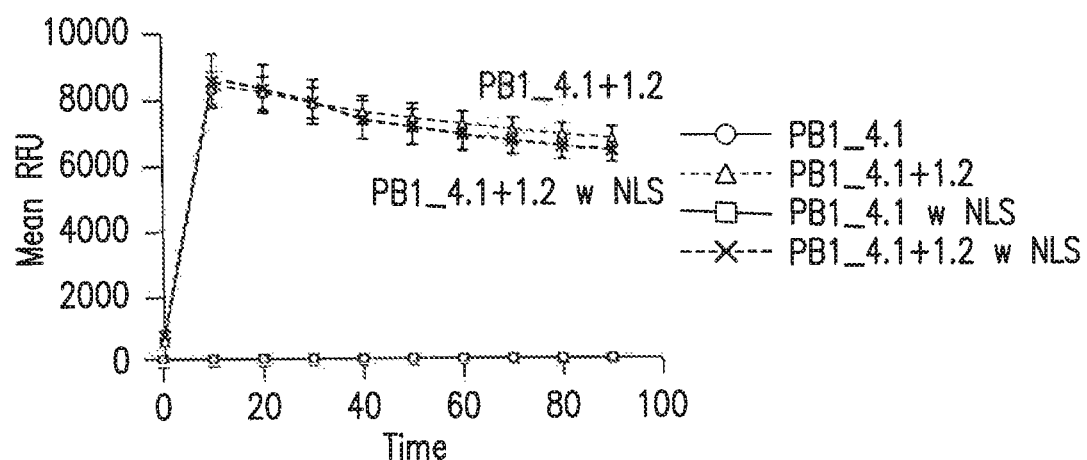
Figure 2C:
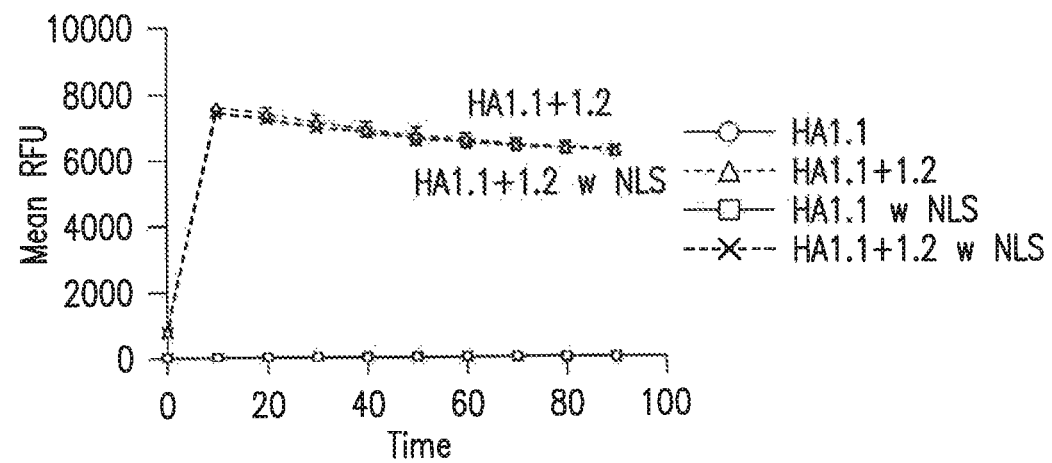
Figure 2D:
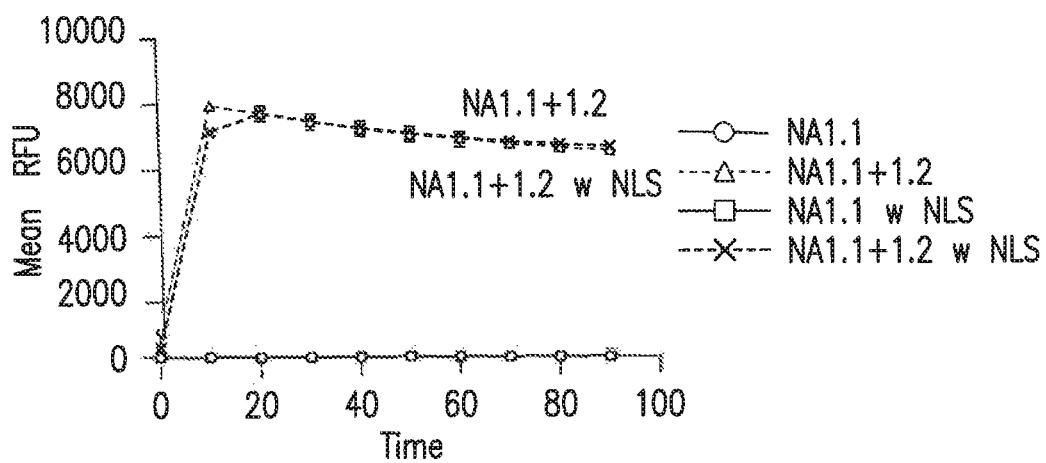
Figure 2E:
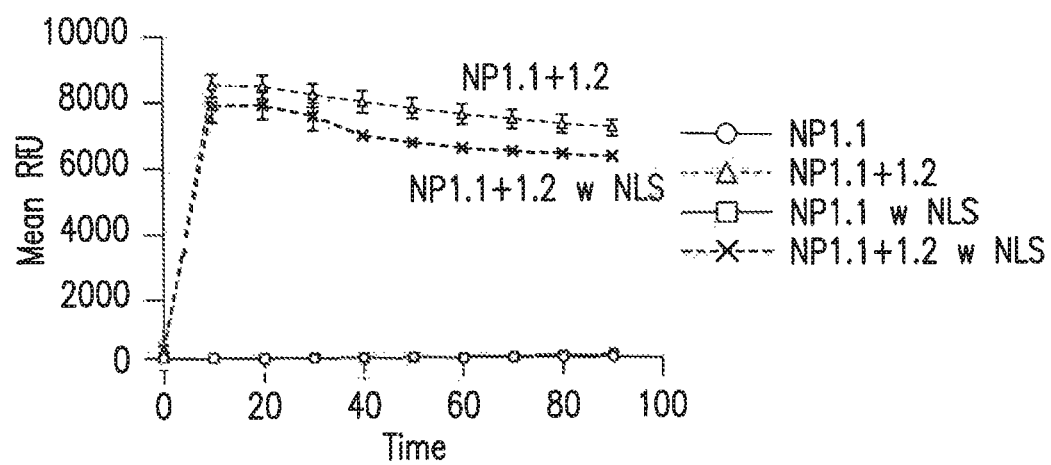
Figure 2F:
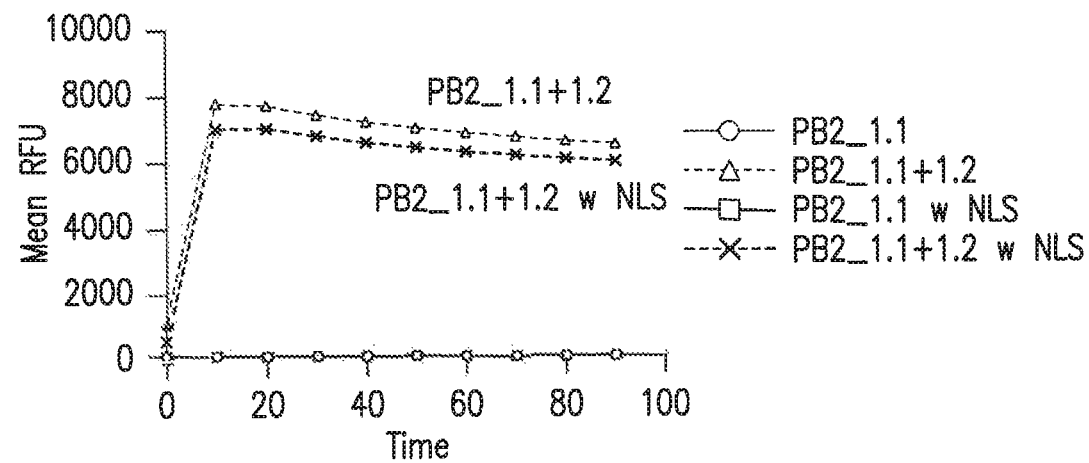
Figure 2G:
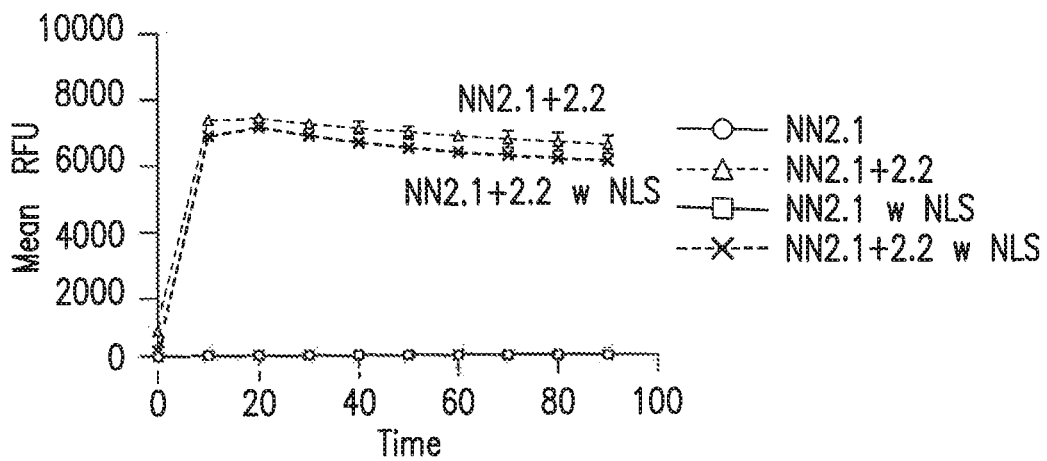
Figure 2H:
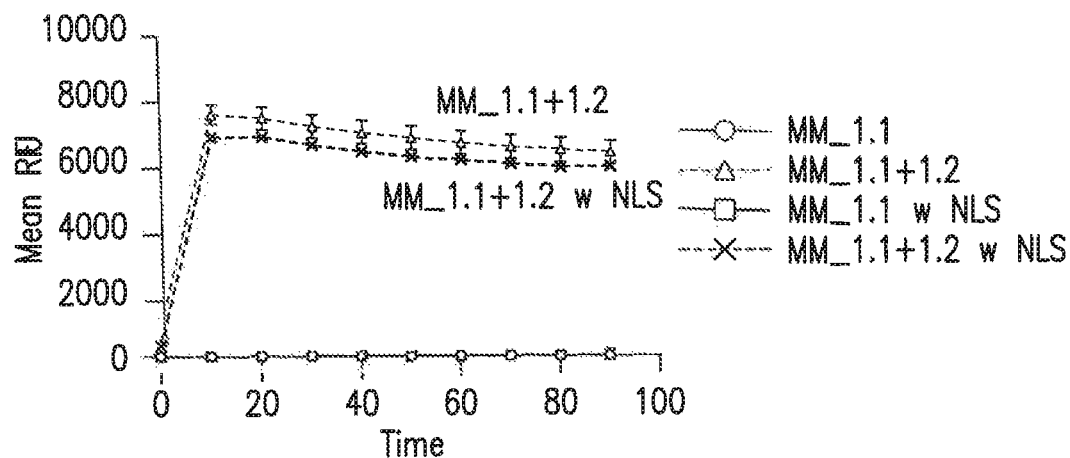
Figure 2I:
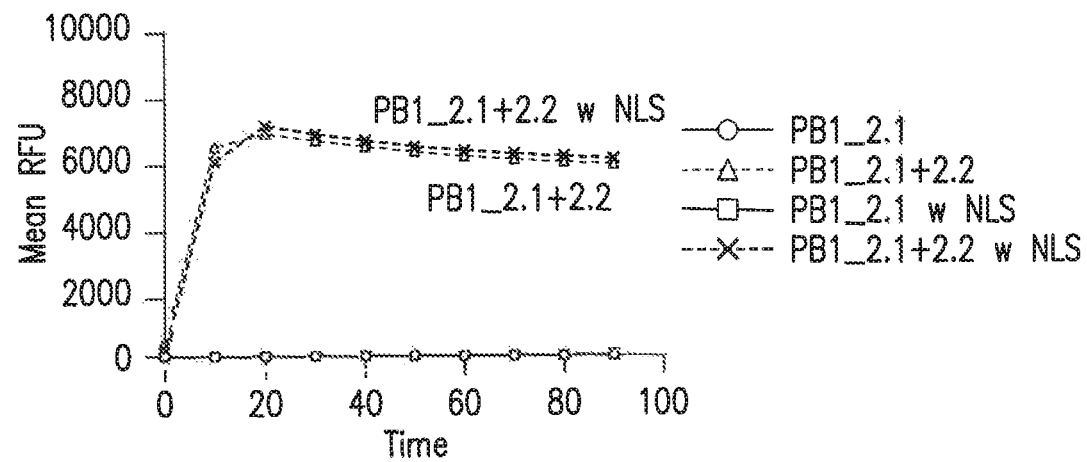
Figure 2J:
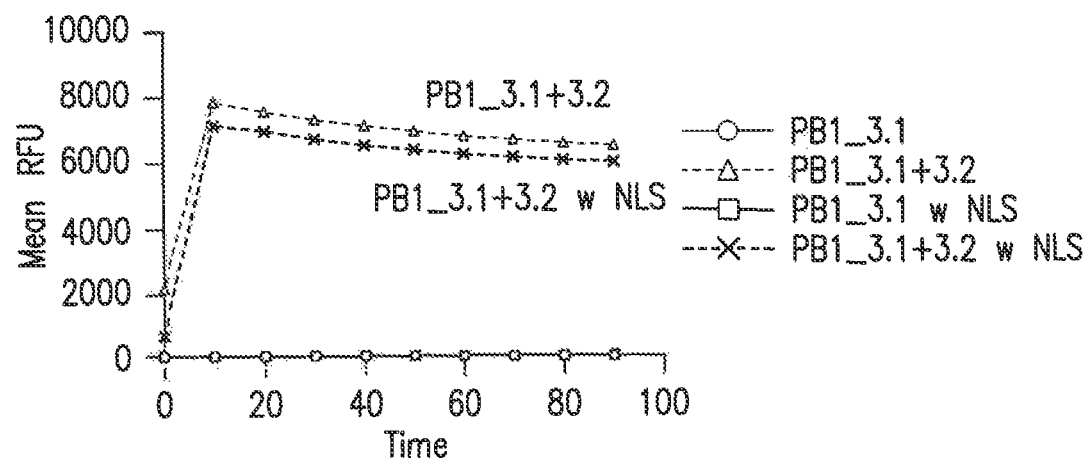
Figure 2K:
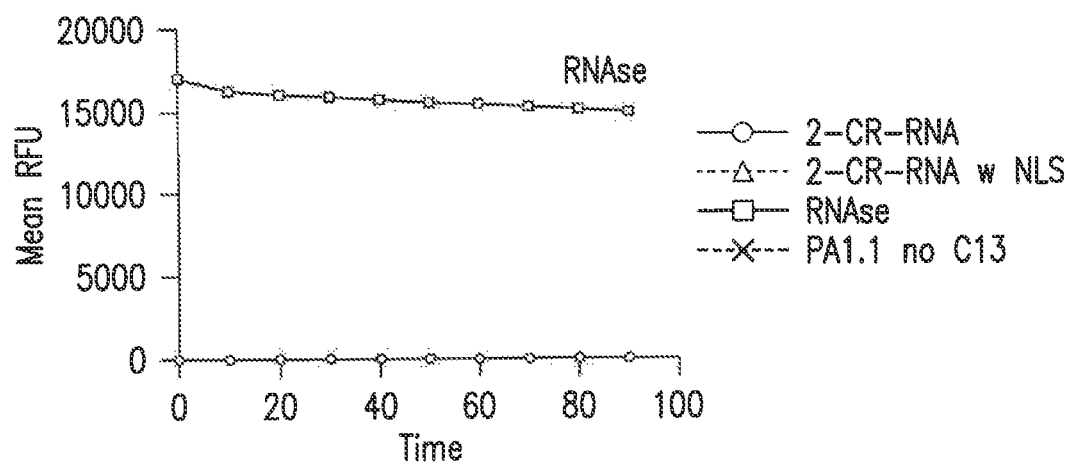
Figure 3A:
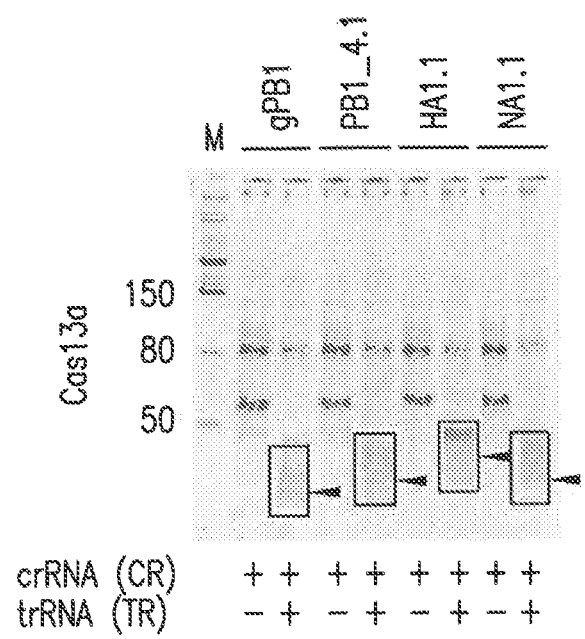
Figure 3B:
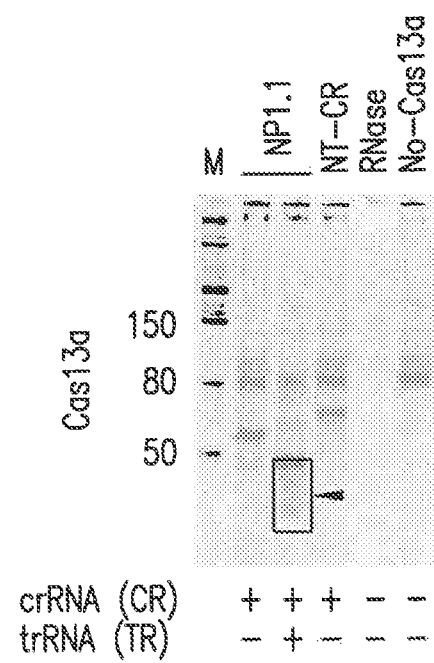
Figure 3C:
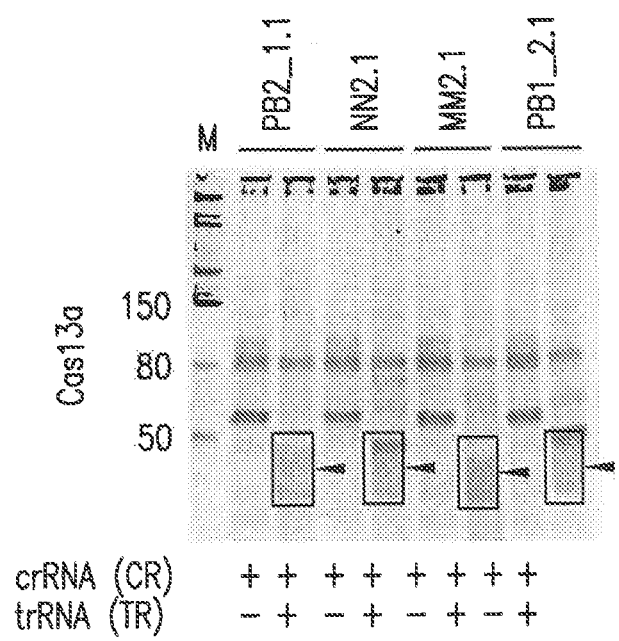
Figure 3D:
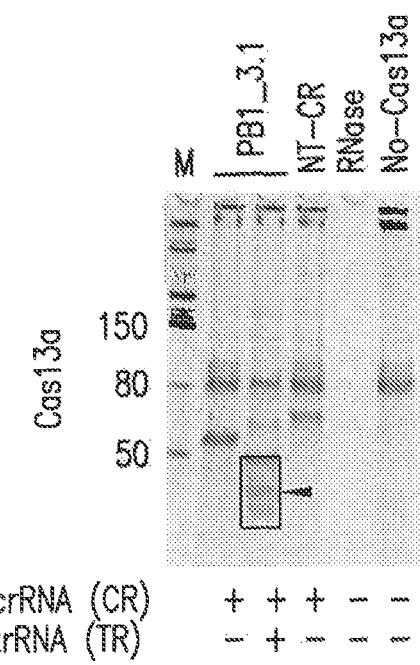
Figure 3E:
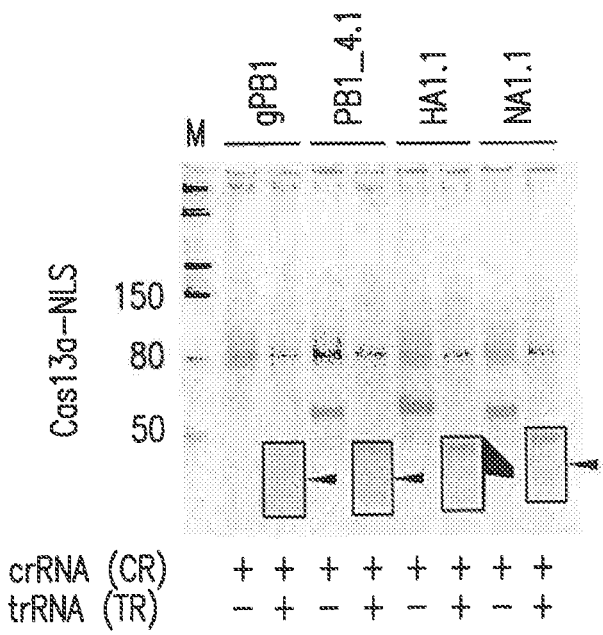
Figure 3F:
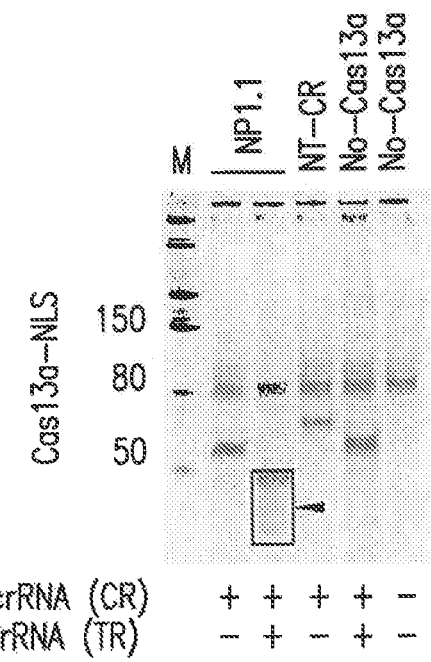
Figure 3G:
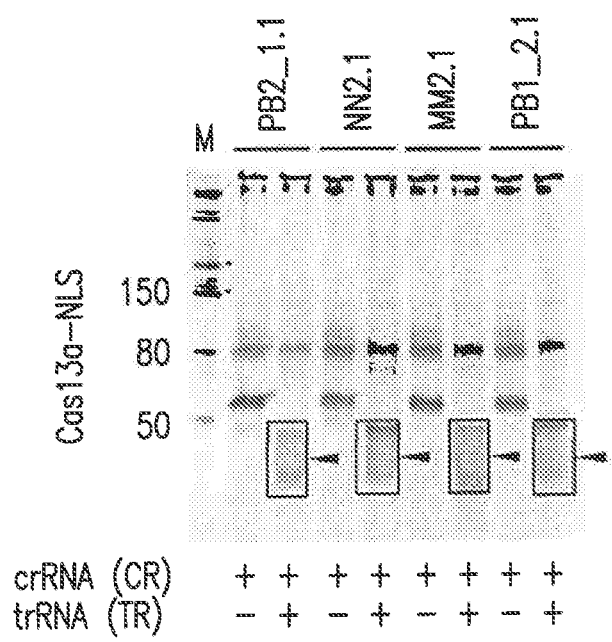
Figure 3H:
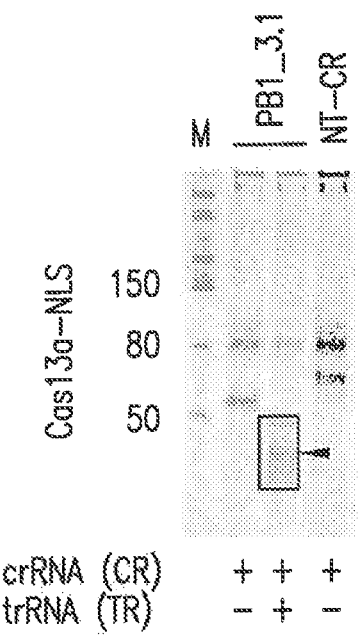

Results:

Using the rabbit reticulocyte lysate, Cas13a and Cas13a-NLS (version with nuclear localization sequence) mRNAs were translated in vitro and used to assess the RNA cleavage activity of the expressed Cas13a protein in conjunction with IVA crRNAs and trRNAs (FIG. 1A). crRNA and trRNA were derived from genome segments of IVA (Table 1). RNaseAlert™ substrate fluorescence was the output of RNA cleavage. Cas13a and Cas13a-NLS RNA cleavage generated fluorescence increased to its maximum during the initial 10 and 20 min period, respectively, and then gradually decreased over time due to depleted target RNA. The overall trend of RNA cleavage was similar for both the Cas13a (FIG. 1B) and Cas13a-NLS (FIG. 1C). RNA cleavage was also observed when the lysate was interrogated by gel electrophoresis using a 15% TBE-Urea gel (FIGS. 1D and 1E). These results indicate that in vitro translated Cas13a mediated RNA cleavage is specific and occurred only when both the crRNA and trRNA were present. The crRNA, NT-CR or Cas13a mRNA by itself does not cleave the target RNA. The results corroborate previous findings of specific activation, when purified Cas13a protein was used (East-Seletsky, A., et al., *Nature,* 538:270-273 (2016)). The presence of yeast tRNA or cellular RNA in the cleavage buffer to assay Cas13a activity did not yield fluorescence or cleaved RNA products, demonstrating the specificity of Cas13a:crRNA towards target RNA. These designed crRNAs showed RNA cleavage with in vitro translated Cas13a and Cas13a-NLS only in the presence of corresponding trRNAs (FIGS. 2A-2K and 3A-3H).

Example 2. Optimization of mRNA Transfection

Figure 4A:
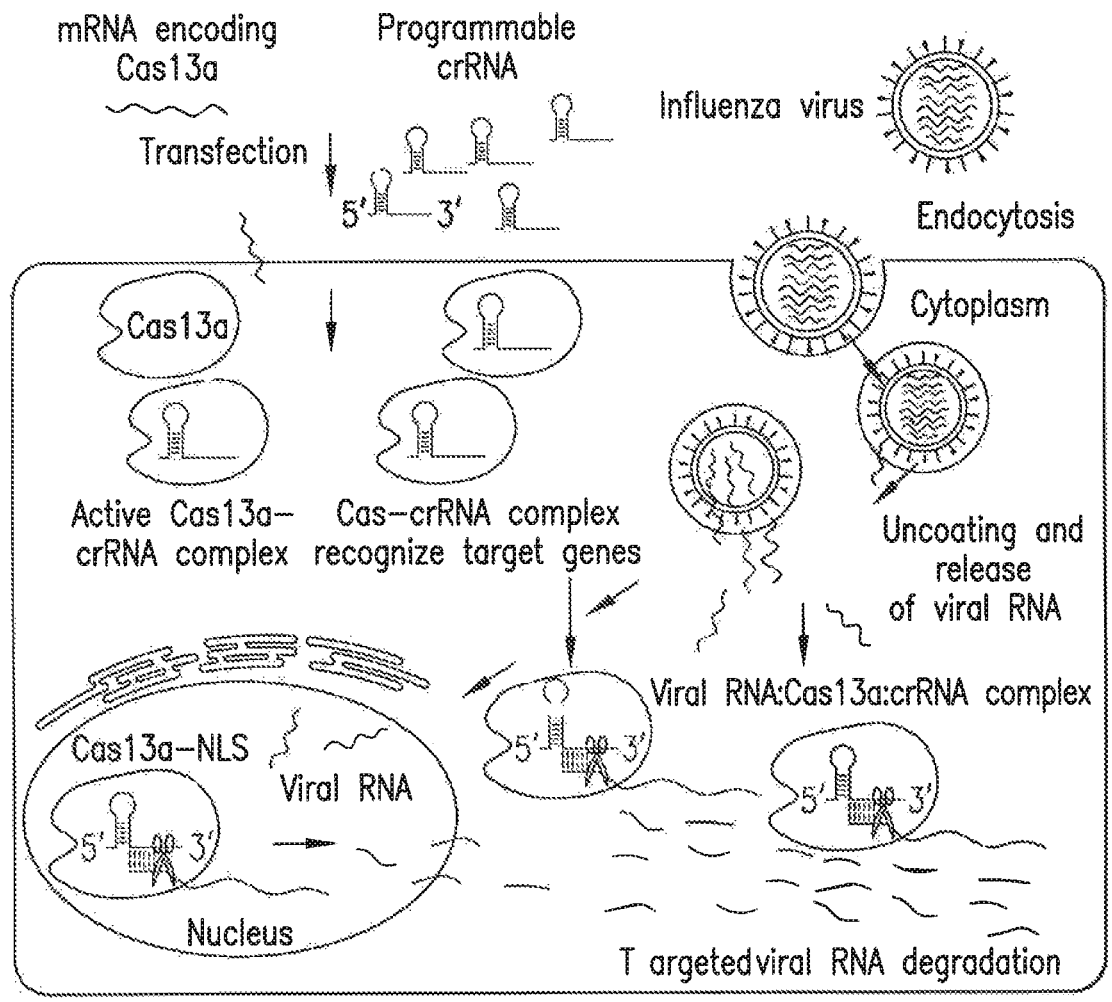
Figure 4F:
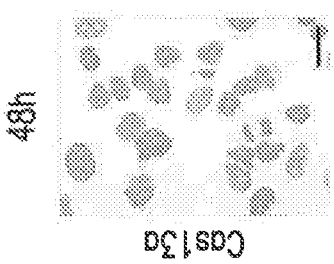
Figure 4K:
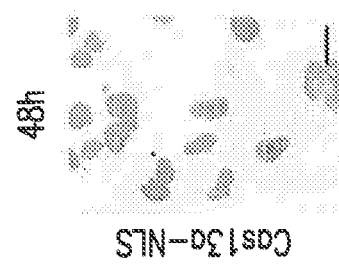
Figure 4E:
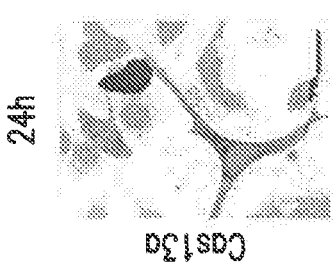
Figure 4J:
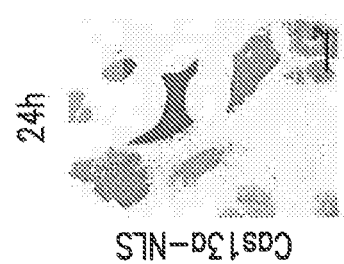
Figure 4D:
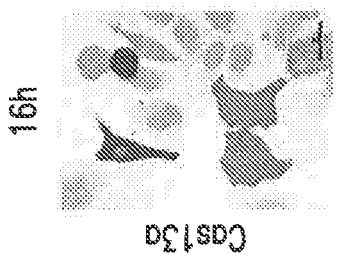
Figure 4I:
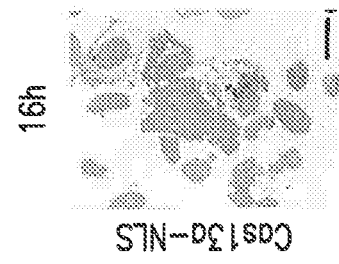
Figure 4C:
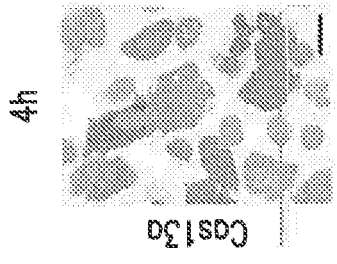
Figure 4H:
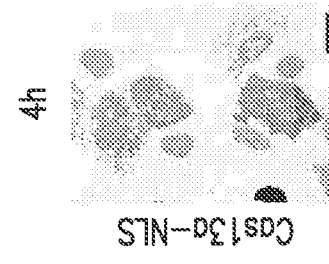
Figure 4B:
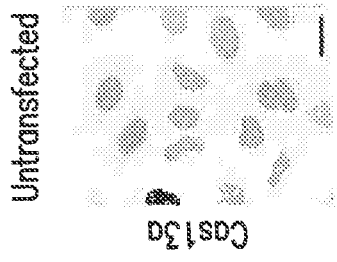
Figure 4G:
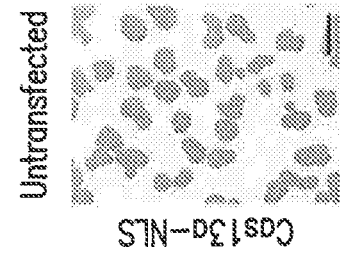
Figure 5A:
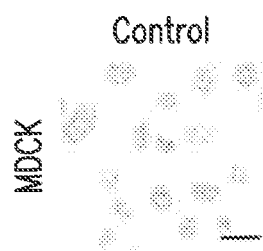
Figure 5B:
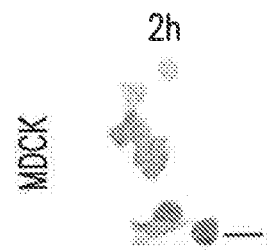
Figure 5C:
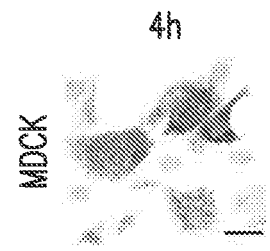
Figure 5D:
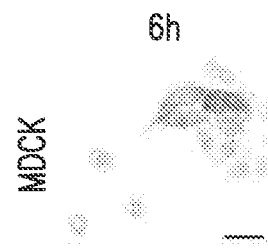
Figure 5E:
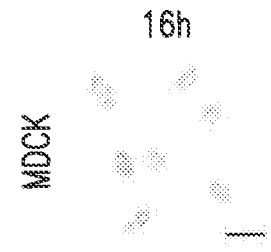
Figure 5F:
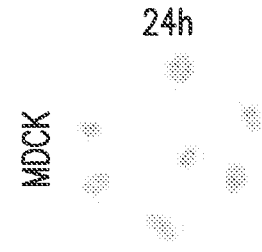
Figure 5G:
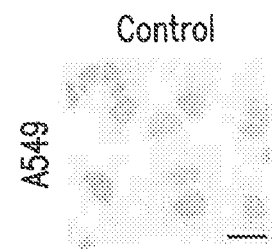
Figure 5H:
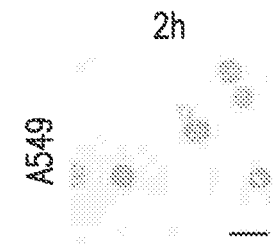
Figure 5I:
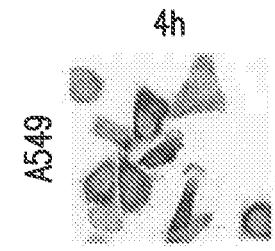
Figure 5J:
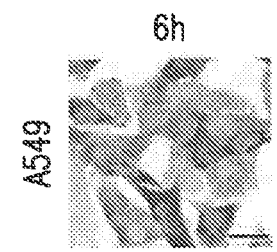
Figure 5K:
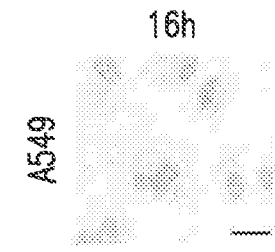
Figure 5L:
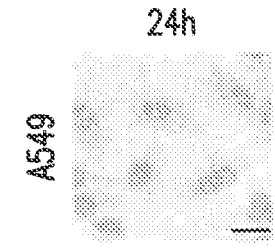
Figure 5M:
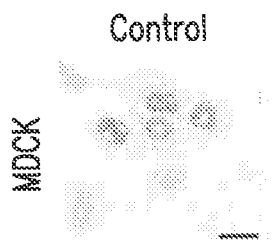
Figure 5N:
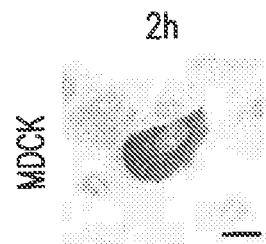
Figure 5O:
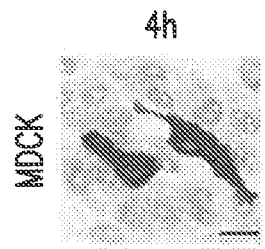
Figure 5P:
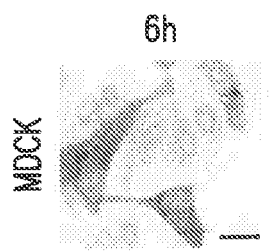
Figure 5Q:
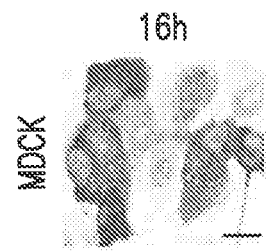
Figure 5R:
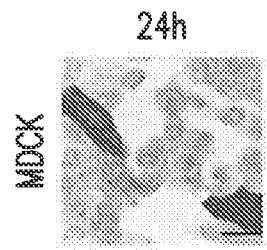
Figure 5S:
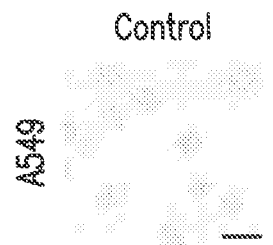
Figure 5T:
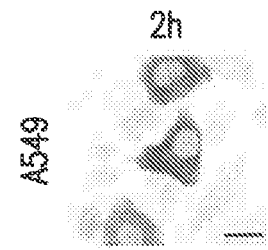
Figure 5U:
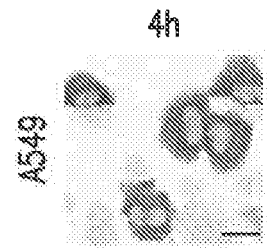
Figure 5V:
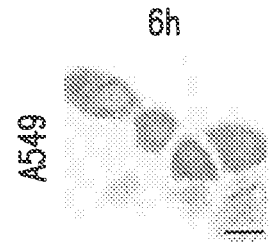
Figure 5W:
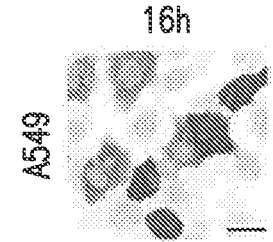
Figure 5X:
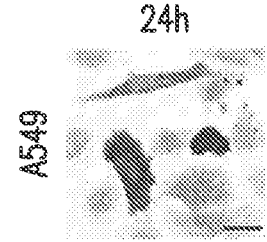
Figure 5Y:
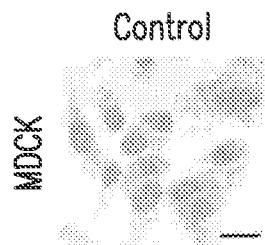
Figure 5Z:
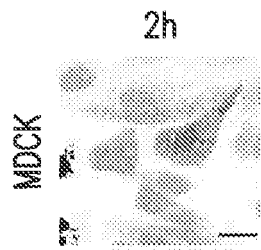
Figure 5A:
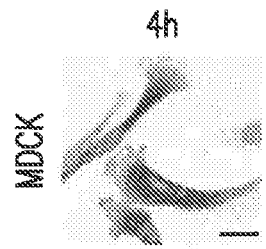
Figure 5B:
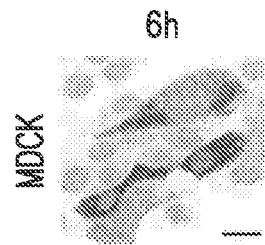
Figure 5C:
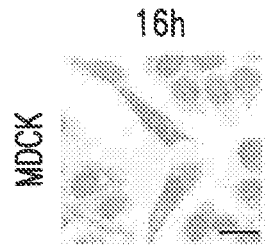
Figure 5D:
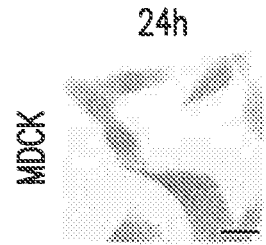
Figure 5E:
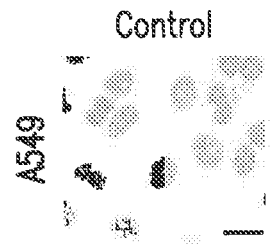
Figure 5F:
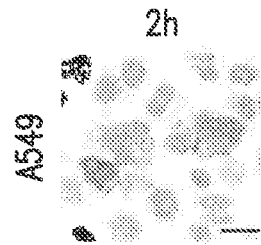
Figure 5G:
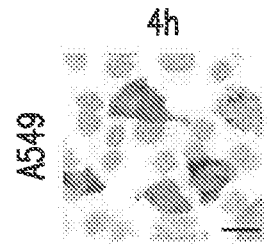
Figure 5H:
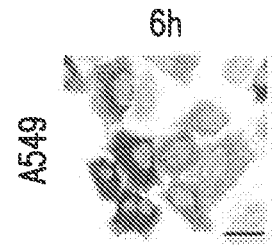
Figure 5I:
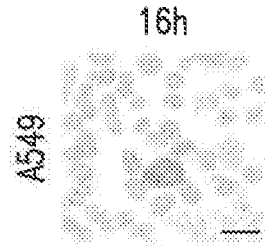
Figure 5J:
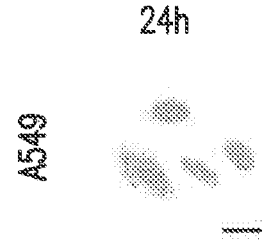

Results:

The Cas13a:crRNA system was then assessed in cellular models for influenza infections (FIG. 4A). mRNA delivery using transfection agents, Viromer® Red, and Lipofectamine 3000, and via electroporation using the Neon® transfection system in MDCK and A549 cell lines was assessed. Cas13a expression was evaluated at 2, 4, 6, 16 and 24 h time points (FIGS. 5A-5JJ). Cas13a expression was observed as early as 2 h post transfection for all transfection agents and cell types. However, 16 h post transfection, the Cas13a expression decreased in the all cell lines transfected with Neon and Lipofectamine 3000. The Viromer® Red transfected cells showed expression even at 24 h. Based on the results, Viromer® Red and A549 cell lines were selected for subsequent experiments. Using immunofluorescence, it was observed that Cas13a localized predominately within the cytoplasm, whereas Cas13a-NLS, was present in both the cytoplasm (as Cas13a is still being synthesized) and, at 48 hr, within the nucleus (FIG. 4B-4K).

Example 3. Screening of crRNAs Targeting Various IVA Segments

Figure 6A:
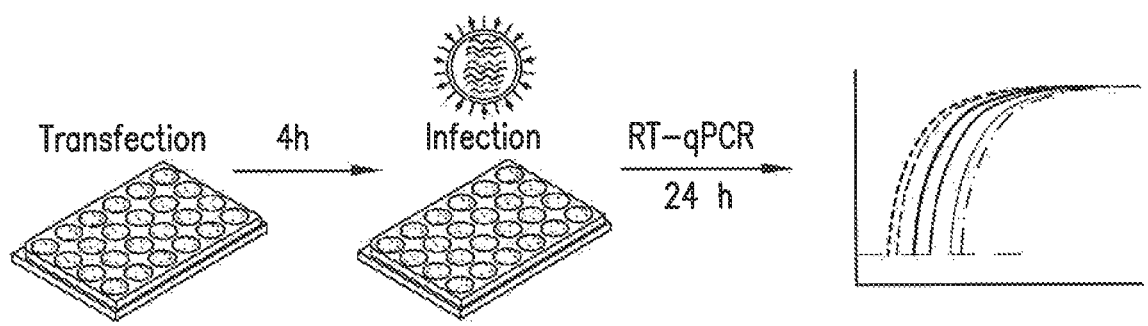
Figure 6B:
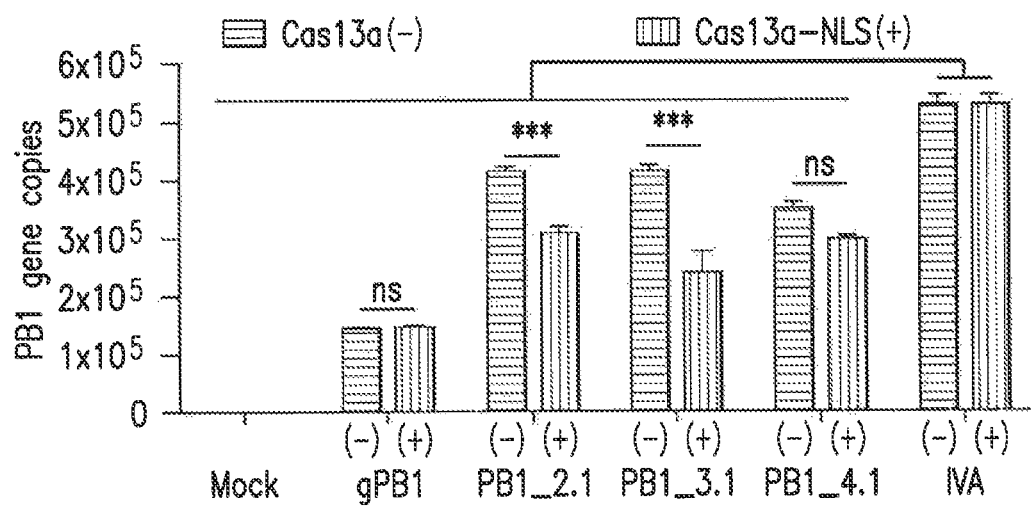
Figure 6C:
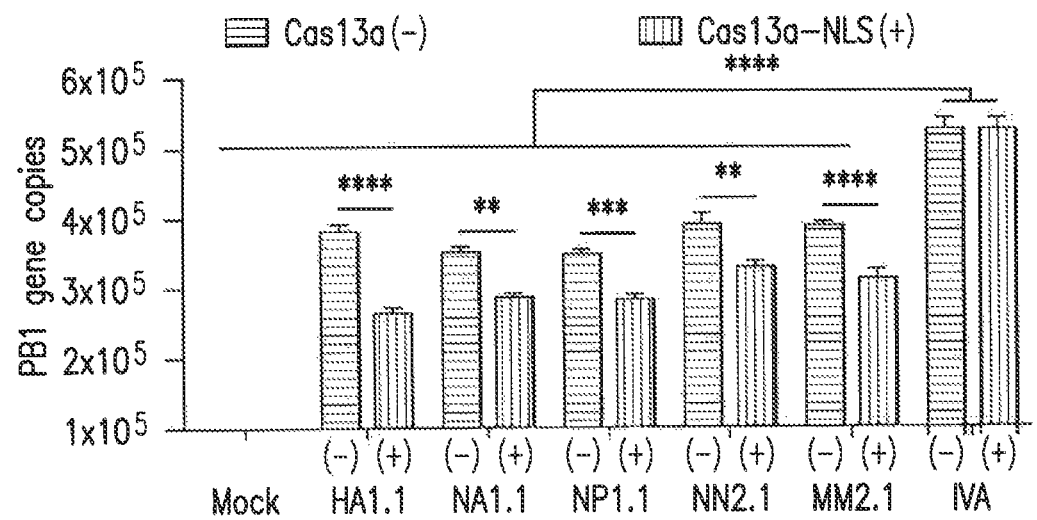

Results:

crRNAs targeting various genomic segments of IVA including polymerase (PB1), hemagglutinin (HA), neuraminidase (NA), nucleoprotein (NP) and nuclear export protein (NS1 and NS2) and M2 protein of the IVA were designed (FIGS. 6A-6C). A549 cells were simultaneously transfected with Cas13a or Cas13a-NLS mRNA and each crRNA followed by influenza virus infection (at multiplicity of infection, MOI 0.01). Given the polymerase is a critical protein for IVA replication, several crRNAs targeting the polymerase component, PB1 were designed. First, these crRNAs were tested with both Cas13a and Cas13a-NLS. Of the crRNAs tested, gPB1 was the most effective in reducing PB1 gene copies. A significant reduction in the PB1 gene copies was observed when crRNAs targeting other IVA genes were tested, suggesting an overall effect on the viral infectivity. As IVA localizes in the nuclei, Cas13a was tested with and without the nuclear localization signal (NLS).

Of all the crRNAs tested, the highest inhibition was seen in gPB1 both in Cas13a and Cas13a-NLS with 72.45% and 71.9% inhibition (FIG. 6B). Other non-PB1 targeting crRNAs also reduced PB1 copies but to a lesser extent. Of the non-PB1 crRNAs, HA 1.1 reduced PB1 copies by 27.7% in Cas13a and 49.87% with Cas13a-NLS (FIG. 6C).

Significant differences in the Cas13a and Cas13-NLS were not observed with gPB1 and PB1_4.1. However, in all other crRNAs, Cas13a-NLS was more effective. The significant difference between the Cas13a and Cas13-NLS is explained by the fact that the assays were performed during early infections where the viral genome is highly localized in the nuclei, thereby easily targeted by the Cas13a-NLS and the crRNAs. gPB1 was the most effective of all the crRNAs irrespective of the Cas13a with or without NLS.

Figure 6D:
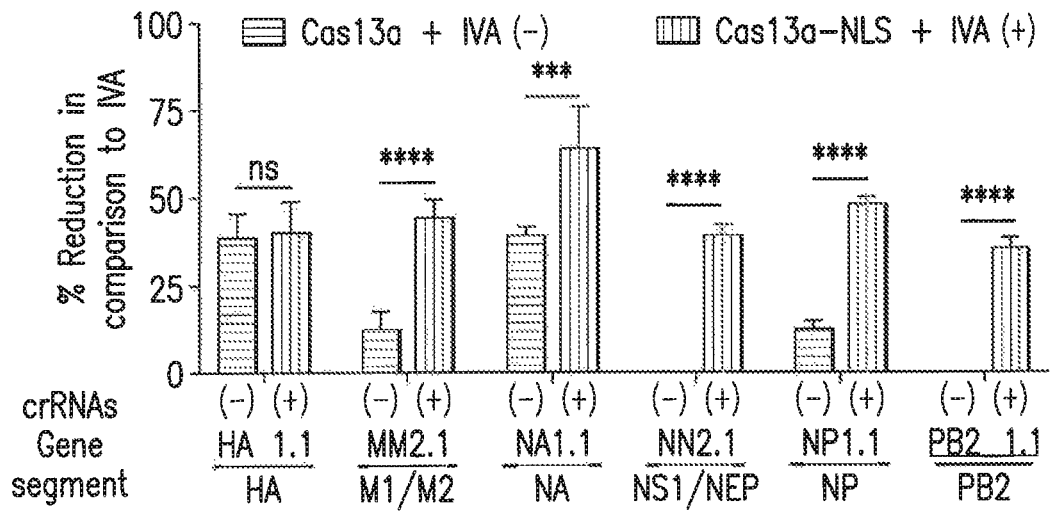
Figure 6E:
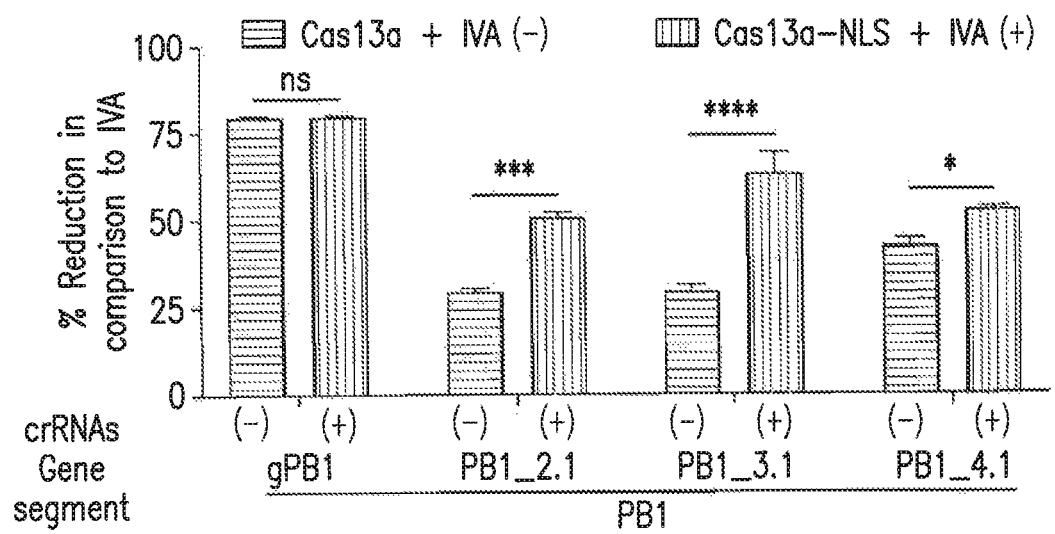
Figure 7A:
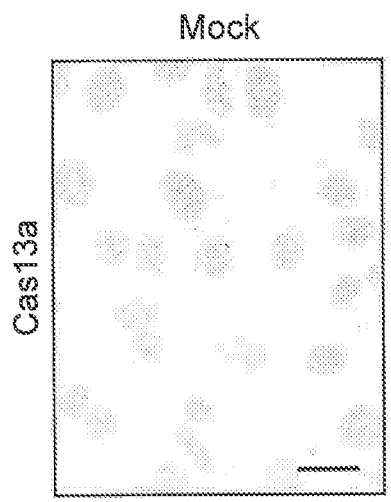
Figure 7B:
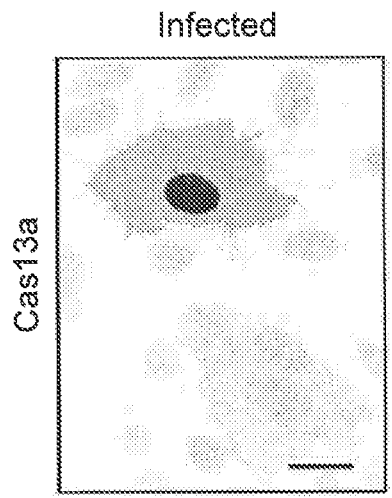
Figure 7C:
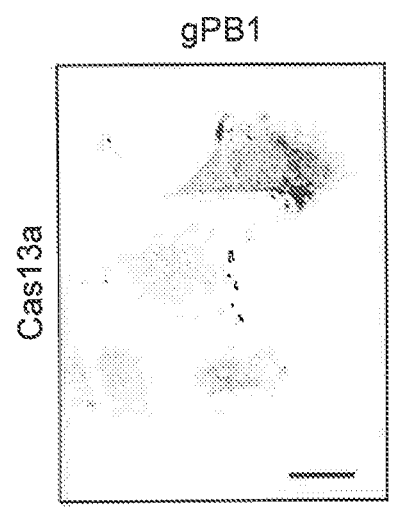
Figure 7D:
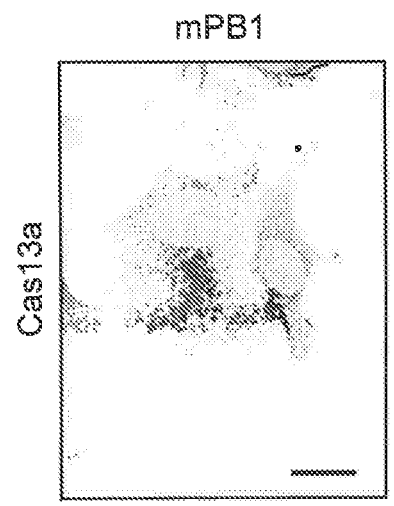
Figure 7E:
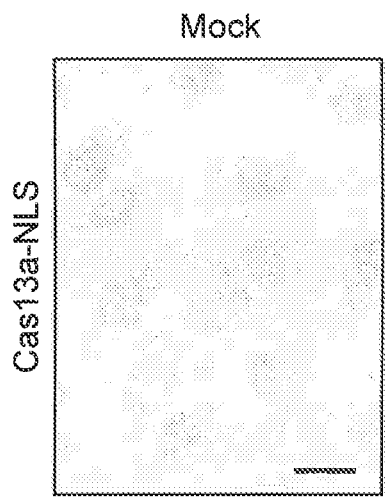
Figure 7F:
Figure 7G:
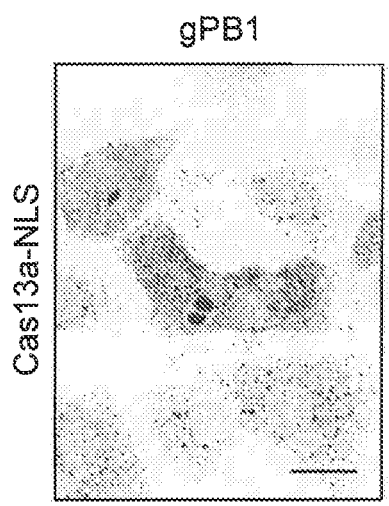
Figure 7H:

After evaluating the effects of these crRNAs on PB1 gene, their effects on their parent genes were evaluated. For this, the cells were transfected with either Cas13a or Cas13a-NLS and various crRNAs and then infected with IVA. Next day, we analyzed the percent reduction in the parent viral gene copy numbers (to which the crRNA targeted) compared to an infection only control. Again, the highest reduction was observed in PB1 gene copies when gPB1 crRNA was used with 75% reduction whereas all other crRNAs showed nearly 50% reduction in copy numbers of their respective genes (FIGS. 6D and 6E).

To further confirm whether these crRNAs affect their parent gene copies, RT-qPCR was performed after transfecting and infecting cells as described in FIG. 6A. Most efficient crRNAs were NA1.1, particularly when used with Cas13a-NLS (FIG. 6D). The ability of PB1 targeting crRNAs to inhibit their parent genes was investigated. Of the crRNAs tested highest inhibition was in gPB1 (79%) in both Cas13a and Cas13a-NLS followed by PB1_3.1 (62.9%) with Cas13a.

From these results, it was established that the gPB1 sequence was the most effective crRNA against IVA among those tested, and therefore was used for further experiments.

Example 4. crRNAs can be Programmed to Target IVA mRNA

Results:

Among all the crRNAs screened, the crRNA targeting the PB1 genome segment (gPB1) was found to reduce viral RNA copies most efficiently (FIGS. 6B and 6E) and impacts other viral proteins. To demonstrate this in situ, immunofluorescence for Cas13a, IVA M2 protein (indicating viral assembly or disassembly sites 24) was performed, followed by fluorescence in situ hybridization (FISH) for the IVA genome visualization. Cells transfected with either the Cas13a or Cas13a-NLS mRNAs and crRNA, targeting PB1 site, (gPB1 and mPB1 targeting PB1 mRNA) showed reduced M2 protein, indicative of reduced IVA infection (FIGS. 7A-7H), and localization of Cas13a to viral infection sites within the cytosol. From this data, it is clear that, by targeting the polymerase gene other viral proteins could be inhibited, thus achieving higher inhibitory effects.

Example 5. Optimization of Cas13a-crRNA Doses and Viral Infections In Vitro

Results:

Dose Response Assay of Cas13a: crRNA

Figure 8A:
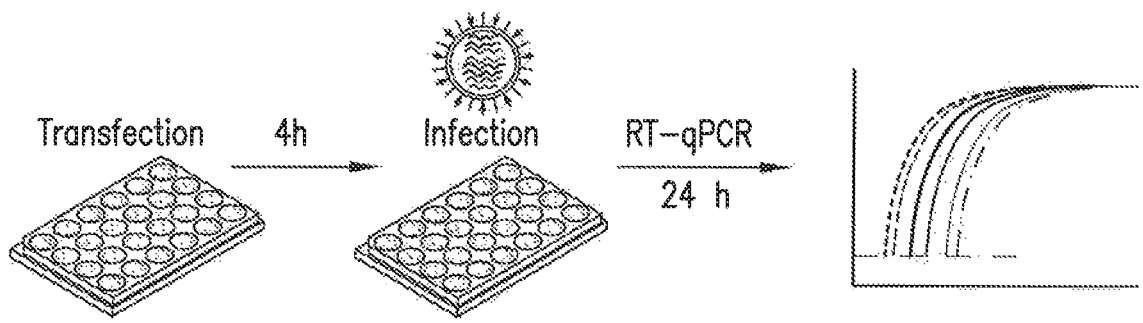
Figure 8B:
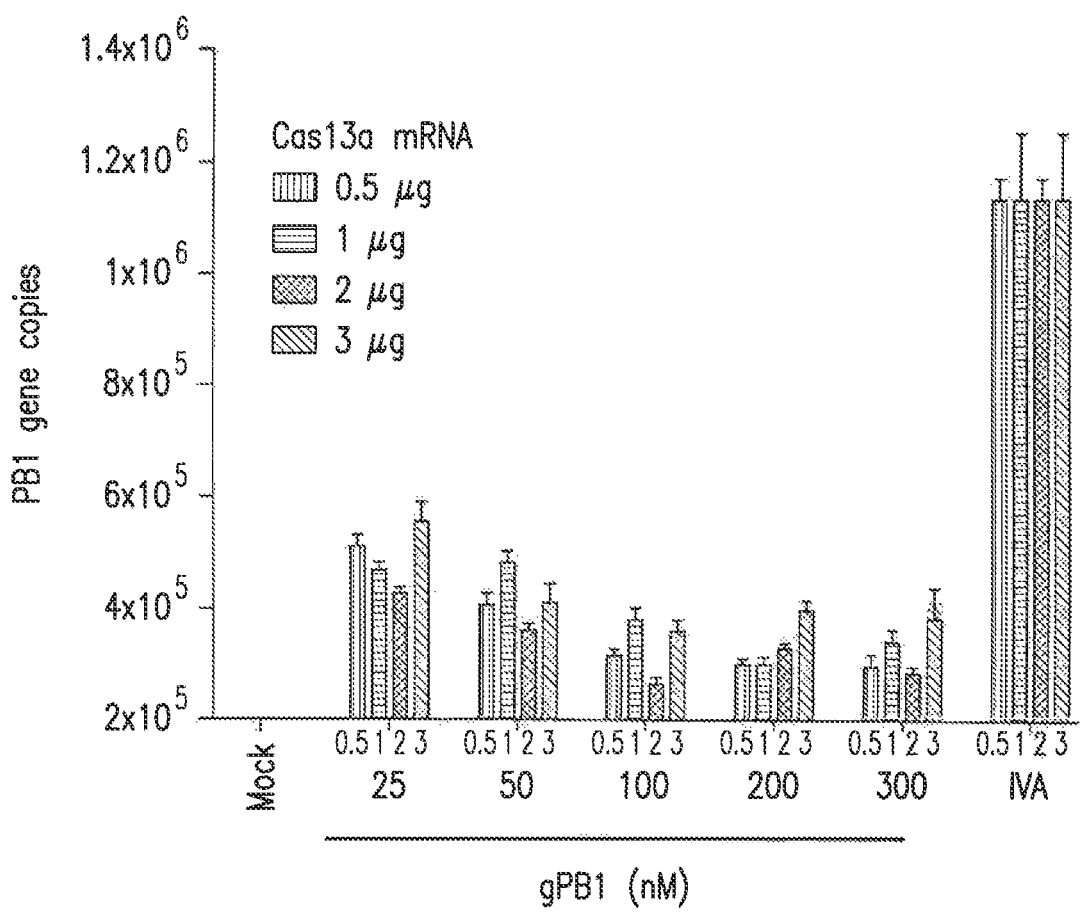

To determine the RNA doses required for IVA inhibition in cells, concentration of Cas13a mRNA and gPB1 (crRNA) was tested. Cells transfected with increased Cas13a mRNA and gPB1 concentration showed inversely proportional IVA infection. The dose-dependent IVA inhibition was observed until 200 nM gPB1, further increase in crRNA did not reduce the IVA infection. At the lowest (Cas13a mRNA (0.5

μg) and gPB1 (25 nM)) and at highest (Cas13a mRNA (3 μg) and gPB1 (300 nM)) combination the IVA infection was reduced by 0.35 logs (55%) and 0.48 logs (66%) PB1 copies, respectively (FIGS. 8A-8B). The highest inhibition was seen in 2 ng Cas13a and 100 nM gPB1 (76.78%). However, a moderate and yet efficient Cas13a mRNA (1 μg) and gPB1 (100 nM) dose was used for all our subsequent IVA experiments in cells.

Optimizing Viral Infections in A549 Cells

Figure 8C:
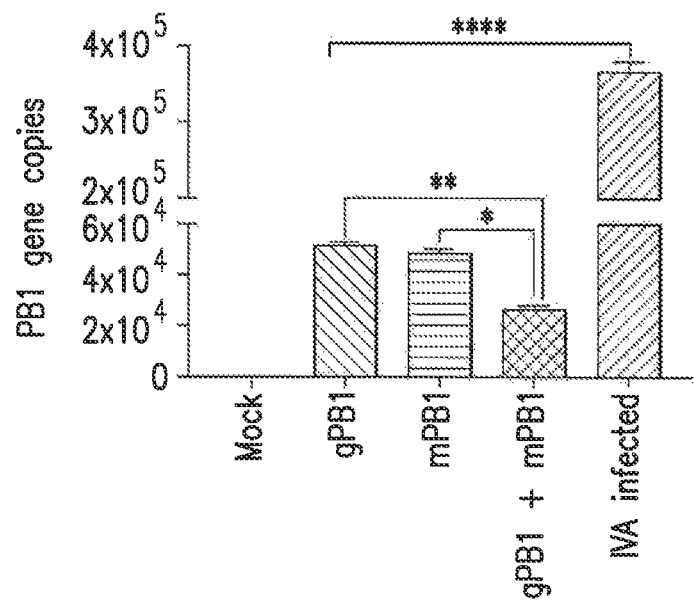
Figure 8D:
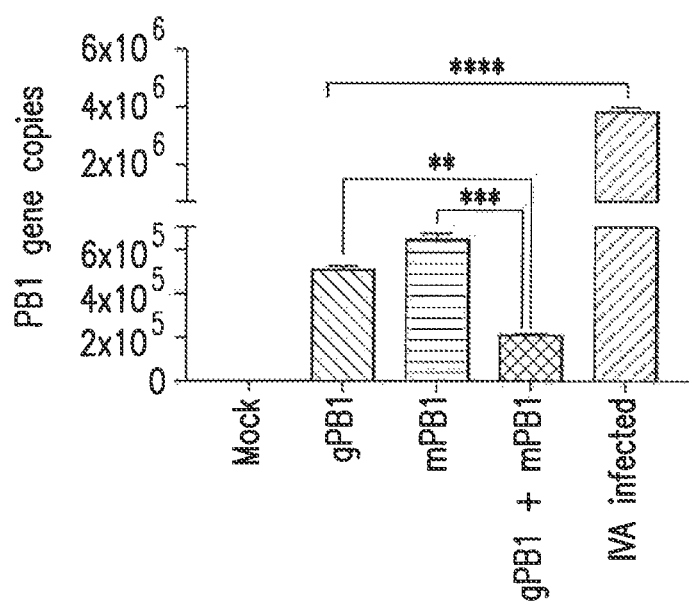

Next, a number of experimental conditions were investigated, in order to characterize the performance of the Cas13a:crRNA system. The effect of MOI was evaluated, demonstrating that Cas13a:crRNAs targeting PB1 were able to reduce the influenza virus gene copies by 0.77-1.26 log (21% to 72.4%) 24 h post transfection (FIG. 8B). The optimum viral titer was evaluated by testing gPB1 at MOI of 0.01 (FIG. 8C) and 0.1 (FIG. 8D), both physiologically relevant MOIs. At MOI 0.01, the inhibition was 85.8%, 86.6% and 92.5% gPB1, mPB1 and gPB1+mPB1, respectively. Similarly, at MOI 0.1 the reduction in PB1 copy numbers were 86.7%, 83.1% and 94.5% for gPB1, mPB1 and gPB1+mPB1, respectively.

Figure 10A:
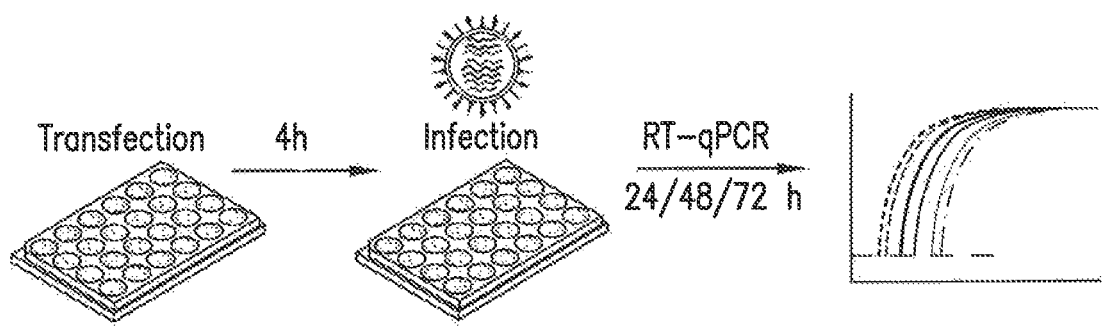
Figure 10B:
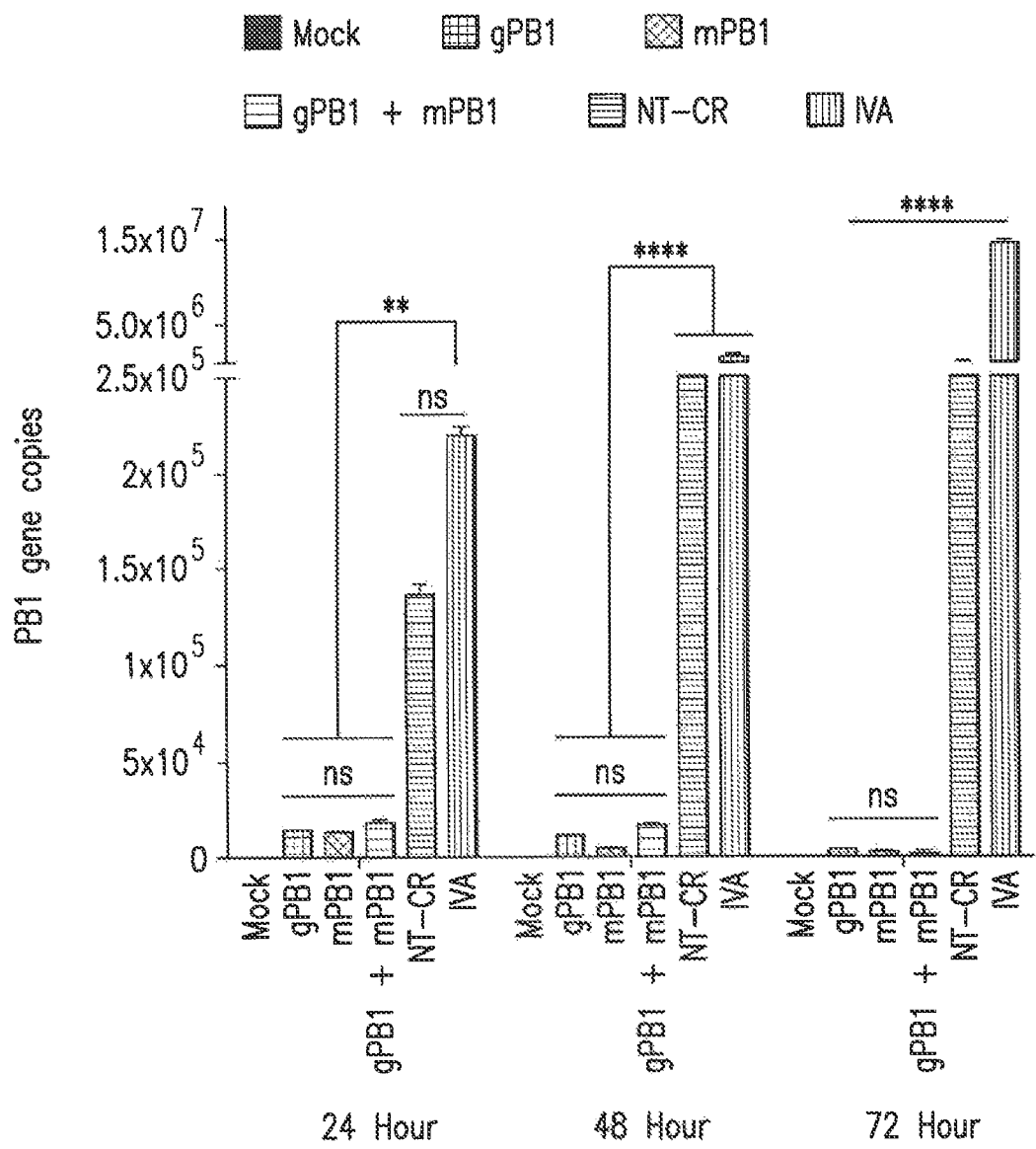
Figure 10C:
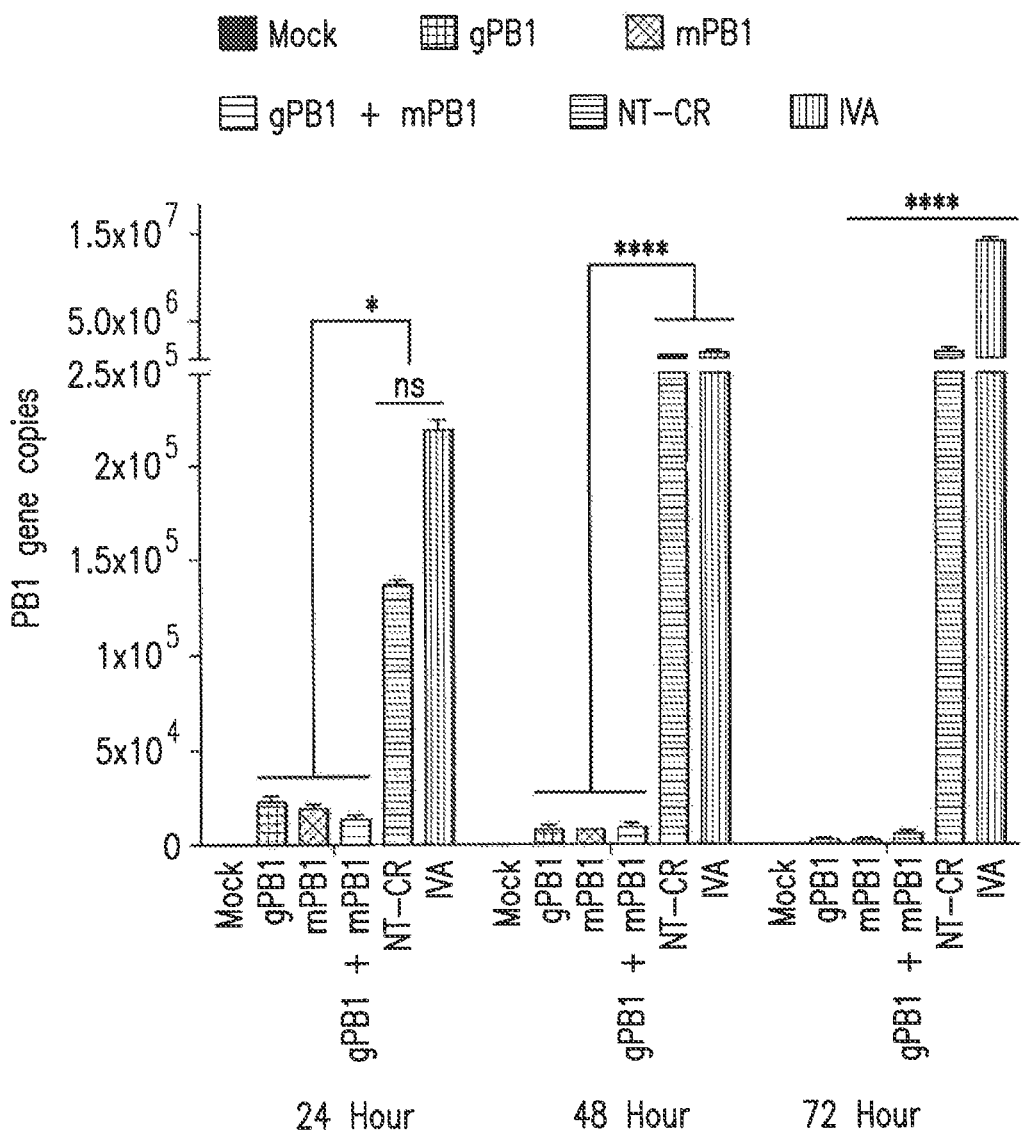

Example 6. Cas13a:crRNA Transfected Cells have Reduced IVA Infection in Dose and Time Dependent Manner Results:

Time dependent degradation of viral RNA during the infection was investigated (FIG. 10A). Targeting either the gPB1 or mPB1 reduced viral copies by 0.96-1.21 log (89.2% to 93.9%) at 24 h, 1.88-2.6 log (98.6% to 99%) at 48 h, but further reduced viral RNA copies by 3.53-3.8 logs (99.97% to 99.98%) at 72 h for both Cas13a (FIG. 10B) and Cas13a-NLS (FIG. 10C). This data is noteworthy, as the prolonged effect of Cas13a interrupts IVA replication and reduced viral RNA copies up to 72 h.

Example 7. Cas13a:crRNA System Reduces IVA Infection in Pre-Infected Cells

Figure 9:
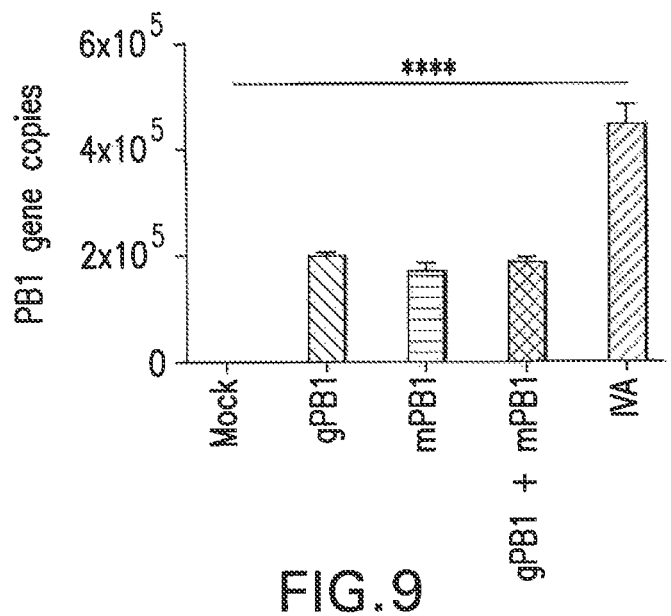
Figure 10D:
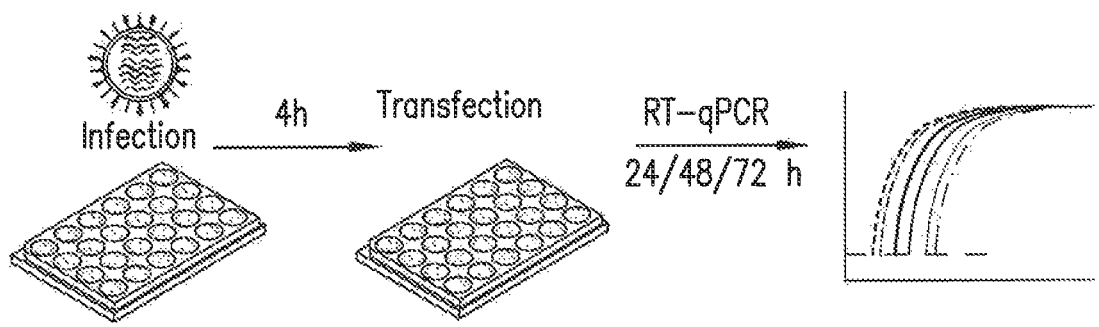
Figure 10E:
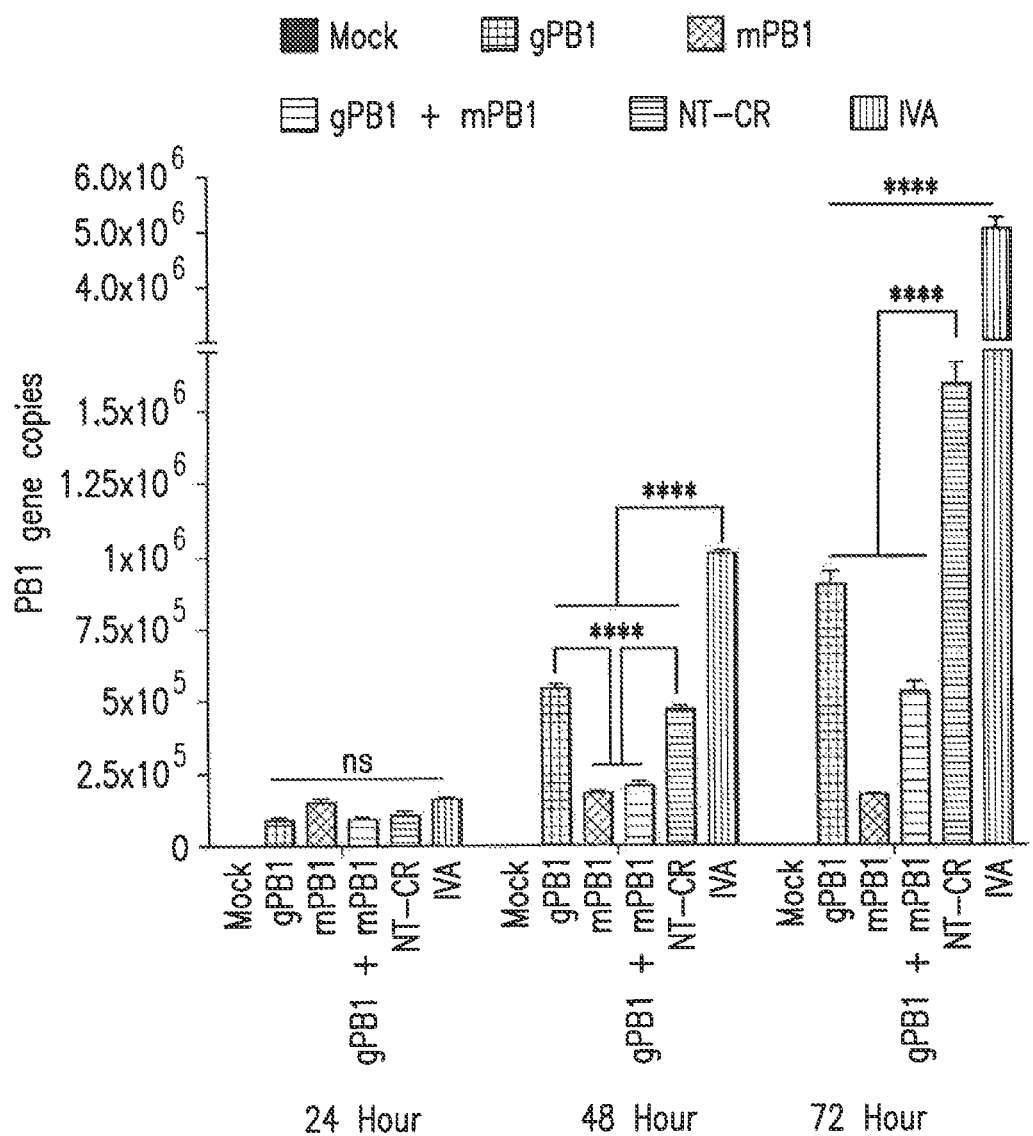
Figure 10F:
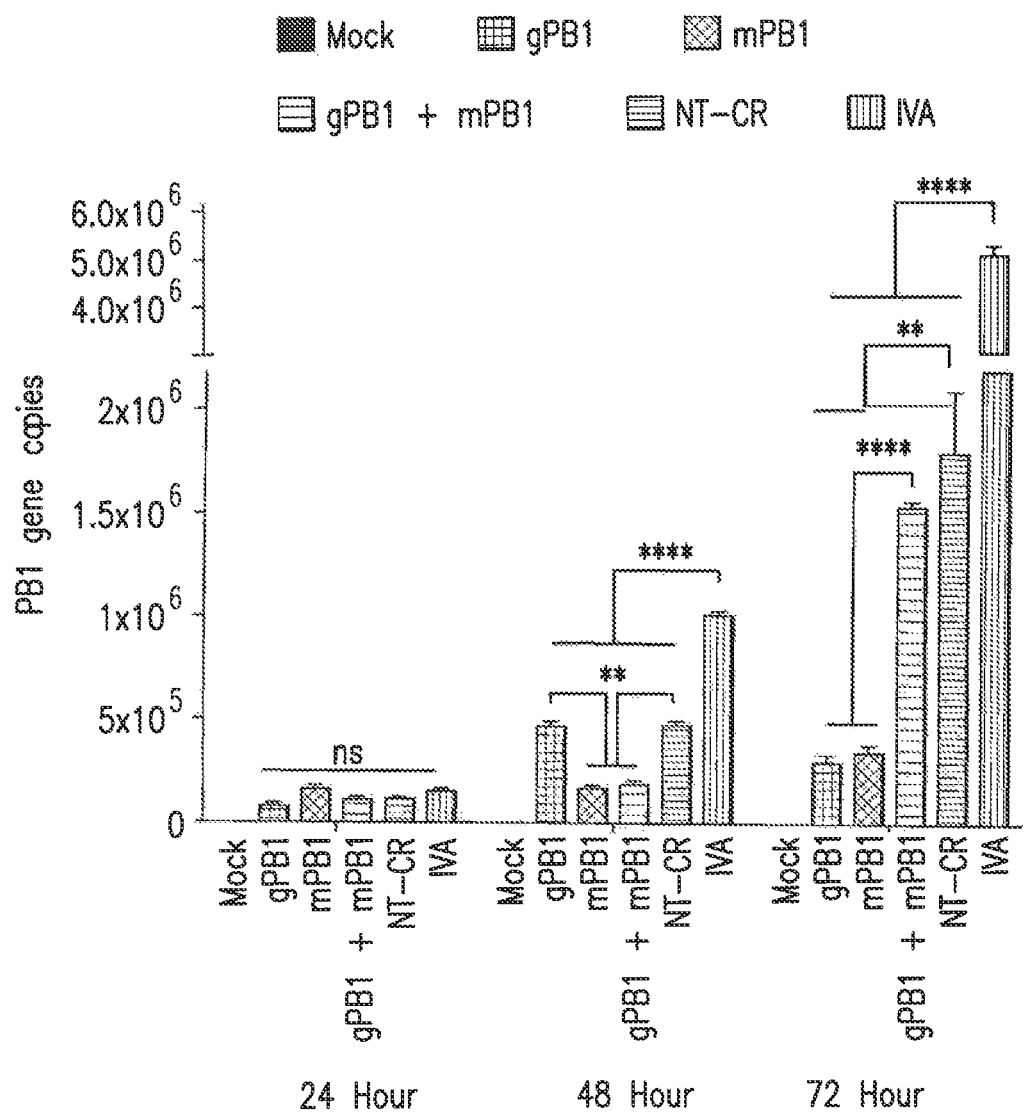
Figure 10G:
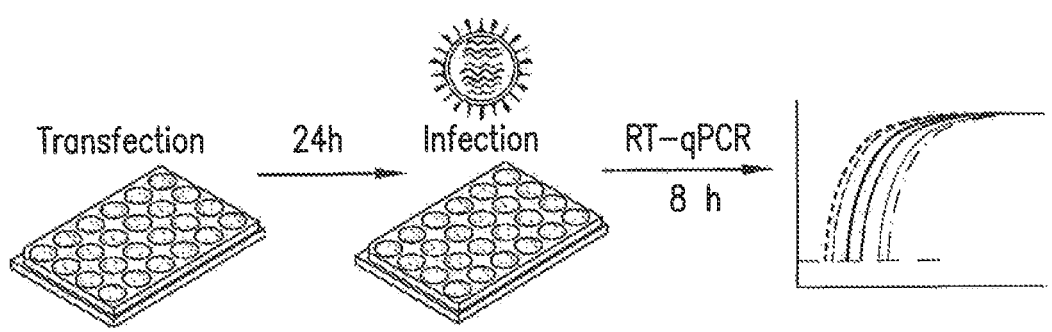
Figure 10H:
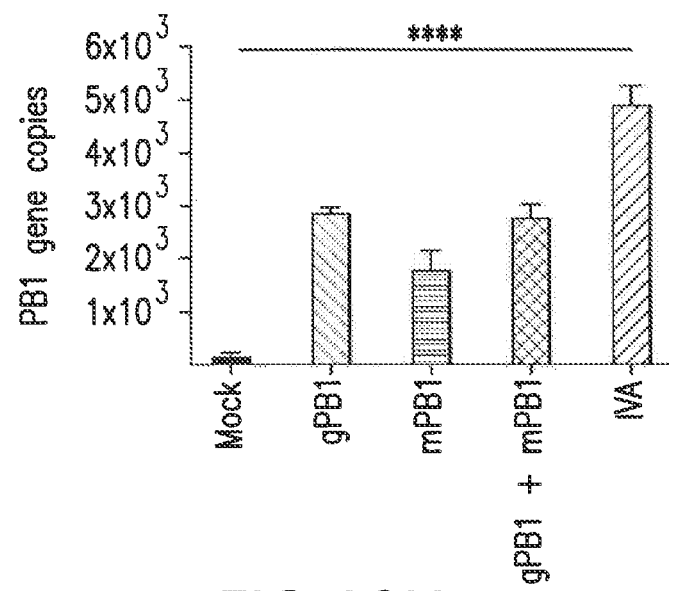
Figure 10I:
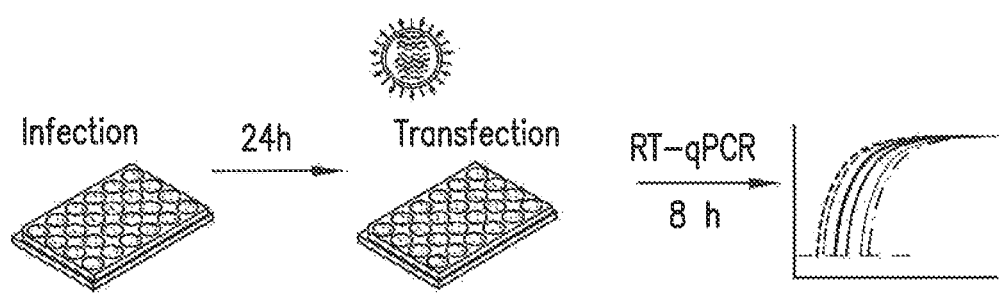
Figure 10J:
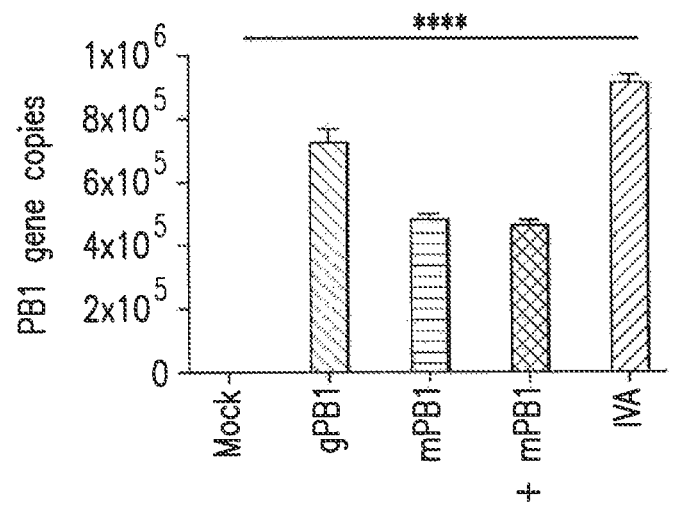

Results:

Because the Cas13a: crRNA system mitigates IVA infections in a simulated "prophylactic manner", the ability of Cas13a:crRNA system to reduce infection in cells already infected with IVA was assessed. The cells infected with IVA (MOI 0.01) for 4 h were later transfected with Cas13a/Cas13a-NLS mRNA and crRNA (gPB1 and mPB1) (FIG. 10D), and the effect on IVA was monitored for 72 hours. A maximum of 0.74 log (83.3%) reduction was observed in IVA copy numbers with either Cas13a (FIG. 10E) or Cas13a-NLS (FIG. 10F) after 48 and 1.47 log (93.9%) reduction after 72 h of transfection. The efficiency of Cas13a-crRNA on the IVA infection was evaluated by transfecting the cells with Cas13a mRNA and crRNA for 24 h, anticipating a decrease in expression of Cas13a (based on FIG. 10G), and then infecting with influenza virus for 8 h (FIG. 10H). Under this condition, a maximum of 0.3 log (63%) reduction of IVA was still observed, thus underlining the robustness of the Cas13a mediated targeting of IVA. Similarly, the effect of prolonged infection on Cas13a mediated RNA targeting was evaluated. Here, the cells were infected for 24 h, followed by transfection and evaluation of viral copy numbers 8 h post transfection (FIG. 10I). In this case too, a significant reduction in viral titer was observed, up to 49% (FIG. 10J). Thus, from these experiments it was demonstrated that Cas13a is effective in inhibiting IVA in both prophylactic and post-infection treatment. It was also observed that Cas13a:crRNA system effectively inhibits IVA up to 62%, in a normal human primary bronchial/tracheal epithelial cell model (FIG. 9). The inhibition of IVA by Cas13a:crRNA differs in cell types as the transfection efficiency differs with cell types. Primary cells are usually difficult to transfect, however, here proof-of-concept that this approach can be applied to human primary cells is shown.

Figure 11A:
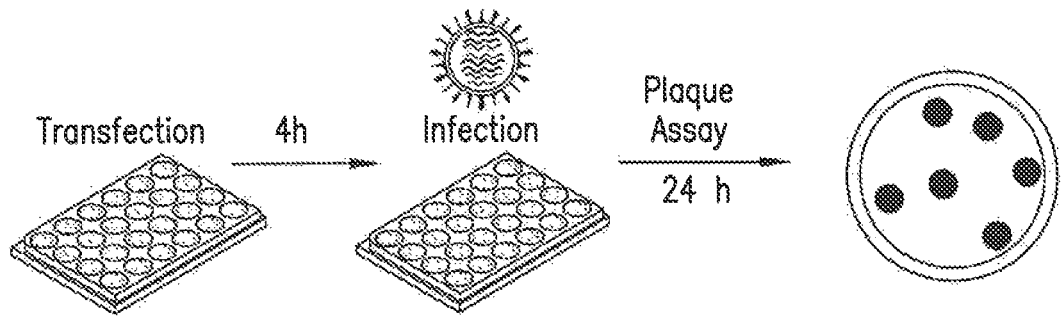
Figure 11B:
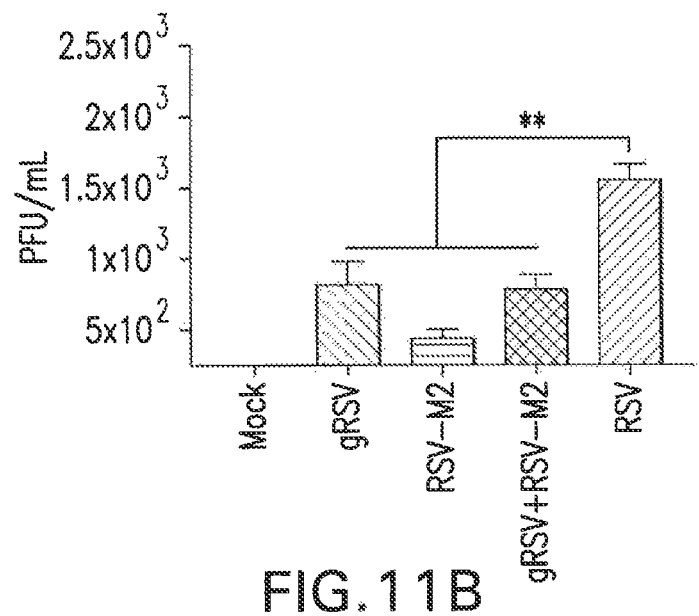
Figure 11C:
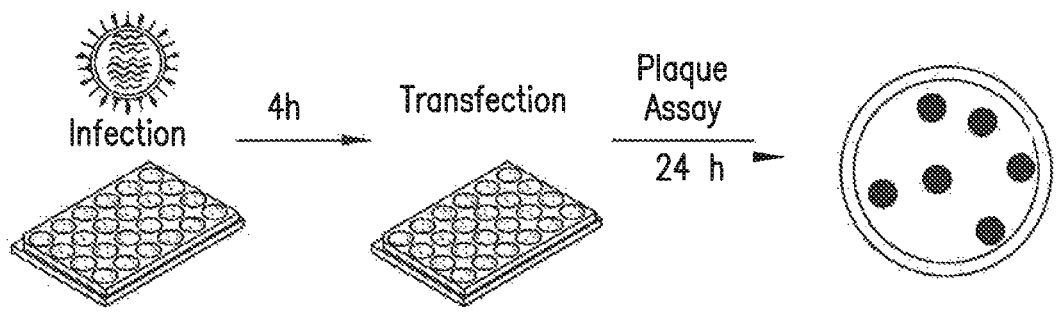
Figure 11D:
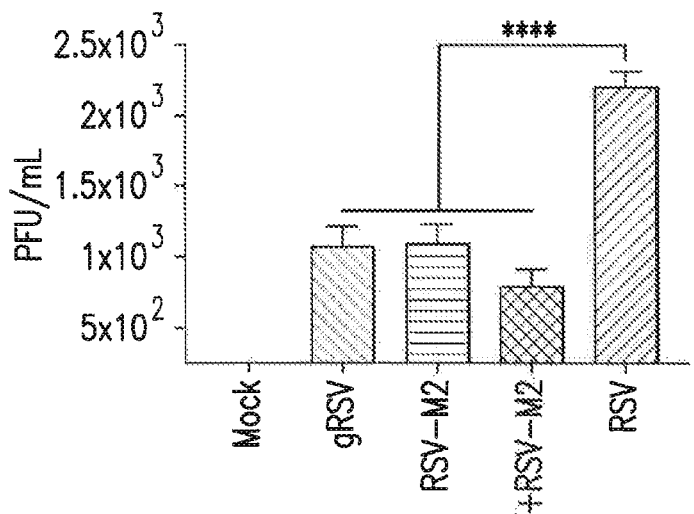
Figure 12A:
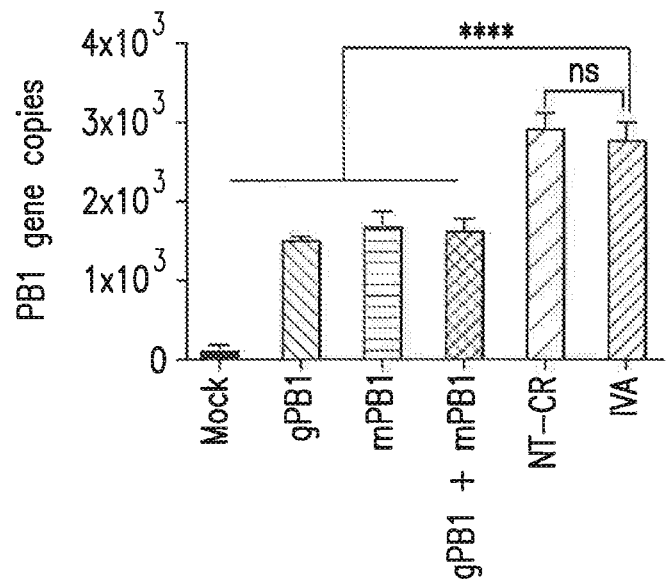
Figure 12B:
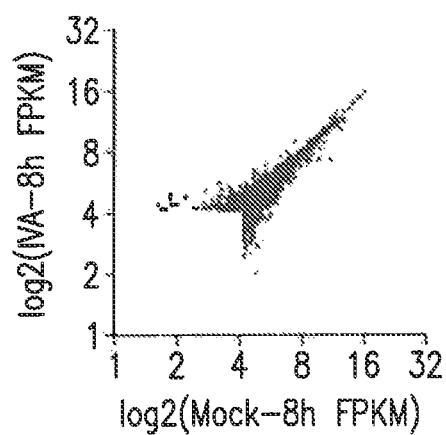
Figure 12C:
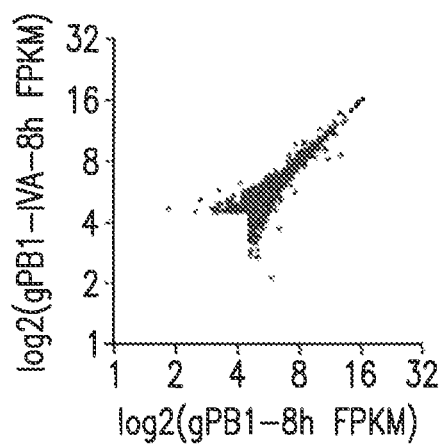
Figure 12D:
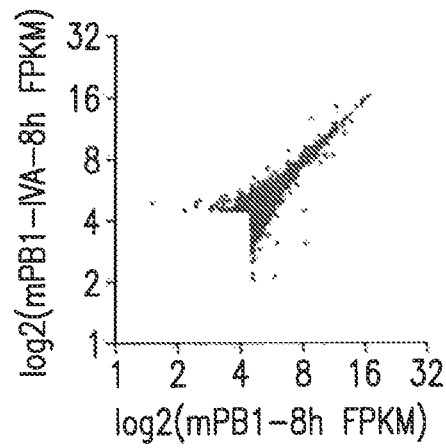
Figure 12E:
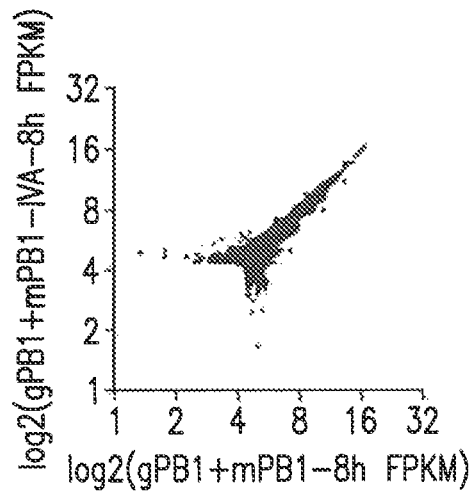
Figure 12F:
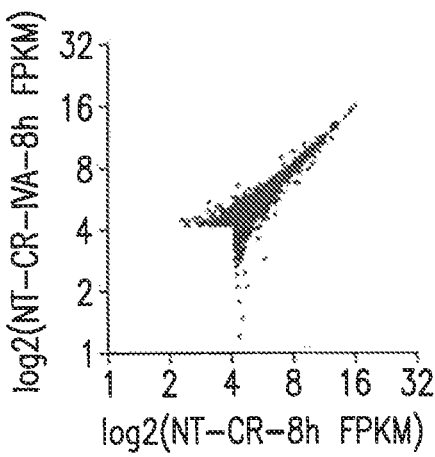
Figure 12G:
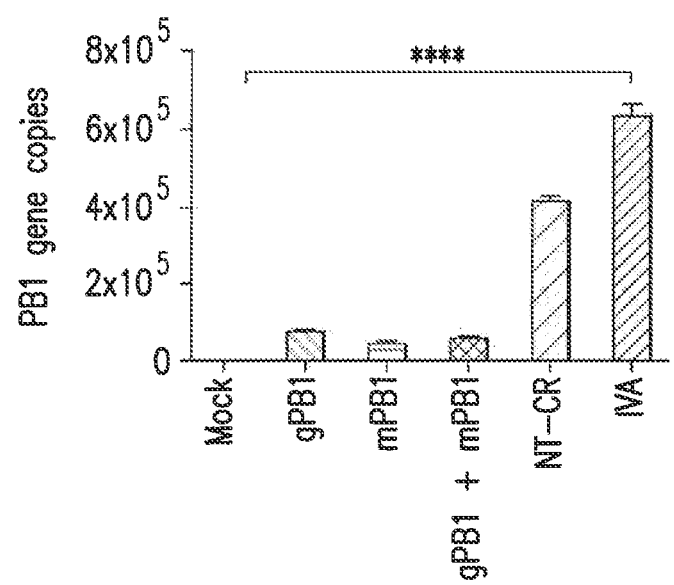
Figure 12H:
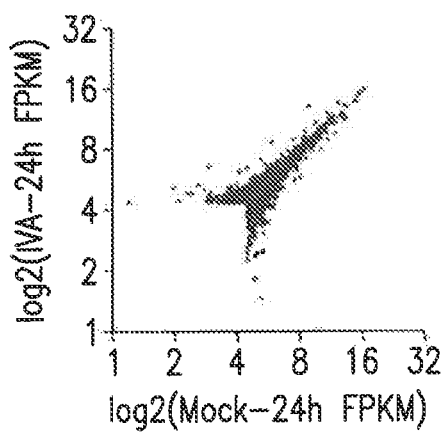
Figure 12I:
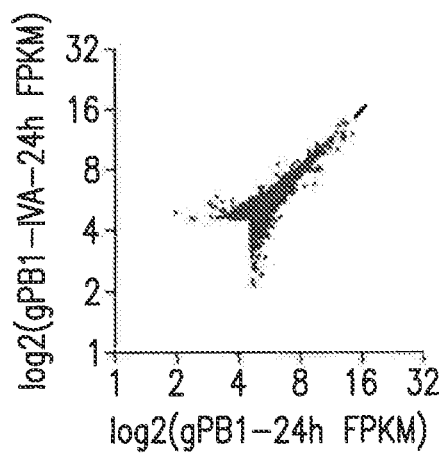
Figure 12J:
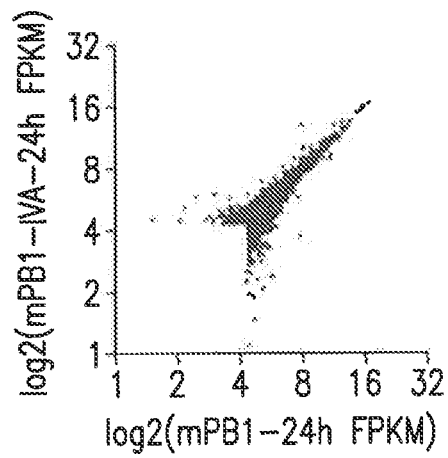
Figure 12K:
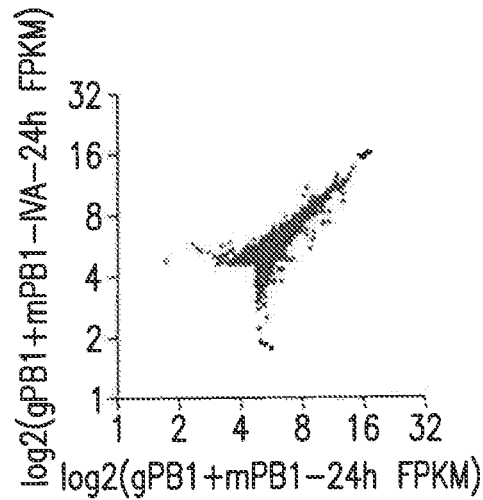
Figure 12L:
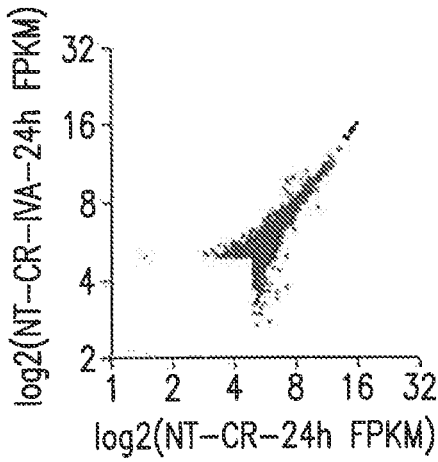

Example 8. Cas13a:crRNA can be Programmed to Target Other Viruses Like hRSV Infection Results:

The Cas13a-crRNA system offers the potential to target various viral pathogens through the design of specific crRNAs. To demonstrate this, crRNA were designed against both the human respiratory syncytial virus (RSV) genome (gRSV) and the M2 mRNA (RSV-M2). Cells transfected with Cas13a mRNA and both crRNAs exhibited reduced RSV titers, both as prophylaxis (FIGS. 11A-11B) and post-infection (FIGS. 11C-11D). There was a maximum of 0.55 log (71%) reduction in Cas13a:crRNA when given prior to infection (FIG. 10B). However, when infected with RSV before transfection, Cas13a:crRNA reduced RSV titer by 0.3-0.44 log (63.5%) in gRSV and m1.1, given together, whereas viral titer in crRNAs targeting genome (gRSV) and RSV mRNA (RSV-M2) given individually was 51.3% and 49.7%, respectively (FIG. 10D). It should be noted that ~71% knockdown via prophylaxis in hRSV was observed and these data were obtained with a first-generation guide, based only on the M2/L gene end sequence. These results are encouraging as inhibition is seen at the MOI of 1, which is significantly higher than naturally occurring infections. In addition, in the cells receiving Cas13a:crRNA, the plaques were not only diminished in number but also in size, demonstrating lower cell-to-cell spread and possibly the generation of more defective interfering (DI) particles. Overall, this result alone is extremely promising, as future unbiased guide screens against the hRSV genomic and mRNA will likely yield improved knockdown. These findings demonstrate the potential of the Cas13a: crRNA system as an antiviral approach, likely applicable to several viral pathogens.

Example 9. No Off-Target RNA Cleavage was Detected as Mediated by Cas13a

Results:

The Cas13a activity was specific in cleaving IVA RNA and did not result in any detectable off-target RNA cleavage. The transcriptome profile of cells transfected with Cas13a mRNA and crRNA (PB1) at 8 and 24 h post-delivery, with or without infection with IVA, showed no significant changes in endogenous gene expression at the level of mRNA (FIGS. 12A-12L). Similarly, specific endogenous mRNA knockdown in cells with no off-target activity was reported previously in *Leptotrichia wadei* Cas13a (Abudayyeh, O. O. et al., *Nature,* 550:280-284 (2107)). It could be argued that any possible off-target activity of Cas13a may be difficult to determine by RNA-Seq as the ongoing transcription and Cas13a mediated degradation may negate each other to infer any significant change in gene expression. However, it is shown that Lbu Cas13a has distinct activities-RNA binding (crRNA and target RNA) and RNase activity. The Cas13a can bind mismatched crRNA-target, but it does not lead to RNA cleavage (Tambe, A., et al., *Cell Rep,*

24:1025-1036 (2018)). The RNase activity is activated only when the crRNA and target RNA are complimentary, thus off-target activity of Cas13a may be ruled out.

While in the foregoing specification this invention has been described in relation to certain embodiments thereof, and many details have been put forth for the purpose of illustration, it will be apparent to those skilled in the art that the invention is susceptible to additional embodiments and that certain of the details described herein can be varied considerably without departing from the basic principles of the invention.

All references cited herein are incorporated by reference in their entirety. The present invention may be embodied in other specific forms without departing from the spirit or essential attributes thereof and, accordingly, reference should be made to the appended claims, rather than to the foregoing specification, as indicating the scope of the invention.

We claim:

1. A composition for inactivating RNA viruses in vitro or in vivo, comprising: an isolated nucleic acid construct encoding an RNA-guided endonuclease and, at least one guide RNA (gRNA), wherein the gRNA is complementary to a target nucleic acid sequence in an RNA-viral genome; and wherein the isolated nucleic acid construct further comprises a nuclear localization sequence, wherein the isolated nucleic acid construct has a sequence according to SEQ ID NO:2.

2. The composition of claim 1, wherein the RNA virus is an influenza virus or respiratory syncytial virus.

3. The composition of claim 1, wherein the RNA virus is a negative-strand RNA virus.

4. The composition of claim 1, wherein the RNA virus is a positive-strand RNA virus.

5. A pharmaceutical composition comprising the composition of claim 1 and a pharmaceutically acceptable carrier.

6. A method of treating a RNA viral infection in a subject in need thereof, comprising administering to the subject the composition of claim 1 in an amount effective to inhibit viral replication in the subject.

7. The method of claim 6, wherein the guide RNA construct targets a viral gene.

8. The method of claim 7, wherein the viral gene is neuraminidase (NA), hemagglutinin (HA), ion channel (M2), matrix protein (M1), nucleocapsid protein (NP), nuclear export protein (NS1 and NS2) or RNA polymerase PB1, PB2, or PA.

9. The method of claim 6, wherein the RNA virus is influenza virus.

10. The method of claim 9, wherein the RNA virus is respiratory syncytial virus.

* * * * *

UNITED STATES PATENT AND TRADEMARK OFFICE
CERTIFICATE OF CORRECTION

| | |
|---|---|
| PATENT NO. | : 11,795,456 B2 |
| APPLICATION NO. | : 17/047978 |
| DATED | : October 24, 2023 |
| INVENTOR(S) | : Bawage et al. |

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 157 days.

Signed and Sealed this
Eighth Day of July, 2025

Coke Morgan Stewart
*Acting Director of the United States Patent and Trademark Office*